United States Patent [19]

Shoji et al.

[11] Patent Number: 5,498,602

[45] Date of Patent: * Mar. 12, 1996

[54] OLIGOSACCHARIDE AROMATIC GLYCOSIDE AND SULFATE THEREOF

[75] Inventors: Tadao Shoji, Sakura; Nahoko Takahashi, Chiba; Naoya Ikushima, Sakura; Toshiyuki Uryu, Tokyo; Takashi Yoshida, Tokyo; Naoki Yamamoto, Tokyo; Hideki Nakashima, Tokyo; Kaname Katsuraya, Sakura; Koichiro Adachi, Kashiwa; Fusayo Kataoka, Narashino, all of Japan

[73] Assignee: Dainippon Ink and Chemicals, Inc., Tokyo, Japan

[*] Notice: The portion of the term of this patent subsequent to Oct. 17, 2012, has been disclaimed.

[21] Appl. No.: 944,077

[22] Filed: Sep. 11, 1992

[30] Foreign Application Priority Data

| Sep. 13, 1991 | [JP] | Japan | 3-234728 |
| Oct. 16, 1991 | [JP] | Japan | 3-267611 |
| Feb. 5, 1992 | [JP] | Japan | 4-019972 |

[51] Int. Cl.$^6$ ............... A61K 31/70; C07G 3/00; C07H 11/00
[52] U.S. Cl. ............... 514/25; 536/4.1; 536/115; 536/116; 536/118; 536/123.1
[58] Field of Search ............... 536/4.1, 118, 115, 536/116, 123.1; 514/25

[56] References Cited

U.S. PATENT DOCUMENTS

| 4,524,066 | 6/1985 | Wolf | 514/23 |
| 4,761,401 | 8/1988 | Couchman et al. | 514/53 |
| 4,885,361 | 12/1989 | Wessel | 536/118 |
| 4,980,462 | 12/1990 | Karlsson et al. | 536/53 |
| 5,011,923 | 4/1991 | Ono et al. | 536/17.9 |
| 5,280,111 | 1/1994 | Shoji et al. | 536/4.1 |

FOREIGN PATENT DOCUMENTS

| 0240098 | 10/1987 | European Pat. Off. |
| 0301400 | 2/1989 | European Pat. Off. |
| 0342544 | 11/1989 | European Pat. Off. |
| 0385464 | 9/1990 | European Pat. Off. |
| 0447171 | 9/1991 | European Pat. Off. |
| 3921761 | 3/1991 | Germany |
| 0164722 | 9/1984 | Japan |
| 0045587 | 3/1985 | Japan |
| 62-289595 | 12/1987 | Japan |
| 63-183595 | 7/1988 | Japan |
| 64-16797 | 1/1989 | Japan |
| 64-68389 | 3/1989 | Japan |
| 64-68392 | 3/1989 | Japan |
| 1-311094 | 12/1989 | Japan |
| 2-11595 | 1/1990 | Japan |

OTHER PUBLICATIONS

Biochemistry, 2nd ed., p. 249, © 1975.

*Primary Examiner*—David M. Naff
*Assistant Examiner*—Deborah K. Ware
*Attorney, Agent, or Firm*—Armstrong, Westerman, Hattori, McLeland & Naughton

[57] ABSTRACT

Oligosaccharide aromatic glycoside sulfates and physiologically acceptable salts thereof, are disclosed. Further, antiviral agents having these sulfate compounds as the active components, and particularly an antiviral agent, wherein the virus is one which causes AIDS (Acquired Immune Deficiency Syndrome), are disclosed. The active components or the glycoside sulfates, and the salts thereof, are characterized by an oligosaccharide aromatic glycoside sulfate in which the hydrogen of the position-1 hydroxyl group of the terminal sugar of an oligosaccharide is substituted with a specified formula having an alkyl group consisting of 1 to 18 carbons, an oxygen or no oxygen, and an allylene group. The number of constituent monosaccharides in the oligosaccharide portion is preferably within a range of 2 to 20. Further, 10% or more of the remaining hydroxyl groups of the sugar subunits are subjected to sulfated esterification. In addition the antiviral agent exhibits low toxicity and is useful in the treatment of AIDS. Furthermore, an oligosaccharide is also disclosed as described above with the exception that it is the hydrogen atom of the position 1 hydrogen group at the terminal sugar residue which is substituted with the specified formula, also described above. However, in addition the remaining hydroxyl groups of the sugar portion of this oligosaccharide are protected by acyl groups or are present in an unprotected form. Also disclosed is a method for the production of an oligosaccharide aromatic glycoside sulfate synthesized by sulfation using a sulfating agent.

3 Claims, No Drawings

OLIGOSACCHARIDE AROMATIC GLYCOSIDE AND SULFATE THEREOF

BACKGROUND OF THE INVENTION

1. Field of the Invention

The present invention relates to a novel oligosaccharide aromatic glycoside sulfate, as well as to physiologically acceptable salts thereof and antiviral agents with oligosaccharide aromatic glycoside sulfates and their physiologically acceptable salts as active components.

2. Background Art

Monosaccharides into which aminophenol has been introduced, such as those disclosed in Japanese Patent Application First Publication Laid-Open No. Showa 64-68389, and Japanese Patent Application First Publication Laid-Open No. Showa 64-68392 and the like, are known as monosaccharide aromatic glycosides in which aryl or alkylaryl has been introduced into aglycon as a hydroxyl group protective group at a sugar anomeric position (position-1). Compounds in which aromatics are introduced into oligosaccharides are known in Japanese Patent Application, First Publication Laid-Open No. Heisei 1-311094 and Japanese Patent Application, First Publication Laid-Open No. 5Showa 62-289595; furthermore, a compound into which nitrophenyl is introduced as a chromophore for the purpose of the optical measurement of α-amylase in blood serum is disclosed in Japanese Patent Application, First Publication Laid-Open No. Heisei 2-11595, and a compound into which naphthalene, anthracene or the like is introduced is disclosed in Japanese Patent Application, First Publication Laid-Open No. Showa 63-183595. However, in each case, a malt oligosaccharide comprising glucose is used as the sugar. No disclosure has yet been made regarding oligosaccharide aromatic glycosides comprising lactose or galactose, or oligosaccharide aromatic glycosides in which glucose is connected by means of 1→3 bonds. Furthermore, the oligosaccharide aromatic glycoside sulfate of the present invention, in which a sulfuric ester is introduced into a hydroxyl group of an oligosaccharide aromatic glycoside, and furthermore, the antiviral activity thereof, are not conventionally known.

Recently, there have been reports of polysaccharide sulfates which are used as antiviral agents; however, as the molecular weights thereof reach into the tens of thousands, the absorbability into the body is poor, and it is becoming gradually clear that such antiviral agents have a number of problems such as the difficulty of an oral administration, possession of antigenicity, and powerful anticoagulant function. Furthermore, it is particularly true that the continuous concentration in the blood is often poor, and that there is a weak point in that the agent breaks down within one hour of administration. In addition, the nucleic acid compound AZT (3'-azido-2',3'-dideoxthymidine), which is widely used as an anti-AIDS agent, also produces strong side effects, so that the development of a new drug possessing low toxicity is desirable.

SUMMARY OF THE INVENTION

As a result of these research with the aim of producing a superior antiviral agent, the present inventors have produced a novel oligosaccharide aromatic glycoside sulfate as well as physiologically acceptable salts thereof by means of sulfating a novel oligosaccharide aromatic glycoside using a sulfating agent, and by means of testing the safety and physiological activity thereof, have determined that this superior antiviral agent possesses low toxicity.

The present invention comprises a oligosaccharide aromatic glycoside sulfate in which the hydrogen of the position-1 hydroxyl group of the terminal sugar of an oligosaccharide consisted of a same monosaccharide or a combination of different monosaccharides bonded by glycoside bonds is substituted by formula (I):

$$-Y-(O)_n-R \quad (I)$$

(in this formula, R represents an alkyl group having 1–18 carbon atoms, n represents 0 or 1, O represents an oxygen atom, and Y represents an allylene group), and a portion or all of the remaining hydroxyl groups of the sugar portion sulfuric esterificated; and further comprising the physiologically acceptable salts of this oligosaccharide aromatic glycoside sulfate.

Furthermore, an antiviral agent having the characteristics of containing, as active components, this oligosaccharide aromatic glycoside sulfate or the physiologically acceptable salts thereof, and particularly an antiviral agent wherein the virus is the AIDS virus, are disclosed.

In addition, the present invention relates to an oligosaccharide aromatic glycoside (excluding oligosaccharide aromatic glycosides having a monosaccharide structure in which glucose is bonded by α (1→4) glycoside bonds) comprising an oligosaccharide consisted of a same monosaccharide or a combination of different types of monosaccharides, bonded by glycoside bonds, in which a hydrogen atom of the position-1 hydrogen group at the terminal sugar has been substituted by a group represented by the following formula:

$$-Y-(O)_n-R \quad (I)$$

(in this formula, R represents an alkyl group having 1–18 carbon atoms, n represents 0 or 1, O represents an oxygen atom, and Y represents an allylene group), the oligosaccharide comprising a sugar chain in which the remaining hydroxyl groups of the sugar portion are protected by means of acyl groups or are present in an unprotected form, and further pertains to a method for the production of an oligosaccharide aromatic glycoside sulfate synthesized by means of sulfation using a sulfating agent.

DETAILED DESCRIPTION OF THE PREFERRED EMBODIMENTS

The oligosaccharides used in the oligosaccharide aromatic glycoside sulfate of the present invention comprise one or some monosaccharides selected from the groups of glucose, galactose, mannose, xylose, fucose, and the like; however, in addition to these, those comprising sugars having an amino group such as glucosamine, galactosamine, or the like, and monosaccharides having a carboxyl group such as glucoronic acid, galactoronic acid, and the like are also usable.

From the standpoint of antiviral activity, the number of constituent monosaccharide units optimally used to form the oligosaccharide aromatic glycoside sulfate of the present invention is variable, depending on the type or types of monosaccharides used therefor; however, ordinarily, a number of 20 individual monosaccharides or less is desirable when consideration is given to the anticoagulant effects seen in the cases of polysaccharide sulfates and to physiological compatibility. Accordingly, the number of constituent monosaccharide units of the oligosaccharide portion of the oligosaccharide aromatic glycoside sulfate of the present invention is optimally within a range of from 2 to 20.

From the standpoint of antiviral activity, with regard to the glycoside bonds between monosaccharides of the oligosaccharide aromatic glycoside sulfate of the present invention, any selected from a group including (1→2), (1→3), (1→4), and (1→6) are usable. Furthermore, the use of an oligosaccharide having comparatively small in vivo degradation is desirable in order to achieve long-term activity, so that β bond is preferable to α bond. In addition, with regard to bonding position, (1→3) and (1→6) bonds are preferable to (1→4).

Similarly, in the oligosaccharide aromatic glycoside, as well, the oligosaccharide used in the oligosaccharide aromatic glycoside of the present invention comprise one or some monosaccharides selected from the group of glucose, galactose, mannose, xylose, fucose, and the like; however, in addition to this, those comprising sugars having an amino group such as glucosamine, galactosamine, and the like, and monosaccharides having a carboxyl group such as glucoronic acid, galactoronic acid, and the like are also usable, and the number of constituent monosaccharides in the oligosaccharide portion is preferably within a range of 2 to 20.

Furthermore, with regard to the glycoside bonds between monosaccharides in the oligosaccharide aromatic glycoside of the present invention, in the same manner, any selected from a group consisting of (1→2), (1→3), (1→4) and (1→6) are usable; however, as the use of an oligosaccharide having comparatively small in vivo degradation is desirable in order to achieve long-term activity, β bond is preferable to α bond. Furthermore, with regard to the bonding position, (1→3) and (1→6) are preferable to (1→4).

Oligosaccharide aromatic glycosides in which glucose is used as the sole constituent monosaccharide and is bonded by means of (1→4) glycoside bonds have been excluded from consideration as the oligosaccharide aromatic glycoside of the present invention; however, oligosaccharide aromatic glycosides comprising oligosaccharides in which, even though the sole constituent monosaccharide is glucose, the bonds between monosaccharides are not α (1→4) glycoside bonds, but rather are glycoside bonds selected from the group consisting of, for example, α (1→2), α (1→3), α (1→6), β (1→2), β (1→3), β (1→4), β (1→6), and the like, or oligosaccharide aromatic glycosides comprising oligosaccharides in which the bonds are α (1→4) glycoside bonds, but glucose is not the sole constituent monosaccharide, are also included in the scope of the present invention.

In the oligosaccharide aromatic glycoside sulfate of the present invention and the oligosaccharide aromatic glycoside which forms the raw material thereof, in the portion represented by formula (I), —Y—(O)$_n$—R, R represents an allylene group, O represents an oxygen atom, and n represents 1 or 0. That is to say, formula (I) represents the aglycon portion of the glycoside. In more detail, a phenylene group is preferable as Y, such as an aromatic alkyl group and an aromatic alkoxy group.

With respect to the portion represented by formula (I) of the oligosaccharide aromatic glycoside sulfate of the present invention, and the oligosaccharide aromatic glycoside which is the raw material thereof, in other words, with respect to the aglycon portion, the bonding position thereof is important, and it is desirable that the aglycon portion be introduced into the oligosaccharide at position-1 of the terminal reducing sugar thereof. The compound including —Y—(O)$_n$—R portion by formula (I), that is to say, the aglycon, is represented by formula (IV):

HO—Y—(O)n—R   (IV)

(in the formula, HO represents a hydroxyl group, and all other symbols have the identical meanings to those of formula (I)). Examples thereof include the following alkylphenols and alkoxyphenols. p-methylphenol, p-ethylphenol, p-propylphenol, p-butylphenol, p-penthylphenol, p-hexylphenol, p-heptylphenol, p-octylphenol, p-nonylphenol, p-decylphenol, p-dodecylphenol, p-tetradecylphenol, p-hexadecylphenol, p-octadecylphenol, p-methoxyphenol, p-ethoxyphenol, p-propoxyphenol, p-butoxyphenol, p-pentyloxyphenol, p-hexyloxyphenol, p-heptyloxyphenol, p-octyloxyphenol, p-nonyloxyphenol, p-decyloxyphenol, p-dodecyloxyphenol, p-tetradecyloxyphenol, p-hexadecyloxyphenol, and p-octadecyloxyphenol.

These examples are para position substituted products; either ortho position or meta position substituted products are also available.

Furthermore, the alkyl group bonded to the aromatic ring is available as either a straight chain or a branched form.

Conventional production methods are used for bonding the aglycon and the oligosaccharide. That is to say, synthesis is accomplished according to the following general production method, in which a compound shown in formula (IV) is introduced at the reducing terminal of the oligosaccharide.
(General Synthesis Method)
(1) Synthesis of glycoside peracetate [the peracetate of the compound of formula (III)]

(Q)$_m$—V—Y—(O)$_n$—R   (III)

(In the formula, R represents an alkyl group having 1–18 carbon atoms, n represents 0 or 1, O represents an oxygen atom, Y represents an allylene group, V represents a monosaccharide bonded by ether bonding to Y through the hydroxyl group at reducing terminal position-1, (Q)$_m$ represents an oligosaccharide polymerized by means of glycoside bonds, m represents a number of monosaccharides represented by an integer within a range of 1–19, and the oligosaccharide is comprising a sugar chain in which the remaining hydroxyl groups of the sugar subunits are protected by means of acyl groups or are present in an unprotected form (excluding an oligosaccharide aromatic glycoside having glucose as a sole component monosaccharide and bonded by means of α (1→4) glycoside bonds).

1 millimol of oligosaccharide peracetate and 1.2 to 1.6 millimol of phenyl derivative are dissolved in 4 milliliters of dehydrated methylene chloride, 1 to 1.5 millimol of TMS triflate(trifluoromethane sulfonic acid trimethylsilyl ether) are added, and the mixture is agitated for 5 to 30 hours in an atmosphere of inert gas at a temperature from −5° to −30° C., and allowed to react. After this reaction, triethyl amine is added; this is agitated for a short period, and after this, the mixture is returned to room temperature and dissolved in ethyl acetate and after washing in an aqueous solution of sodium bicarbonate, water washing and saturated aqueous saline washing, an organic layer is dehydrated and dried in sodium sulfate, the solvent is concentrated, and a crude product is obtained. When necessary, the product is refined by means of silica gel column chromatography or recrystallization.
(2) Alternate Method for the Synthesis of Glycoside Peracetate [the peracetate of the compound of the formula (III)]
1) Synthesis of 1-hydroxy-acetylated oligosaccharide After dissolving peracetyl oligosaccharide in dimethylformamide, hydrozinium acetate is added, and this is reacted at a temperature between room temperature and 100° C., and preferably at a temperature between room temperature and 70° C., for 0.5 to 5 hours, and preferably for 0.5 to 3 hours. After reaction, dilution by means of ethyl acetate is carried out, water is added, and separation is carried out, extraction is carried out several times by means of ethyl acetate, the ethyl acetate layer is collected, washing is carried out with saturated aqueous saline, and dehydration is carried out in sodium sulfate. After the ethyl acetate is removed under reduced pressure, the mixture is refined by means of the silica gel column chromatography method, if necessary, to conduct further refinement by means of recrystallization or reprecipitation methods.

2) Trichloroacetoiminoesterification

The 1-hydroxy-acetylated oligosaccharide produced in this manner is next reacted with trichloroacetonitrile and a trichloroacetoiminoester is thus formed.

That is, the 1-hydroxy-acetylated oligosaccharide synthesized in 1) above is mixed with trichloroacetonitrile in the presence of a solvent, a base, for example, sodium methoxide, DBU (1,8-diazabicyclo[5,4,0]undeca-1-ene) or the like is added, and then this is reacted at a temperature from −10° C. to room temperature. After the completion of the reaction, the desired compound is obtained by means of a silica gel column.

3) Reaction of an Alcohol with Glycoside Peracetate

The iminoester obtained according to the method of 2) and an alcohol are reacted for 1 to 10 hours at a temperature from −20° C. to room temperature in the presence of an acidic catalyst, for example, a catalyst selected from boron trifluoride ether, trifluoroacetic acid, sulfuric acid, or the like. After this reaction, the reaction solution is poured into an aqueous solution of sodium bicarbonate and extraction is performed by means of an organic solvent such as methylene chloride. After this process, the mixture is refined by means of the silica gel column chromatographic method, and it is thus possible to obtain the desired glycoside peracetate of formula (III).

(3) Synthesis of the Glucoside [the compound of formula (III)]

1 millimol of the glycoside peracetate thus obtained is dissolved in 4 milliliters of methanol at room temperature, 1.5 milliliters of a 0.1 normal methanol solution of sodium methoxide is added, and this is agitated for 2 to 24 hours, and deacetylation is carried out. By means of adding $H^+$-type ion-exchanging resin to this methanol solution, or by passing this methanol solution through an $H^+$-type ion-exchanging resin column, the sodium ions are exchanged for hydrogen ions, and by eliminating the solvent, the desired compound is obtained.

(4) Synthesis of the Oligosaccharide Aromatic Glycoside Sulfate [compound of formula (II)]

$(Z)_m-W-Y-(O)_n-R$  (II)

(In the formula, R represents an alkyl group having 1–18 carbon atoms, n represents 0 or 1, O represents an oxygen atom, Y represents an allylene group, W represents a monosaccharide bonded by ether bonding to Y through the hydroxyl group at reducing terminal position-1, $(Z)_m$ represents an oligosaccharide polymerized by means of glycoside bonds, and m represents a number of monosaccharides represented by an integer within a range of 1–19, and the oligosaccharide is comprising a sugar chain in which all or a portion of the hydroxyl groups are subjected to sulfated esterification.).

Various sulfating methods are known, including piperidine sulfonic acid in dimethyl sulfoxide, sulfur trioxide pyridine complex in pyridine, sulfur trioxide triethylamine complex, sulfur trioxide complex in dimethyl formamide, chlorosulfonic acid in pyridine, and the like; any method is available for use, however, here, the method using sulfur trioxide pyridine complex in pyridine is explained as one example.

The alkylated oligosaccharide is dissolved in pyridine, and the equivalent amount of sulfur trioxide pyridine complex which is necessary with respect to the sugar hydroxyl group is added. In the case in which complete sulfation is to occur, 1.2 to 3 times the equivalent amount of sulfur trioxide pyridine complex is used with respect to the sugar hydroxyl group. A reaction is carried out in an atmosphere of an inert gas within a range of temperature from room temperature to 100° C., and preferably from 50° to 85° C., and for 0.5 to 15 hours, and preferably from 0.5 to 10 hours, and the resulting precipitate is separated from the pyridine. The separated precipitate is again washed with pyridine, this precipitate is dissolved at room temperature in an appropriate amount of ion-exchanged water, an aqueous solution of barium hydroxide is added, and the pH of this solution is adjusted to 7 to 8. The precipitate which is occured at this time is separated by means of a centrifuge and is eliminated. The solution remaining after the elimination of the precipitate is passed through a sodium ion type ion-exchanging resin column (Amberlite IR-120 B), the fluid which exits the column is concentrated and dried up, and is then dissolved in ion-exchanged water. To this is added an organic solvent such as acetone or the like and after the resulting precipitate has been separated, this is concentrated and dried up and the desired sulfated alkyl oligosaccharide is obtained.

Furthermore, it is also possible, instead of adding barium hydroxide, to add an aqueous solution of sodium hydroxide, thus adjusting the pH to 9 to 10, concentrating and drying up this mixture under reduced pressure and at 40° C. or below. Adding ion-exchanged water to the residue to dissolve, yielding an aqueous solution of the resulting substance is refined by using ultrafiltration, a semipermeable membrane, a 'Maikuroashiraiza' (an electric ion-exchanging membrane manufactured by Asahi Kasei), an ion-exchanging resin column or the like to separate the inorganic salts. Methanol, acetone, or the like is added to the resulting aqueous solution, and the desired sulfated alkyl oligosaccharide sodium salt is precipitated. In the case of piperidine sulfuric acid, as well, the desired compound is obtained by an essentially identical process.

Furthermore, it is possible to use a purification method by means of gel filtration, dialysis membrane, or the like.

The following are examples of compounds according to the present invention which are expressed by formula (II) and obtained in the above manner.

sulfated hexylphenyl β-D-galactopyranosyl (1→2)-β-D-galactopyranoside, sulfated heptylphenyl β-D-galactopyranosyl (1→2)-β-D-galactopyranoside, sulfated octylphenyl β-D-galactopyranosyl (1→2)-β-D-galactopyranoside, sulfated nonylphenyl β-D-galactopyranosyl (1→2)-β-D-galactopyranoside, sulfated decylphenyl β-D-galactopyranosyl (1→2)-β-D-galactopyranoside, sulfated dodecylphenyl β-D-galactopyranosyl (1→2)-β-D-galactopyranoside, sulfated hexadecylphenyl β-D-galactopyranosyl (1→2)-β-D-galactopyranoside, sulfated octadecylphenyl β-D-galactopyranosyl (1→2)-β-D-galactopyranoside, sulfated 1,1,3,3-tetramethylbutylphenyl β-D-galactopyranosyl (1→2)-β-D-galactopyranoside, sulfated hexylphenyl β-D-galactopyranosyl (1→2)-{β-D-galactopyranosyl (1→2)}n-β-D-galactopyranoside, sulfated heptylphenyl β-D-galactopyranosyl (1→2)-{β-D-galactopyranosyl (1→2)}n-β-D-galactopyranoside, sulfated octylphenyl β-D-galactopyranosyl (1→2)-{β-D-galactopyranosyl (1→2)}n-β-D-galactopyranoside, sulfated nonylphenyl β-D-galactopyranosyl (1→2)-{β-D-galactopyranosyl (1→2)}n-β-D-galactopyranoside, sulfated decylphenyl β-D-galactopyranosyl (1→2)-{β-D-galactopyranosyl (1→2)}n-β-D-galactopyranoside, sulfated dodecylphenyl β-D-galactopyranosyl (1→2)-{β-D-galactopyranosyl (1→2)}n-β-D-galactopyranoside, sulfated hexadecylphenyl β-D-galactopyranosyl (1→2)-{β-D-galactopyranosyl (1→2)}n-β-D-galactopyranoside, sulfated octadecylphenyl β-D-galactopyranosyl (1→2)-{β-D-galactopyranosyl (1→2)}n-β-D-galactopyranoside, sulfated 1,1,3,3-tetramethylphenyl β-D-galactopyranosyl (1→2)-{β-D-galactopyranosyl (1→2)}n-β-D-galactopyranoside, In the above, n represents an integer from 1 to 18.

sulfated hexyloxyphenyl β-D-galactopyranosyl (1→2)-β-D-galactopyranoside, sulfated heptyloxyphenyl β-D-galactopyranosyl (1→2)-β-D-galactopyranoside, sulfated octyloxyphenyl β-D-galactopyranosyl (1→2)-β-D-galactopyranoside, sulfated nonyloxyphenyl β-D-galactopyranosyl (1→2)-β-D-galactopyranoside, sulfated decyloxyphenyl β-D-galactopyranosyl (1→2)-β-D-galactopyranoside, sulfated dodecyloxyphenyl β-D-galactopyranosyl (1→2)-β-D-galactopyranoside, sulfated hexadecyloxyphenyl β-D-galactopyranosyl (1→2)-β-D-galactopyranoside, sulfated octadecyloxyphenyl β-D-galactopyranosyl (1→2)-β-D-galactopyranoside, sulfated hexyloxyphenyl β-D-galactopyranosyl-(1→2)-{β-D-galactopyranosyl (1→2)}n-β-D-galactopyranoside, sulfated heptyloxyphenyl β-D-galactopyranosyl-(1→2)-{β-D-galactopyranosyl (1→2)}n-β-D-galactopyranoside, sulfated octyloxyphenyl β-D-galactopyranosyl-(1→2)-{β-D-galactopyranosyl (1→2)}n-β-D-galactopyranoside, sulfated nonyloxyphenyl β-D-galactopyranosyl-(1→2)-{β-D-galactopyranosyl (1→2)}n-β-D-galactopyranoside, sulfated decyloxyphenyl β-D-galactopyranosyl-(1→2)-{β-D-galactopyranosyl (1→2)}n-β-D-galactopyranoside, sulfated dodecyloxyphenyl β-D-galactopyranosyl-(1→2)-{β-D-galactopyranosyl (1→2)}n-β-D-galactopyranoside, sulfated hexadecyloxyphenyl β-D-galactopyranosyl-(1→2)-{β-D-galactopyranosyl (1→2)}n-β-D-galactopyranoside, sulfated octadecyloxyphenyl β-D-galactopyranosyl-(1→2)-{β-D-galactopyranosyl (1→2)}n-β-D-galactopyranoside, In the above, n represents an integer from 1 to 18.

sulfated hexylphenyl β-D-galactopyranosyl (1→3)-β-D-galactopyranoside, sulfated heptylphenyl β-D-galactopyranosyl (1→3)-β-D-galactopyranoside, sulfated octylphenyl β-D-galactopyranosyl (1→3)-β-D-galactopyranoside, sulfated nonylphenyl β-D-galactopyranosyl (1→3)-β-D-galactopyranoside, sulfated decylphenyl β-D-galactopyranosyl (1→3)-β-D-galactopyranoside, sulfated dodecylphenyl β-D-galactopyranosyl (1→3)-β-D-galactopyranoside, sulfated hexadecylphenyl β-D-galactopyranosyl (1→3)-β-D-galactopyranoside, sulfated octadecylphenyl β-D-galactopyranosyl (1→3)-β-D-galactopyranoside, sulfated 1,1,3,3-tetramethylbutylphenyl β-D-galactopyranosyl (1→3)-β-D-galactopyranoside, sulfated hexylphenyl β-D-galactopyranosyl (1→3)-{β-D-galactopyranosyl (1→3)}n-β-D-galactopyranoside, sulfated heptylphenyl β-D-galactopyranosyl (1→3)-{β-D-galactopyranosyl (1→3)}n-β-D-galactopyranoside, sulfated octylphenyl β-D-galactopyranosyl (1→3)-{β-D-galactopyranosyl (1→3)}n-β-D-galactopyranoside, sulfated nonylphenyl β-D-galactopyranosyl (1→3)-{β-D-galactopyranosyl (1→3)}n-β-D-galactopyranoside, sulfated decylphenyl β-D-galactopyranosyl (1→3)-{β-D-galactopyranosyl (1→3)}n-β-D-galactopyranoside, sulfated dodecylphenyl β-D-galactopyranosyl (1→3)-{β-D-galactopyranosyl (1→3)}n-β-D-galactopyranoside, sulfated hexadecylphenyl β-D-galactopyranosyl (1→3)-{β-D-galactopyranosyl (1→3)}n-β-D-galactopyranoside, sulfated octadecylphenyl β-D-galactopyranosyl (1→3)-{β-D-galactopyranosyl (1→3)}n-β-D-galactopyranoside, sulfated 1,1,3,3-tetramethylphenyl β-D-galactopyranosyl (1→3)-{β-D-galactopyranosyl (1→3)}n-β-D-galactopyranoside, In the above, n represents an integer from 1 to 18.

sulfated hexyloxyphenyl β-D-galactopyranosyl (1→3)-β-D-galactopyranoside, sulfated heptyloxyphenyl β-D-galactopyranosyl (1→3)-β-D-galactopyranoside, sulfated octyloxyphenyl β-D-galactopyranosyl (1→3)-β-D-galactopyranoside, sulfated nonyloxyphenyl β-D-galactopyranosyl (1→3)-β-D-galactopyranoside, sulfated decyloxyphenyl β-D-galactopyranosyl (1→3)-β-D-galactopyranoside, sulfated dodecyloxyphenyl β-D-galactopyranosyl (1→3)-β-D-galactopyranoside, sulfated hexadecyloxyphenyl β-D-galactopyranosyl (1→3)-β-D-galactopyranoside, sulfated octadecyloxyphenyl β-D-galactopyranosyl (1→3)-β-D-galactopyranoside, sulfated hexyloxyphenyl β-D-galactopyranosyl (1→3)-{β-D-galactopyranosyl (1→3)}n-β-D-galactopyranoside, sulfated heptyloxyphenyl β-D-galactopyranosyl (1→3)-{β-D-galactopyranosyl (1→3)}n-β-D-galactopyranoside, sulfated octyloxyphenyl β-D-galactopyranosyl (1→3)-{β-D-galactopyranosyl (1→3)}n-β-D-galactopyranoside, sulfated nonyloxyphenyl β-D-galactopyranosyl (1→3)-{β-D-galactopyranosyl (1→3)}n-β-D-galactopyranoside, sulfated decyloxyphenyl β-D-galactopyranosyl (1→3)-{β-D-galactopyranosyl (1→3)}n-β-D-galactopyranoside, sulfated dodecyloxyphenyl β-D-galactopyranosyl (1→3)-{β-D-galactopyranosyl (1→3)}n-β-D-galactopyranoside, sulfated hexadecyloxyphenyl β-D-galactopyranosyl (1→3)-{β-D-galactopyranosyl (1→3)}n-β-D-galactopyranoside, sulfated octadecyloxyphenyl β-D-galactopyranosyl (1→3)-{β-D-galactopyranosyl (1→3)}n-β-D-galactopyranoside, In the above, n represents an integer from 1 to 18.

sulfated hexylphenyl β-D-galactopyranosyl (1→4)-β-D-galactopyranoside, sulfated heptylphenyl β-D-galactopyranosyl (1→4)-β-D-galactopyranoside, sulfated octylphenyl β-D-galactopyranosyl (1→4)-β-D-galactopyranoside, sulfated nonylphenyl β-D-galactopyranosyl (1→4)-β-D-galactopyranoside, sulfated decylphenyl β-D-galactopyranosyl (1→4)-β-D-galactopyranoside, sulfated dodecylphenyl β-D-galactopyranosyl (1→4)-β-D-galactopyranoside,
sulfated hexadecylphenyl β-D-galactopyranosyl (1→4)-β-D-galactopyranoside,
sulfated octadecylphenyl β-D-galactopyranosyl (1→4)-β-D-galactopyranoside,
sulfated 1,1,3,3-tetramethylbutylphenyl β-D-galactopyranosyl (1→4)-β-D-galactopyranoside,
sulfated hexylphenyl β-D-galactopyranosyl (1→4)-{β-D-galactopyranosyl (1→4)}n-β-D-galactopyranoside,
sulfated heptylphenyl β-D-galactopyranosyl (1→4)-{β-D-galactopyranosyl (1→4)}n-β-D-galactopyranoside,
sulfated octylphenyl β-D-galactopyranosyl (1→4)-{β-D-galactopyranosyl (1→4)}n-β-D-galactopyranoside,
sulfated nonylphenyl β-D-galactopyranosyl (1→4)-{β-D-galactopyranosyl (1→4)}n-β-D-galactopyranoside,
sulfated decylphenyl β-D-galactopyranosyl (1→4)-{β-D-galactopyranosyl (1→4)}n-β-D-galactopyranoside,
sulfated dodecylphenyl β-D-galactopyranosyl (1→4)-{β-D-galactopyranosyl (1→4)}n-β-D-galactopyranoside,
sulfated hexadecylphenyl β-D-galactopyranosyl (1→4)-{β-D-galactopyranosyl (1→4)}n-β-D-galactopyranoside,
sulfated octadecylphenyl β-D-galactopyranosyl (1→4)-{β-D-galactopyranosyl (1→4)}n-β-D-galactopyranoside,
sulfated 1,1,3,3-tetramethylphenyl β-D-galactopyranosyl (1→4)-{β-D-galactopyranosyl (1→4)}n-β-D-galactopyranoside, In the above, n represents an integer from 1 to 18.

sulfated hexyloxyphenyl β-D-galactopyranosyl (1→4)-β-D-galactopyranoside,
sulfated heptyloxyphenyl β-D-galactopyranosyl (1→4)-β-D-galactopyranoside,
sulfated octyloxyphenyl β-D-galactopyranosyl (1→4)-β-D-galactopyranoside,
sulfated nonyloxyphenyl β-D-galactopyranosyl (1→4)-β-D-galactopyranoside,
sulfated decyloxyphenyl β-D-galactopyranosyl (1→4)-β-D-galactopyranoside,
sulfated dodecyloxyphenyl β-D-galactopyranosyl (1→4)-β-D-galactopyranoside,
sulfated hexadecyloxyphenyl β-D-galactopyranosyl (1→4)-β-D-galactopyranoside,
sulfated octadecyloxyphenyl β-D-galactopyranosyl (1→4)-β-D-galactopyranoside,
sulfated hexyloxyphenyl β-D-galactopyranosyl-(1→4)-{β-D-galactopyranosyl (1→4)}n-β-D-galactopyranoside,
sulfated heptyloxyphenyl β-D-galactopyranosyl-(1→4)-{β-D-galactopyranosyl (1→4)}n-β-D-galactopyranoside,
sulfated octyloxyphenyl β-D-galactopyranosyl-(1→4)-{β-D-galactopyranosyl (1→4)}n-β-D-galactopyranoside,
sulfated nonyloxyphenyl β-D-galactopyranosyl-(1→4)-{β-D-galactopyranosyl (1→4)}n-β-D-galactopyranoside,
sulfated decyloxyphenyl β-D-galactopyranosyl-(1→4)-{β-D-galactopyranosyl (1→4)}n-β-D-galactopyranoside,
sulfated dodecyloxyphenyl β-D-galactopyranosyl-(1→4)-{β-D-galactopyranosyl (1→4)}n-β-D-galactopyranoside,
sulfated hexadecyloxyphenyl β-D-galactopyranosyl-(1→4)-{β-D-galactopyranosyl (1→4)}n-β-D-galactopyranoside,
sulfated octadecyloxyphenyl β-D-galactopyranosyl-(1→4)-{β-D-galactopyranosyl (1→4)}n-β-D-galactopyranoside, In the above, n represents an integer from 1 to 18.

sulfated hexylphenyl β-D-galactopyranosyl (1→6)-β-D-galactopyranoside,
sulfated heptylphenyl β-D-galactopyranosyl (1→6)-β-D-galactopyranoside,
sulfated octylphenyl β-D-galactopyranosyl (1→6)-β-D-galactopyranoside,
sulfated nonylphenyl β-D-galactopyranosyl (1→6)-β-D-galactopyranoside,
sulfated decylphenyl β-D-galactopyranosyl (1→6)-β-D-galactopyranoside,
sulfated dodecylphenyl β-D-galactopyranosyl (1→6)-β-D-galactopyranoside,
sulfated hexadecylphenyl β-D-galactopyranosyl (1→6)-β-D-galactopyranoside,
sulfated octadecylphenyl β-D-galactopyranosyl (1→6)-β-D-galactopyranoside,
sulfated 1,1,3,3-tetramethylbutylphenyl β-D-galactopyranosyl (1→6)-β-D-galactopyranoside,
sulfated hexylphenyl β-D-galactopyranosyl-(1→6)-{β-D-galactopyranosyl (1→6)}n-β-D-galactopyranoside,
sulfated heptylphenyl β-D-galactopyranosyl-(1→6)-{β-D-galactopyranosyl (1→6)}n-β-D-galactopyranoside,
sulfated octylphenyl β-D-galactopyranosyl-(1→6)-{β-D-galactopyranosyl (1→6)}n-β-D-galactopyranoside,
sulfated nonylphenyl β-D-galactopyranosyl-(1→6)-{β-D-galactopyranosyl (1→6)}n-β-D-galactopyranoside,
sulfated decylphenyl β-D-galactopyranosyl-(1→6)-{β-D-galactopyranosyl (1→6)}n-β-D-galactopyranoside,
sulfated dodecylphenyl β-D-galactopyranosyl-(1→6)-{β-D-galactopyranosyl (1→6)}n-5-D-galactopyranoside,
sulfated hexadecylphenyl β-D-galactopyranosyl-(1→6)-{β-D-galactopyranosyl (1→6)}n-β-D-galactopyranoside,
sulfated octadecylphenyl β-D-galactopyranosyl-(1→6)-{β-D-galactopyranosyl (1→6)}n-β-D-galactopyranoside,
sulfated 1,1,3,3-tetramethylphenyl β-D-galactopyranosyl-(1→6)-{β-D-galactopyranosyl (1→6)}n-β-D-galactopyranoside, In the above, n represents an integer from 1 to 18.

sulfated hexyloxyphenyl β-D-galactopyranosyl (1→6)-β-D-galactopyranoside,
sulfated heptyloxyphenyl β-D-galactopyranosyl (1→6)-β-D-galactopyranoside,
sulfated octyloxyphenyl β-D-galactopyranosyl (1→6)-β-D-galactopyranoside,
sulfated nonyloxyphenyl β-D-galactopyranosyl (1→6)-β-D-galactopyranoside,
sulfated decyloxyphenyl β-D-galactopyranosyl (1→6)-β-D-galactopuranoside,
sulfated dodecyloxyphenyl β-D-galactopyranosyl (1→6)-β-D-galactopyranoside,
sulfated hexadecyloxyphenyl β-D-galactopyranosyl (1→6)-β-D-galactopyranoside,
sulfated octadecyloxyphenyl β-D-galactopyranosyl (1→6)-β-D-galactopyranoside,
sulfated hexyloxyphenyl β-D-galactopyranosyl-(1→6)-{β-D-galactopyranosyl (1→6)}n-β-D-galactopyranoside,
sulfated heptyloxyphenyl β-D-galactopyranosyl-(1→6)-{β-D-galactopyranosyl (1→6)}n-β-D-galactopyranoside,
sulfated octyloxyphenyl β-D-galactopyranosyl-(1→6)-{β-D-galactopyranosyl (1→6)}n-β-D-galactopyranoside,
sulfated nonyloxyphenyl β-D-galactopyranosyl-(1→6)-{β-D-galactopyranosyl (1→6)}n-β-D-galactopyranoside,
sulfated decyloxyphenyl β-D-galactopyranosyl-(1→6)-{β-D-galactopyranosyl (1→6) {n-β-D-galactopyranoside,
sulfated dodecyloxyphenyl β-D-galactopyranosyl-(1→6)-{β-D-galactopyranosyl (1→6)}n-β-D-galactopyranoside,
sulfated hexadecyloxyphenyl β-D-galactopyranosyl-(1→6)-{β-D-galactopyranosyl (1→6)}n-β-D-galactopyranoside,
sulfated octadecyloxyphenyl β-D-galactopyranosyl-(1→6)-{β-D-galactopyranosyl (1→6)}n-β-D-galactopyranoside, In the above, n represents an integer from 1 to 18.

sulfated hexylphenyl β-D-glucopyranosyl (1→3)-β-D-glucopyranoside, sulfated heptylphenyl β-D-glucopyranosyl (1→3)-β-D-glucopyranoside,
sulfated octylphenyl β-D-glucopyranosyl (1→3)-β-D-glucopyranoside,
sulfated nonylphenyl β-D-glucopyranosyl (1→3)-β-D-glucopyranoside,
sulfated decylphenyl β-D-glucopyranosyl (1→3)-β-D-glucopyranoside,
sulfated dodecylphenyl β-D-glucopyranosyl (1→3)-β-D-glucopyranoside,
sulfated hexadecylphenyl β-D-glucopyranosyl (1→3)-β-D-glucopyranoside,
sulfated octadecylphenyl β-D-glucopyranosyl (1→3)-β-D-glucopyranoside,
sulfated 1,1,3,3-tetramethylbutylphenyl β-D-glucopyranosyl (1→3)-β-D-glucopyranoside,
sulfated hexylphenyl β-D-glucopyranosyl-(1→3)-{β-D-glucopyranosyl (1→3)}n-β-D-glucopyranoside,
sulfated heptylphenyl β-D-glucopyranosyl-(1→3)-{β-D-glucopyranosyl (1→3)}n-β-D-glucopyranoside,
sulfated octylphenyl β-D-glucopyranosyl-(1→3)-{β-D-glucopyranosyl (1→3)}n-β-D-glucopyranoside,
sulfated nonylphenyl β-D-glucopyranosyl-(1→3)-{β-D-glucopyranosyl (1→3)}n-β-D-glucopyranoside,
sulfated decylphenyl β-D-glucopyranosyl-(1→3)-{β-D-glucopyranosyl (1→3)}n-β-D-glucopyranoside,
sulfated dodecylphenyl β-D-glucopyranosyl-(1→3)-{β-D-glucopyranosyl (1→3)}n-β-D-glucopyranoside,
sulfated hexadecylphenyl β-D-glucopyranosyl-(1→3)-{β-D-glucopyranosyl (1→3)}n-β-D-glucopyranoside,
sulfated octadecylphenyl β-D-glucopyranosyl-(1→3)-{β-D-glucopyranosyl (1→3)-n-β-D-glucopyranoside,
sulfated 1,1,3-tetramethylphenyl β-D-glucopyranosyl-(1→3)-{β-D-glucopyranosyl (1→3)}n-β-D-glucopyranoside,
In the above, n represents an integer from 1 to 18.
sulfated hexyloxyphenyl β-D-glucopyranosyl (1→3)-β-D-glucopyranoside,
sulfated heptyloxyphenyl β-D-glucopyranosyl (1→3)-β-D-glucopyranoside,
sulfated octyloxyphenyl β-D-glucopyranosyl (1→3)-β-D-glucopyranoside,
sulfated nonyloxyphenyl β-D-glucopyranosyl (1→3)-β-D-glucopyranoside,
sulfated decyloxyphenyl β-D-glucopyranosyl (1→3)-β-D-glucopyranoside,
sulfated dodecyloxyphenyl β-D-glucopyranosyl (1→3)-β-D-glucopyranoside,
sulfated hexadecyloxyphenyl β-D-glucopyranosyl (1→3)-β-D-glucopyranoside,
sulfated octadecyloxyphenyl β-D-glucopyranosyl (1→3)-β-D-glucopyranoside,
sulfated hexyloxyphenyl β-D-glucopyranosyl-(1→3)-{β-D-glucopyranosyl (1→3)}n-β-D-glucopyranoside,
sulfated heptyloxyphenyl β-D-glucopyranosyl-(1→3)-{β-D-glucopyranosyl (1→3)}n-β-D-glucopyranoside,
sulfated octyloxyphenyl β-D-glucopyranosyl-(1→3)-{β-D-glucopyranosyl (1→3)}n-β-D-glucopyranoside,
sulfated nonyloxyphenyl β-D-glucopyranosyl-(1→3)-{β-D-glucopyranosyl (1→3)}n-β-D-glucopyranoside,
sulfated decyloxyphenyl β-D-glucopyranosyl-(1→3)-{β-D-glucopyranosyl (1→3)}n-β-D-glucopyranoside,
sulfated dodecyloxyphenyl β-D-glucopyranosyl-(1→3)-{β-D-glucopyranosyl (1→3)}n-β-D-glucopyranoside,
sulfated hexadecyloxyphenyl β-D-glucopyranosyl-(1→3)-{β-D-glucopyranosyl (1→3)}n-β-D-glucopyranoside,
sulfated octadecyloxyphenyl {β-D-glucopyranosyl-(1→3)-{β-D-glucopyranosyl (1→3)}n-β-D-glucopyranoside,
In the above, n represents an integer from 1 to 18.
sulfated hexylphenyl β-D-glucopyranosyl (1→6)-β-D-glucopyranoside,
sulfated heptylphenyl β-D-glucopyranosyl (1→6)-β-D-glucopyranoside,
sulfated octylphenyl β-D-glucopyranosyl (1→6)-β-D-glucopyranoside,
sulfated nonylphenyl β-D-glucopyranosyl (1→6)-β-D-glucopyranoside,
sulfated decylphenyl β-D-glucopyranosyl (1→6)-β-D-glucopyranoside,
sulfated dodecylphenyl β-D-glucopyranosyl (1→6)-β-D-glucopyranoside,
sulfated hexadecylphenyl β-D-glucopyranosyl (1→6)-β-D-glucopyranoside,
sulfated octadecylphenyl β-D-glucopyranosyl (1→6)-β-D-glucopyranoside,
sulfated 1,1,3,3-tetramethylbutylphenyl β-D-glucopyranosyl (1→6)-β-D-glucopyranoside,
sulfated hexylphenyl β-D-glucopyranosyl-(1→6)-{β-D-glucopyranosyl (1→6)}n-β-D-glucopyranoside,
sulfated heptylphenyl β-D-glucopyranosyl-(1→6)-{β-D-glucopyranosyl (1→6)}n-β-D-glucopyranoside,
sulfated octylphenyl β-D-glucopyranosyl-(1→6)-{β-D-glucopyranosyl (1→6)}n-β-D-glucopyranoside,
sulfated nonylphenyl β-D-glucopyranosyl-(1→6)-(β-D-glucopyranosyl (1→6)}n-β-D-glucopyranoside,
sulfated decylphenyl β-D-glucopyranosyl-(1→6)-{β-D-glucopyranosyl (1→6)}n-β-D-glucopyranoside,
sulfated dodecylphenyl β-D-glucopyranosyl-(1→6)-{β-D-glucopyranosyl (1→6)}n-β-D-glucopyranoside,
sulfated hexadecylphenyl β-D-glucopyranosyl-(1→6)-{β-D-glucopyranosyl (1→6)}n-β-D-glucopyranoside,
sulfated octadecylphenyl β-D-glucopyranosyl-(1→6)-{β-D-glucopyranosyl (1→6)}n-β-D-glucopyranoside,
sulfated 1,1,3,3-tetramethylphenyl β-D-glucopyranosyl-(1→6)-{β-D-glucopyranosyl (1→6)}n-β-D-glucopyranoside,
In the above, n represents an integer from 1 to 18.
sulfated hexyloxyphenyl β-D-glucopyranosyl (1→6)-β-D-glucopyranoside,
sulfated heptyloxyphenyl β-D-glucopyranosyl (1→6)-β-D-glucopyranoside,
sulfated octyloxyphenyl β-D-glucopyranosyl (1→6)-β-D-glucopyranoside,
sulfated nonyloxyphenyl β-D-glucopyranosyl (1→6)-β-D-glucopyranoside,
sulfated decyloxyphenyl β-D-glucopyranosyl (1→6)-β-D-glucopyranoside,
sulfated dodecyloxyphenyl β-D-glucopyranosyl (1→6)-β-D-glucopyranoside,
sulfated hexadecyloxyphenyl β-D-glucopyranosyl (1→6)-β-D-glucopyranoside,
sulfated octadecyloxyphenyl β-D-glucopyranosyl (1→6)-β-D-glucopyranoside,
sulfated hexyloxyphenyl β-D-glucopyranosyl-(1→6)-{β-D-glucopyranosyl (1→6)}n-β-D-glucopyranoside,
sulfated heptyloxyphenyl β-D-glucopyranosyl-(1→6)-{β-D-glucopyranosyl (1→6)}n-β-D-glucopyranoside,
sulfated octyloxyphenyl β-D-glucopyranosyl-(1→6)-{β-D-glucopyranosyl (1→6)}n-β-D-glucopyranoside,
sulfated nonyloxyphenyl β-D-glucopyranosyl-(1→6)-{β-D-glucopyranosyl (1→6)}n-β-D-glucopyranoside,
sulfated decyloxyphenyl β-D-glucopyranosyl-(1→6)-{β-D-glucopyranosyl (1→6)}n-β-D-glucopyranoside,
sulfated dodecyloxyphenyl β-D-glucopyranosyl-(1→6)-{β-D-glucopyranosyl (1→6)}n-β-D-glucopyranoside, sulfated hexadecyloxyphenyl β-D-glucopyranosyl-(1→6)-{β-D-glucopyranosyl (1→6)}n-β-D-glucopyranoside,
sulfated octadecyloxyphenyl {β-D-glucopyranosyl-(1→6)-{β-D-glucopyranosyl (1→6)}n-β-D-glucopyranoside, In the above, n represents an integer from 1 to 18.

sulfated hexylphenyl β-D-glucopyranosyl (1→2)-β-D-glucopyranoside,
sulfated heptylphenyl β-D-glucopyranosyl (1→2)-β-D-glucopyranoside,
sulfated octylphenyl β-D-glucopyranosyl (1→2)-β-D-glucopyranoside,
sulfated nonylphenyl β-D-glucopyranosyl (1→2)-β-D-glucopyranoside,
sulfated decylphenyl β-D-glucopyranosyl (1→2)-β-D-glucopyranoside,
sulfated dodecylphenyl β-D-glucopyranosyl (1→2)-β-D-glucopyranoside,
sulfated hexadecylphenyl β-D-glucopyranosyl (1→2)-β-D-glucopyranoside,
sulfated octadecylphenyl β-D-glucopyranosyl (1→2)-β-D-glucopyranoside,
sulfated 1,1,3,3-tetramethylbutylphenyl β-D-glucopyranosyl (1→2)-β-D-glucopyranoside,
sulfated hexylphenyl [β-D-glucopyranosyl-(1→2)-{β-D-glucopyranosyl (1→2)}n-β-D-glucopyranoside,
sulfated heptylphenyl β-D-glucopyranosyl-(1→2)-{β-D-glucopyranosyl (1→2)}n-β-D-glucopyranoside,
sulfated octylphenyl β-D-glucopyranosyl-(1→2)-{β-D-glucopyranosyl (1→2)}n-β-D-glucopyranoside,
sulfated nonylphenyl β-D-glucopyranosyl-(1→2)-{β-D-glucopyranosyl (1→2)}n-β-D-glucopyranoside,
sulfated decylphenyl β-D-glucopyranosyl-(1→2)-{β-D-glucopyranosyl (1→2)}n-β-D-glucopyranoside,
sulfated dodecylphenyl β-D-glucopyranosyl-(1→2)-{β-D-glucopyranosyl (1→2)}n-β-D-glucopyranoside,
sulfated hexadecylphenyl β-D-glucopyranosyl-(1→2)-{β-D-glucopyranosyl (1→2)}n-β-D-glucopyranoside,
sulfated octadecylphenyl β-D-glucopyranosyl-(1→2)-{β-D-glucopyranosyl (1→2)}n-β-D-glucopyranoside,
sulfated 1,1,3,3-tetramethylphenyl β-D-glucopyranosyl-(1→2)-{β-D-glucopyranosyl (1→2)}n-β-D-glucopyranoside, In the above, n represents an integer from 1 to 18.

sulfated hexyloxyphenyl β-D-glucopyranosyl (1→2)-β-D-glucopyranoside,
sulfated heptyloxyphenyl β-D-glucopyranosyl (1→2)-β-D-glucopyranoside,
sulfated octyloxyphenyl β-D-glucopyranosyl (1→2)-β-D-glucopyranoside,
sulfated nonyloxyphenyl β-D-glucopyranosyl (1→2)-β-D-glucopyranoside,
sulfated decyloxyphenyl β-D-glucopyranosyl (1→2)-β-D-glucopyranoside,
sulfated dodecyloxyphenyl β-D-glucopyranosyl (1→2)-β-D-glucopyranoside,
sulfated hexadecyloxyphenyl β-D-glucopyranosyl (1→2)-β-D-glucopyranoside,
sulfated octadecyloxyphenyl β-D-glucopyranosyl (1→2)-β-D-glucopyranoside,
sulfated hexyloxyphenyl β-D-glucopyranosyl-(1→2)-{β-D-glucopyranosyl-(1→2)}n-β-D-glucopyranoside,
sulfated heptyloxyphenyl β-D-glucopyranosyl-(1→2)-{β-D-glucopyranosyl (1→2)}n-β-D-glucopyranoside,
sulfated octyloxyphenyl β-D-glucopyranosyl-(1→2)-{β-D-glucopyranosyl (1→2)}n-β-D-glucopyranoside,
sulfated nonyloxyphenyl β-D-glucopyranosyl-(1→2)-{β-D-glucopyranosyl (1→2)}n-β-D-glucopyranoside,
sulfated decyloxyphenyl β-D-glucopyranosyl-(1→2)-{β-D-glucopyranosyl (1→2)}n-β-D-glucopyranoside,
sulfated dodecyloxyphenyl β-D-glucopyranosyl-(1→2)-{β-D-glucopyranosyl (1→2)}n-β-D-glucopyranoside,
sulfated hexadecyloxyphenyl β-D-glucopyranosyl-(1→2)-{β-D-glucopyranosyl (1→2)}n-β-D-glucopyranoside,
sulfated octadecyloxyphenyl β-D-glucopyranosyl-(1→2)-{β-D-glucopyranosyl (1→2)}n-β-D-glucopyranoside, In the above, n represents an integer from 1 to 18.

sulfated hexylphenyl β-D-glucopyranosyl (1→4)-β-D-glucopyranoside,
sulfated heptylphenyl β-D-glucopyranosyl (1→4)-β-D-glucopyranoside,
sulfated octylphenyl β-D-glucopyranosyl (1→4)-β-D-glucopyranoside,
sulfated nonylphenyl β-D-glucopyranosyl (1→4)-β-D-glucopyranoside,
sulfated decylphenyl β-D-glucopyranosyl (1→4)-β-D-glucopyranoside,
sulfated dodecylphenyl β-D-glucopyranosyl (1→4)-β-D-glucopyranoside,
sulfated hexadecylphenyl β-D-glucopyranosyl (1→4)-β-D-glucopyranoside,
sulfated octadecylphenyl β-D-glucopyranosyl (1→4)-β-D-glucopyranoside,
sulfated 1,1,3,3-tetramethylbutylphenyl β-D-glucopyranosyl (1→4)-β-D-glucopyranoside,
sulfated hexylphenyl β-D-glucopyranosyl-(1→4)-{β-D-glucopyranosyl (1→4)}n-β-D-glucopyranoside,
sulfated heptylphenyl β-D-glucopyranosyl-(1→4)-{β-D-glucopyranosyl (1→4)}n-β-D-glucopyranoside,
sulfated octylphenyl β-D-glucopyranosyl-(1→4)-{β-D-glucopyranosyl (1→4)}n-β-D-glucopyranoside,
sulfated nonylphenyl β-D-glucopyranosyl-(1→4)-{β-D-glucopyranosyl (1→4)}n-β-D-glucopyranoside,
sulfated decylphenyl β-D-glucopyranosyl-(1→4)-{β-D-glucopyranosyl (1→4)}n-β-D-glucopyranoside,
sulfated dodecylphenyl β-D-glucopyranosyl-(1→4)-{β-D-glucopyranosyl (1→4)}n-β-D-glucopyranoside,
sulfated hexadecylphenyl β-D-glucopyranosyl-(1→4)-{β-D-glucopyranosyl (1→4)}n-β-D-glucopyranoside,
sulfated octadecylphenyl β-D-glucopyranosyl-(1→4)-{β-D-glucopyranosyl (1→4)}n-β-D-glucopyranoside,
sulfated 1,1,3,3-tetramethylbutylphenyl β-D-glucopyranosyl-(1→4)-{β-D-glucopyranosyl (1→4)}n-β-D-glucopyranoside, In the above, n represents an integer from 1 to 18.

sulfated hexyloxyphenyl β-D-glucopyranosyl (1→4)-β-D-glucopyranoside,
sulfated heptyloxyphenyl β-D-glucopyranosyl (1→4)-β-D-glucopyranoside,
sulfated octyloxyphenyl β-D-glucopyranosyl (1→4)-β-D-glucopyranoside,
sulfated nonyloxyphenyl β-D-glucopyranosyl (1→4)-β-D-glucopyranoside,
sulfated decyloxyphenyl β-D-glucopyranosyl (1→4)-β-D-glucopyranoside,
sulfated dodecyloxyphenyl β-D-glucopyranosyl (1→4)-β-D-glucopyranoside,
sulfated hexadecyloxyphenyl β-D-glucopyranosyl (1→4)-β-D-glucopyranoside,
sulfated octadecyloxyphenyl β-D-glucopyranosyl (1→4)-β-D-glucopyranoside,
sulfated hexyloxyphenyl β-D-glucopyranosyl-(1→4)-{β-D-glucopyranosyl (1→4)}n-β-D-glucopyranoside,
sulfated heptyloxyphenyl β-D-glucopyranosyl-(1→4)-{β-D-glucopyranosyl (1→4)}n-β-D-glucopyranoside, sulfated octyloxyphenyl β-D-glucopyranosyl-(1→4)-{β-D-glucopyranosyl (1→4)}n-β-D-glucopyranoside,
sulfated nonyloxyphenyl β-D-glucopyranosyl-(1→4)-{β-D-glucopyranosyl (1→4)}n-β-D-glucopyranoside,
sulfated decyloxyphenyl β-D-glucopyranosyl-(1→4)-{β-D-glucopyranosyl (1→4)}n-β-D-glucopyranoside,
sulfated dodecyloxyphenyl [β-D-glucopyranosyl-(1→4)-{β-D-glucopyranosyl (1→4)}n-β-D-glucopyranoside,
sulfated hexadecyloxyphenyl β-D-glucopyranosyl-(1→4)-{β-D-glucopyranosyl (1→4)}n-β-D-glucopyranoside,
sulfated octadecyloxyphenyl β-D-glucopyranosyl-(1→4)-{β-D-glucopyranosyl (1→4)}n-β-D-glucopyranoside,
In the above, n represents an integer from 1 to 18.
sulfated hexylphenyl β-D-galactopyranosyl-(1→4)-β-D-galactopyranosyl-(1→4)-β-D-glucopyranoside,
sulfated heptylphenyl β-D-galactopyranosyl-(1→4)-β-D-galactopyranosyl (1→4)-β-D-glucopyranoside,
sulfated octylphenyl β-D-galactopyranosyl-(1→4)-β-D-galactopyranosyl (1→4)-β-D-glucopyranoside,
sulfated nonylphenyl β-D-galactopyranosyl-(1→4)-β-D-galactopyranosyl (1→4)-β-D-glucopyranoside,
sulfated decylphenyl β-D-galactopyranosyl-(1→4)-β-D-galactopyranosyl (1→4)-β-D-glucopyranoside,
sulfated dodecylphenyl β-D-galactopyranosyl-(1→4)-β-D-galactopyranosyl (1→4)-β-D-glucopyranoside,
sulfated hexadecylphenyl β-D-galactopyranosyl-(1→4)-β-D-galactopyranosyl (1→4)-β-D-glucopyranoside,
sulfated octadecylphenyl β-D-galactopyranosyl-(1→4)-β-D-galactopyranosyl (1→4)-β-D-glucopyranoside,
sulfated hexylphenyl β-D-galactopyranosyl-(1→4)-{β-D-galactopyranosyl (1→4)}n-β-D-glucopyranoside,
sulfated heptylphenyl β-D-galactopyranosyl-(1→4)-{β-D-galactopyranosyl (1→4)n-β-D-glucopyranoside,
sulfated octylphenyl β-D-galactopyranosyl-(1→4)-{β-D-galactopyranosyl (1→4)}n-[β-D-glucopyranoside, sulfated nonylphenyl β-D-galactopyranosyl-(1→4)-{β-D-galactopyranosyl (1→4)}n-β-D-glucopyranoside,
sulfated decylphenyl β-D-galactopyranosyl-(1→4)-{β-D-galactopyranosyl (1→4)}n-β-D-glucopyranoside,
sulfated dodecylphenyl β-D-galactopyranosyl-(1→4)-{β-D-galactopyranosyl (1→4)}n-β-D-glucopyranoside,
sulfated hexadecylphenyl β-D-galactopyranosyl-(1→4)-{β-D-galactopyranosyl (1→4)}n-β-D-glucopyranoside,
sulfated octadecylphenyl β-D-galactopyranosyl-(1→4)-{β-D-galactopyranosyl (1→4)}n-β-D-glucopyranoside,
In the above, n represents an integer from 1 to 18.
sulfated hexyloxyphenyl β-D-galactopyranosyl-(1→4)-β-D-galactopyranosyl (1→4)-β-D-glucopyranoside,
sulfated heptyloxyphenyl β-D-galactopyranosyl-(1→4)-β-D-galactopyranosyl (1→4)-β-D-glucopyranoside,
sulfated octyloxyphenyl β-D-galactopyranosyl-(1→4)-β-D-galactopyranosyl (1→4)-β-D-glucopyranoside,
sulfated nonyloxyphenyl β-D-galactopyranosyl-(1→4)-β-D-galactopyranosyl (1→4)-β-D-glucopyranoside,
sulfated decyloxyphenyl β-D-galactopyranosyl-(1→4)-β-D-galactopyranosyl (1→4)-β-D-glucopyranoside,
sulfated dodecyloxyphenyl β-D-galactopyranosyl-(1→4)-β-D-galactopyranosyl (1→4)-β-D-glucopyranoside,
sulfated hexadecyloxyphenyl β-D-galactopyranosyl-(1→4)-β-D-galactopyranosyl (1→4)-β-D-glucopyranoside,
sulfated octadecyloxyphenyl β-D-galactopyranosyl-(1→4)-β-D-galactopyranosyl (1→4)-β-D-glucopyranoside,
sulfated hexyloxyphenyl β-D-galactopyranosyl-(1→4)-{β-D-galactopyranosyl (1→4)}n-β-D-glucopyranoside,
sulfated heptyloxyphenyl β-D-galactopyranosyl-(1→4)-{β-D-galactopyranosyl (1→4)}n-[β-D-glucopyranoside,
sulfated octyloxyphenyl [β-D-galactopyranosyl-(1→4)-{β-D-galactopyranosyl (1→4)}n-[β-D-glucopyranoside,
sulfated nonyloxyphenyl β-D-galactopyranosyl-(1→4)-{β-D-galactopyranosyl (1→4) )n-β-D-glucopyranoside,
sulfated decyloxyphenyl β-D-galactopyranosyl-(1→4)-{β-D-galactopyranosyl (1→4)}n-β-D-glucopyranoside,
sulfated dodecyloxyphenyl β-D-galactopyranosyl-(1→4)-{β-D-galactopyranosyl (1→4)}n-β-D-glucopyranoside,
sulfated hexadecyloxyphenyl β-D-galactopyranosyl-(1→4)-{β-D-galactopyranosyl (1→4)}n-β-D-glucopyranoside,
sulfated octadecyloxyphenyl β-D-galactopyranosyl-(1→4)-{β-D-galactopyranosyl (1→4)}n-β-D-glucopyranoside,
In the above, n represents an integer from 1 to 18.
sulfated hexylphenyl β-D-galactopyranosyl (1→4)-β-D-glucopyranoside,
sulfated heptylphenyl β-D-galactopyranosyl (1→4)-β-D-glucopyranoside,
sulfated octylphenyl β-D-galactopyranosyl (1→4)-β-D-glucopyranoside,
sulfated nonylphenyl β-D-galactopyranosyl (1→4)-β-D-glucopyranoside,
sulfated decylphenyl β-D-galactopyranosyl (1→4)-β-D-glucopyranoside,
sulfated dodecylphenyl β-D-galactopyranosyl (1→4)-β-D-glucopyranoside,
sulfated hexadecylphenyl β-D-galactopyranosyl (1→4)-β-D-glucopyranoside,
sulfated octadecylphenyl β-D-galactopyranosyl (1→4)-β-D-glucopyranoside,
sulfated 1,1,3,3-tetramethylphenyl β-D-galactopyranosyl (1→4)-β-D-glucopyranoside,
sulfated hexylphenyl β-D-galacuopyranosyl (1→4)-{β-D-galactopyranosyl (1→4)}n-β-D-glucopyranoside,
sulfated heptylphenyl β-D-galactopyranosyl (1→4)-{β-D-galactopyranosyl (1→4)}n-β-D-glucopyranoside,
sulfated octylphenyl β-D-galactopyranosyl (1→4)-{β-D-galactopyranosyl (1→4)}n-β-D-glucopyranoside,
sulfated nonylphenyl β-D-galactopyranosyl (1→4)-{β-D-galactopyranosyl (1→4)}n-β-D-glucopyranoside,
sulfated decylphenyl β-D-galactopyranosyl (1→4)-{β-D-galactopyranosyl (1→4)}n-β-D-glucopyranoside,
sulfated dodecylphenyl β-D-galactopyranosyl (1→4)-{β-D-galactopyranosyl (1→4)}n-β-D-glucopyranoside,
sulfated hexadecylphenyl β-D-galactopyranosyl (1→4)-{β-D-galactopyranosyl (1→4)}n-β-D-glucopyranoside,
sulfated octadecylphenyl β-D-galactopyranosyl (1→4)-{β-D-galactopyranosyl (1→4)}n-β-D-glucopyranoside,
sulfated 1,1,3,3-tetramethylphenyl β-D-galactopyranosyl (1→4){-β-D-galactopyranosyl (1→4)}n-β-D-glucopyranoside,
In the above, n represents an integer from 1 to 18.
sulfated hexyloxyphenyl β-D-galactopyranosyl (1→4)-β-D-glucopyranoside,
sulfated heptyloxyphenyl β-D-galactopyranosyl (1→4)-β-D-glucopyranoside,
sulfated octyloxyphenyl β-D-galactopyranosyl (1→4)-β-D-glucopyranoside,
sulfated nonyloxyphenyl β-D-galactopyranosyl (1→4)-β-D-glucopyranoside,
sulfated decyloxyphenyl β-D-galactopyranosyl (1→4)-β-D-glucopyranoside,
sulfated dodecyloxyphenyl β-D-galactopyranosyl (1→4)-β-D-glucopyranoside,
sulfated hexadecyloxyphenyl β-D-galactopyranosyl (1→4)-β-D-glucopyranoside,
sulfated octadecyloxyphenyl β-D-galactopyranosyl (1→4)-β-D-glucopyranoside,
sulfated hexyloxyphenyl β-D-galactopyranosyl (1→4)-{β-D-galactopyranosyl (1→4)}n-β-D-glucopyranoside, sulfated heptyloxyphenyl β-D-galactopyranosyl (1→4)-{β-D-galactopyranosyl (1→4)}n-β-D-glucopyranoside,
sulfated octyloxyphenyl β-D-galactopyranosyl (1→4)-{β-D-galactopyranosyl (1→4)}n-β-D-glucopyranoside,
sulfated nonyloxyphenyl β-D-galactopyranosyl (1→4)-{β-D-galactopyranosyl (1→4)}n-β-D-glucopyranoside,
sulfated decyloxyphenyl β-D-galactopyranosyl (1→4)-{β-D-galactopyranosyl (1→4)}n-β-D-glucopyranoside,
sulfated dodecyloxyphenyl β-D-galactopyranosyl (1→4)-{β-D-galactopyranosyl (1→4)}n-β-D-glucopyranoside,
sulfated hexadecyloxyphenyl β-D-galactopyranosyl (1→4)-{β-D-galactopyranosyl (1→4)}n-β-D-glucopyranoside,
sulfated octadecyloxyphenyl β-D-galactopyranosyl (1→4)-{β-D-galactopyranosyl (1→4)}n-β-D-glucopyranoside,
In the above, n represents an integer from 1 to 18.
sulfated hexylphenyl β-D-mannopyranosyl (1→2)-β-D-mannopyranoside,
sulfated heptylphenyl β-D-mannopyranosyl (1→2)-β-D-mannopyranoside,
sulfated octylphenyl β-D-mannopyranosyl (1→2)-β-D-mannopyranoside,
sulfated nonylphenyl β-D-mannopyranosyl (1→2)-β-D-mannopyranoside,
sulfated decylphenyl β-D-mannopyranosyl (1→2)-β-D-mannopyranoside,
sulfated dodecylphenyl β-D-mannopyranosyl (1→2)-β-D-mannopyranoside,
sulfated hexadecylphenyl β-D-mannopyranosyl (1→2)-β-D-mannopyranoside,
sulfated octadecylphenyl β-D-mannopyranosyl (1→2)-β-D-mannopyranoside,
sulfated 1,1,3,3-tetramethylbutylphenyl β-D-mannopyranosyl (1→2)-β-D-mannopyranoside,
sulfated hexylphenyl β-D-mannopyranosyl (1→2)-{β-D-mannopyranosyl (1→2)}n-β-D-mannopyranoside,
sulfated heptylphenyl β-D-mannopyranosyl (1→2)-{β-D-mannopyranosyl (1→2)}n-β-D-mannopyranoside,
sulfated octylphenyl β-D-mannopyranosyl (1→2)-{β-D-mannopyranosyl (1→2)}n-β-D-mannopyranoside,
sulfated nonylphenyl β-D-mannopyranosyl (1→2)-{β-D-mannopyranosyl (1→2)}n-β-D-mannopyranoside,
sulfated decylphenyl β-D-mannopyranosyl (1→2)-{β-D-mannopyranosyl (1→2)}n-β-D-mannopyranoside,
sulfated dodecylphenyl β-D-mannopyranosyl (1→2)-{β-D-mannopyranosyl (1→2)}n-β-D-mannopyranoside,
sulfated hexadecylphenyl β-D-mannopyranosyl (1→2)-{β-D-mannopyranosyl (1→2)}n-β-D-mannopyranoside,
sulfated octadecylphenyl β-D-mannopyranosyl (1→2)-{β-D-mannopyranosyl (1→2)}n-β-D-mannopyranoside,
sulfated 1,1,3,3-tetramethylphenyl β-D-mannopyranosyl (1→2)-{β-D-mannopyranosyl (1→2)}n-β-D-mannopyranoside,
In the above, n represents an integer from 1 to 18.
sulfated hexyloxyphenyl β-D-mannopyranosyl (1→2)-β-D-mannopyranoside,
sulfated heptyloxyphenyl β-D-mannopyranosyl (1→2)-β-D-mannopyranoside,
sulfated octyloxyphenyl β-D-mannopyranosyl (1→2)-β-D-mannopyranoside,
sulfated nonyloxyphenyl β-D-mannopyranosyl (1→2)-β-D-mannopyranoside,
sulfated decyloxyphenyl β-D-mannopyranosyl (1→2)-β-D-mannopyranoside,
sulfated dodecyloxyphenyl β-D-mannopyranosyl (1→2)-β-D-mannopyranos
sulfated hexadecyloxyphenyl β-D-mannopyranosyl (1→2)-β-D-mannopyranoside,
sulfated octadecyloxyphenyl β-D-mannopyranosyl (1→2)-β-D-mannopyranoside,
sulfated hexyloxyphenyl β-D-mannopyranosyl (1→2)-{β-D-mannopyranosyl (1→2)}n-β-D-mannopyranoside,
sulfated heptyloxyphenyl β-D-mannopyranosyl (1→2)-{β-D-mannopyranosyl (1→2)n-β-D-mannopyranoside,
sulfated octyloxyphenyl β-D-mannopyranosyl (1→2)-{β-D-mannopyranosyl (1→2)}n-β-D-mannopyranoside,
sulfated nonyloxyphenyl β-D-mannopyranosyl (1→2)-(β-D-mannopyranosyl (1→2)}n-β-D-mannopyranoside,
sulfated decyloxyphenyl β-D-mannopyranosyl (1→2)-{β-D-mannopyranosyl (1→2)}n-β-D-mannopyranoside,
sulfated dodecyloxyphenyl β-D -mannopyranosyl (1→2)-{β-D-mannopyranosyl (1→2)}n-β-D-mannopyranoside,
sulfated hexadecyloxyphenyl β-D-mannopyranosyl (1→2)-{β-D-mannopyranosyl (1→2)}n-β-D-mannopyranoside,
sulfated octadecyloxyphenyl β-D-mannopyranosyl (1→2)-{β-D-mannopyranosyl (1→2)}n-β-D-mannopyranoside,
In the above, n represents an integer from 1 to 18.
sulfated hexylphenyl β-D-mannopyranosyl (1→3)-β-D-mannopyranoside,
sulfated heptylphenyl β-D-mannopyranosyl (1→3)-β-D-mannopyranoside,
sulfated octylphenyl β-D-mannopyranosyl (1→3)-β-D-mannopyranoside,
sulfated nonylphenyl β-D-mannopyranosyl (1→3)-β-D-mannopyranoside,
sulfated decylphenyl β-D-mannopyranosyl (1→3)-β-D-mannopyranoside,
sulfated dodecylphenyl β-D-mannopyranosyl (1→3)-β-D-mannopyranoside,
sulfated hexadecylphenyl β-D-mannopyranosyl (1→3)-β-D-mannopyranoside,
sulfated octadecylphenyl β-D-mannopyranosyl (1→3)-β-D-mannopyranoside,
sulfated 1,1,3,3-tetramethylbutylphenyl β-D-mannopyranosyl (1→3)-β-D-mannopyranoside,
sulfated hexylphenyl β-D-mannopyranosyl (1→3)-{β-D-mannopyranosyl (1→3)}n-β-D-mannopyranoside,
sulfated heptylphenyl β-D-mannopyranosyl (1→3)-{β-D-mannopyranosyl (1-)3)}n-β-D-mannopyranoside,
sulfated octylphenyl β-D-mannopyranosyl (1→3)-{β-D-mannopyranosyl (1→3)}n-β-D-mannopyranoside,
sulfated nonylphenyl β-D-mannopyranosyl (1→3)-{β-D-mannopyranosyl (1→3)}n-β-D-mannopyranoside,
sulfated decylphenyl β-D-mannopyranosyl (1→3)-{β-D-mannopyranosyl (1→3)}n-β-D-mannopyranoside,
sulfated dodecylphenyl β-D-mannopyranosyl (1→3)-{β-D-mannopyranosyl (1→3)}n-β-D-mannopyranoside,
sulfated hexadecylphenyl β-D-mannopyranosyl (1→3)-{β-D-mannopyranosyl (1→3)}n-β-D-mannopyranoside,
sulfated octadecylphenyl β-D-mannopyranosyl (1→3)-{β-D-mannopyranosyl (1→3)}n-β-D-mannopyranoside,
sulfated 1,1,3,3-tetramethylphenyl β-D-mannopyranosyl (1→3)-{-β-D-mannopyranos yl (1→3)}n-β-D-mannopyranoside,
In the above, n represents an integer from 1 to 18.
sulfated hexyloxyphenyl β-D-mannopyranosyl (1→3)-β-D-mannopyranoside,
sulfated heptyloxyphenyl β-D-mannopyranosyl (1→3)-β-D-mannopyranoside,
sulfated octyloxyphenyl β-D-mannopyranosyl (1→3)-β-D-mannopyranoside,
sulfated nonyloxyphenyl β-D-mannopyranosyl (1→3)-β-D-mannopyranoside,
sulfated decyloxyphenyl β-D-mannopyranosyl (1→3)-β-D-mannopyranoside, sulfated dodecyloxyphenyl β-D-mannopyranosyl (1→3)-β-D-mannopyranoside,
sulfated hexadecyloxyphenyl β-D-mannopyranosyl (1→3)-β-D-mannopyranoside,
sulfated octadecyloxyphenyl β-D-mannopyranosyl (1→3)-β-D-mannopyranoside,
sulfated hexyloxyphenyl β-D-mannopyranosyl (1→3)-{β-D-mannopyranosyl (1→3)}n-β-D-mannopyranoside,
sulfated heptyloxyphenyl β-D-mannopyranosyl (1→3)-{β-D-mannopyranosyl (1→3)}n-β-D-mannopyranoside,
sulfated octyloxyphenyl β-D-mannopyranosyl (1→3)-{β-D-mannopyranosyl (1→3)}n-β-D-mannopyranoside,
sulfated nonyloxyphenyl β-D-mannopyranosyl (1→3)-{β-D-mannopyranosyl (1→3)}n-β-D-mannopyranoside,
sulfated decyloxyphenyl β-D-mannopyranosyl (1→3)-{β-D-mannopyranosyl (1→3)}n-β-D-mannopyranoside,
sulfated dodecyloxyphenyl β-D-mannopyranosyl (1→3)-{β-D-mannopyranosyl (1→3)}n-β-D-mannopyranoside,
sulfated hexadecyloxyphenyl β-D-mannopyranosyl (1→3)-{β-D-mannopyranosyl (1→3)}n-β-D-mannopyranoside,
sulfated octadecyloxyphenyl β-D-mannopyranosyl (1→3)-{β-D-mannopyranosyl (1→3)}n-β-D-mannopyranoside,
sulfated hexylphenyl β-D-mannopyranosyl (1→4)-β-D-mannopyranoside,
sulfated heptylphenyl β-D-mannopyranosyl (1→4)-β-D-mannopyranoside,
sulfated octylphenyl β-D-mannopyranosyl (1→4)-β-D-mannopyranoside,
sulfated nonylphenyl β-D-mannopyranosyl (1→4)-β-D-mannopyranoside,
sulfated decylphenyl β-D-mannopyranosyl (1->4)-β-D-mannopyranoside,
sulfated dodecylphenyl β-D-mannopyranosyl (1->4)-β-D-mannopyranoside,
sulfated hexadecylphenyl β-D-mannopyranosyl (1→4)-β-D-mannopyranoside,
sulfated octadecylphenyl β-D-mannopyranosyl (1→4)-β-D-mannopyranoside,
sulfated 1,1,3,3-tetramethylbutylphenyl β-D-mannopyranosyl (1→4)-β-D-mannopyranoside,
sulfated hexylphenyl β-D-mannopyranosyl (1→4)-{β-D-mannopyranosyl (1→4)}n-β-D-mannopyranoside,
sulfated heptylphenyl β-D-mannopyranosyl (1→4)-{β-D-mannopyranosyl (1→4)}n-β-D-mannopyranoside,
sulfated octylphenyl β-D-mannopyranosyl (1→4)-{β-D-mannopyranosyl (1→4)}n-β-D-mannopyranoside,
sulfated nonylphenyl β-D-mannopyranosyl (1→4)-{β-D-mannopyranosyl (1→4)}n-β-D-mannopyranoside,
sulfated decylphenyl β-D-mannopyranosyl (1→4)-{β-D-mannopyranosyl (1→4)}n-β-D-mannopyranoside,
sulfated dodecylphenyl β-D-mannopyranosyl (1→4)-{β-D-mannopyranosyl (1→4)}n-β-D-mannopyranoside,
sulfated hexadecylphenyl β-D-mannopyranosyl (1→4)-{β-D-mannopyranosyl (1→4)}n-β-D-mannopyranoside,
sulfated octadecylphenyl β-D-mannopyranosyl (1→4)-{β-D-mannopyranosyl (1→4)}n-β-D-mannopyranoside,
sulfated 1,1,3,3-tetramethylphenyl β-D-mannopyranosyl (1→4)-{β-D-mannopyranosyl (1→4)}n-β-D-mannopyranoside, In the above, n represents an integer from 1 to 18.

sulfated hexyloxyphenyl β-D-mannopyranosyl (1→4)-β-D-mannopyranoside,
sulfated heptyloxyphenyl β-D-mannopyranosyl (1→4)-β-D-mannopyranoside,
sulfated octyloxyphenyl β-D-mannopyranosyl (1→4)-β-D-mannopyranoside,
sulfated nonyloxyphenyl β-D-mannopyranosyl (1→4)-β-D-mannopyranoside,
sulfated decyloxyphenyl β-D-mannopyranosyl (1→4)-β-D-mannopyranoside,
sulfated dodecyloxyphenyl β-D-mannopyranosyl (1→4)-β-D-mannopyranoside,
sulfated hexadecyloxyphenyl β-D-mannopyranosyl (1→4)-β-D-mannopyranoside,
sulfated octadecyloxyphenyl β-D-mannopyranosyl (1→4)-β-D-mannopyranoside,
sulfated hexyloxyphenyl β-D-mannopyranosyl (1→4)-{β-D-mannopyranosyl (1→4)}n-β-D-mannopyranoside,
sulfated heptyloxyphenyl β-D-mannopyranosyl (1→4)-{β-D-mannopyranosyl (1→4)}n-β-D-mannopyranoside,
sulfated octyloxyphenyl β-D-mannopyranosyl (1→4)-{β-D-mannopyranosyl (1→4)}n-β-D-mannopyranoside,
sulfated nonyloxyphenyl β-D-mannopyranosyl (1→4)-{β-D-mannopyranosyl (1→4)}n-β-D-mannopyranoside,
sulfated decyloxyphenyl β-D-mannopyranosyl (1→4)-{β-D-mannopyranosyl (1→4)}n-β-D-mannopyranoside,
sulfated dodecyloxyphenyl β-D-mannopyranosyl (1→4)-{β-D-mannopyranosyl (1→4)}n-β-D-mannopyranoside,
sulfated hexadecyloxyphenyl β-D-mannopyranosyl (1→4)-{β-D-mannopyranosyl (1→4)}n-β-D-mannopyranoside,
sulfated octadecyloxyphenyl β-D-mannopyranosyl (1→4)-{β-D-mannopyranosyl (1→4)}n-β-D-mannopyranoside,
sulfated hexylphenyl β-D-mannopyranosyl (1→6)-β-D-mannopyranoside,
sulfated heptylphenyl β-D-mannopyranosyl (1→6)-β-D-mannopyranoside,
sulfated octylphenyl β-D-mannopyranosyl (1→6)-β-D-mannopyranoside,
sulfated nonylphenyl β-D-mannopyranosyl (1→6)-β-D-mannopyranoside,
sulfated decylphenyl β-D-mannopyranosyl (1→6)-β-D-mannopyranoside,
sulfated dodecylphenyl β-D-mannopyranosyl (1→6)-β-D-mannopyranoside,
sulfated hexadecylphenyl β-D-mannopyranosyl (1→6)-β-D-mannopyranoside,
sulfated octadecylphenyl β-D-mannopyranosyl (1→6)-β-D-mannopyranoside,
sulfated 1,1,3,3-tetramethylbutylphenyl β-D-mannopyranosyl (1→6)-β-D-mannopyranoside,
sulfated hexylphenyl β-D-mannopyranosyl (1-)6)-{β-D-mannopyranosyl (1→6)}n-β-D-mannopyranoside,
sulfated heptylphenyl β-D-mannopyranosyl (1→6)-{β-D-mannopyranosyl (1→6)}n-β-D-mannopyranoside,
sulfated octylphenyl β-D-mannopyranosyl (1→6)-{β-D-mannopyranosyl (1→6)}n-β-D-mannopyranoside,
sulfated nonylphenyl β-D-mannopyranosyl (1→6)-{β-D-mannopyranosyl (1→6)}n-β-D-mannopyranoside,
sulfated decylphenyl β-D-mannopyranosyl (1→6)-{β-D-mannopyranosyl (1→6)}n-β-D-mannopyranoside,
sulfated dodecylphenyl β-D-mannopyranosyl (1→6)-{β-D-mannopyranosyl (1→6)}n-β-D-mannopyranoside,
sulfated hexadecylphenyl {5-D-mannopyranosyl (1→6)-{β-D-mannopyranosyl (1→6)}n-β-D-mannopyranoside,
sulfated octadecylphenyl β-D-mannopyranosyl (1→6)-{β-D-mannopyranosyl (1→6)}n-β-D-mannopyranoside,
sulfated 1,1,3,3-tetramethylphenyl β-D-mannopyranosyl (1→6)-{β-D-mannopyranosyl (1→6)}n-β-D-mannopyranoside, In the above, n represents an integer from 1 to 18.

sulfated hexyloxyphenyl β-D-mannopyranosyl (1→6)-β-D-mannopyranoside,
sulfated heptyloxyphenyl β-D-mannopyranosyl (1→6)-β-D-mannopyranoside,
sulfated octyloxyphenyl β-D-mannopyranosyl (1→6)-β-D-mannopyranoside, sulfated nonyloxyphenyl β-D-mannopyranosyl (1→6)-β-D-mannopyranoside,
sulfated decyloxyphenyl i5-D-mannopyranosyl (1→6)-β-D-mannopyranoside,
sulfated dodecyloxyphenyl β-D-mannopyranosyl (1→6)-β-D-mannopyranoside,
sulfated hexadecyloxyphenyl β-D-mannopyranosyl(1→6)-β-D-mannopyranoside,
sulfated octadecyloxyphenyl β-D-mannopyranosyl (1→6)-β-D-mannopyranoside,
sulfated hexyloxyphenyl β-D-mannopyranosyl (1→6)-{β-D-mannopyranosyl (1→6)}n-β-D-mannopyranoside,
sulfated heptyloxyphenyl β-D-mannopyranosyl (1→6)-{β-D-mannopyranosyl (1→6)}n-β-D-mannopyranoside,
sulfated octyloxyphenyl β-D-mannopyranosyl (1→6)-{β-D-mannopyranosyl (1→6)}n-β-D-mannopyranoside,
sulfated nonyloxyphenyl β-D-mannopyranosyl (1→6)-{β-D-mannopyranosyl (1→6)}n-β-D-mannopyranoside,
sulfated decyloxyphenyl β-D-mannopyranosyl (1→6)-{β-D-mannopyranosyl (1→6)}n-β-D-mannopyranoside,
sulfated dodecyloxyphenyl β-D-mannopyranosyl (1→6)-{β-D-mannopyranosyl (1→6)}n-β-D-mannopyranoside,
sulfated hexadecyloxyphenyl β-D-mannopyranosyl (1→6)-{β-D-mannopyranosyl (1→6)}n-β-D-mannopyranoside,
sulfated octadecyloxyphenyl β-D-mannopyranosyl (1→6)-{β-D-mannopyranosyl (1→6)}n-β-D-mannopyranoside, In the above, n represents an integer from 1 to 18.

In the above examples, the bonds of the sugar chains are shown as β-type bonds; however, there are of course also α-type bonds, and it would also be possible to show compounds in which the above β-type bonds have been replaced by α-type bonds. In the same way, there are also two types of bonding form of the glycosides, an α-type form and a β-type form. Furthermore, this is also possible in the case of D isomers and L isomers, so that each example compound shown here represents 8 different types of compounds.

Furthermore, examples of the compound of the present invention represented by the formula (III) are given below.
hexylphenyl β-D-galactopyranosyl (1→2)-β-D-galactopyranoside,
heptylphenyl β-D-galactopyranosyl (1→2)-β-D-galactopyranoside,
octylphenyl β-D-galactopyranosyl (1→2)-β-D-galactopyranoside,
nonylphenyl β-D-galactopyranosyl (1→2)-β-D-galactopyranoside,
decylphenyl β-D-galactopyranosyl (1→2)-β-D-galactopyranoside,
dodecylphenyl β-D-galactopyranosyl (1→2)-β-D-galactopyranoside,
hexadecylphenyl β-D-galactopyranosyl (1→2)-β-D-galactopyranoside,
octadecylphenyl β-D-galactopyranosyl (1→2)-β-D-galactopyranoside,
1,1,3,3-tetramethylbutylphenyl β-D-galactopyranosyl (1→2)-β-D-galactopyranoside,
hexylphenyl β-D-galactopyranosyl (1→2)-{β-D-galactopyranosyl (1→2)}n-β-D-galactopyranoside,
heptylphenyl β-D-galactopyranosyl (1→2)-{β-D-galactopyranosyl (1→2)}n-β-D-galactopyranoside,
octylphenyl β-D-galactopyranosyl (1→2)-{β-D-galactopyranosyl (1→2)}n-β-D-galactopyranoside,
nonylphenyl β-D-galactopyranosyl (1→2)-{β-D-galactopyranosyl (1→2)}n-β-D-galactopyranoside,
decylphenyl β-D-galactopyranosyl (1→2)-{β-D-galactopyranosyl (1→2)}n-β-D-galactopyranoside,
dodecylphenyl β-D-galactopyranosyl (1→2)-{β-D-galactopyranosyl (1→2)}n-β-D-galactopyranoside,
hexadecylphenyl β-D-galactopyranosyl (1→2)-{β-D-galactopyranosyl (1→2)}n-β-D-galactopyranoside,
octadecylphenyl β-D-galactopyranosyl (1→2)-{β-D-galactopyranosyl (1→2)}n-β-D-galactopyranoside,
1,1,3,3-tetramethylphenyl β-D-galactopyranosyl (1→2)-{β-D-galactopyranosyl (1→2)}n-β-D-galactopyranoside, In the above, n represents an integer from 1 to 18.
hexyloxyphenyl β-D-galactopyranosyl (1→2)-β-D-galactopyranoside,
heptyloxyphenyl β-D-galactopyranosyl (1→2)-β-D-galactopyranoside,
octyloxyphenyl β-D-galactopyranosyl (1→2)-β-D-galactopyranoside,
nonyloxyphenyl β-D-galactopyranosyl (1→2)-β-D-galactopyranoside,
decyloxyphenyl β-D-galactopyranosyl (1→2)-β-D-galactopyranoside,
dodecyloxyphenyl β-D-galactopyranosyl (1→2)-β-D-galactopyranoside,
hexadecyloxyphenyl β-D-galactopyranosyl (1→2)-β-D-galactopyranoside,
octadecyloxyphenyl β-D-galactopyranosyl (1→2)-β-D-galactopyranoside,
hexyloxyphenyl β-D-galactopyranosyl (1→2)-{β-D-galactopyranosyl (1→2)}n-β-D-galactopyranoside,
heptyloxyphenyl β-D-galactopyranosyl (1→2)-{β-D-galactopyranosyl (1→2)}n-β-D-galactopyranoside,
octyloxyphenyl β-D-galactopyranosyl (1→2)-{β-D-galactopyranosyl (1→2)}n-β-D-galactopyranoside,
nonyloxyphenyl β-D-galactopyranosyl (1→2)-{β-D-galactopyranosyl (1→2)}n-β-D-galactopyranoside,
decyloxyphenyl β-D-galactopyranosyl (1→2)-{β-D-galactopyranosyl (1→2)}n-β-D-galactopyranoside,
dodecyloxyphenyl β-D-galactopyranosyl (1→2)-{β-D-galactopyranosyl (1→2)}n-β-D-galactopyranoside,
hexadecyloxyphenyl β-D-galactopyranosyl (1→2)-{β-D-galactopyranosyl (1→2)}n-β-D-galactopyranoside,
octadecyloxyphenyl β-D-galactopyranosyl (1→2)-{β-D-galactopyranosyl (1→2)}n-β-D-galactopyranoside,
hexylphenyl β-D-galactopyranosyl (1→3)-β-D-galactopyranoside,
heptylphenyl β-D-galactopyranosyl (1→3)-β-D-galactopyranoside,
octylphenyl β-D-galactopyranosyl (1→3)-β-D-galactopyranoside,
nonylphenyl β-D-galactopyranosyl (1→3)-{β-D-galactopyranoside,
decylphenyl β-D-galactopyranosyl (1→3)-β-D-galactopyranoside,
dodecylphenyl β-D-galactopyranosyl (1→3)-β-D-galactopyranoside,
hexadecylphenyl β-D-galactopyranosyl (1→3)-β-D-galactopyranoside,
octadecylphenyl β-D-galactopyranosyl (1→3)-β-D-galactopyranoside,
1,1,3,3-tetramethylbutylphenyl β-D-galactopyranosyl (1→3)-β-D-galactopyranoside,
hexylphenyl β-D-galactopyranosyl (1→3)-{β-D-galactopyranosyl (1→3)}n-β-D-galactopyranoside,
heptylphenyl β-D-galactopyranosyl (1→3)-{β-D-galactopyranosyl (1→3)}n-β-D-galactopyranoside,
octylphenyl β-D-galactopyranosyl (1→3)-{β-D-galactopyranosyl (1→3)}n-β-D-galactopyranoside,
nonylphenyl β-D-galactopyranosyl (1→3)-{β-D-galactopyranosyl (1→3)}n-β-D-galactopyranoside,
decylphenyl β-D-galactopyranosyl (1→3)-{β-D-galactopyranosyl (1→3)}n-β-D-galactopyranoside, dodecylphenyl β-D-galactopyranosyl (1→3)-{β-D-galactopyranosyl (1→3)}n-β-D-galactopyranoside,
hexadecylphenyl β-D-galactopyranosyl (1→3)-{β-D-galactopyranosyl (1→3)}n-β-D-galactopyranoside,
octadecylphenyl β-D-galactopyranosyl (1→3)-{β-D-galactopyranosyl (1→3)}n-{β-D-galactopyranoside,
1,1,3,3-tetramethylphenyl β-D-galactopyranosyl (1→3)-{β-D-galactopyranosyl (1→3)}n-β-D-galactopyranoside,
In the above, n represents an integer from 1 to 18.
hexyloxyphenyl β-D-galactopyranosyl (1→3)-β-D-galactopyranoside,
heptyloxyphenyl β-D-galactopyranosyl (1→3)-β-D-galactopyranoside,
octyloxyphenyl β-D-galactopyranosyl (1→3)-β-D-galactopyranoside,
nonyloxyphenyl β-D-galactopyranosyl (1→3)-β-D-galactopyranoside,
decyloxyphenyl β-D-galactopyranosyl (1→3)-β-D-galactopyranoside,
dodecyloxyphenyl β-D-galactopyranosyl (1→3)-β-D-galactopyranoside,
hexadecyloxyphenyl β-D-galactopyranosyl (1→3)-β-D-galactopyranoside,
octadecyloxyphenyl β-D-galactopyranosyl (1→3)-β-D-galactopyranoside,
hexyloxyphenyl β-D-galactopyranosyl (1→3)-{β-D-galactopyranosyl (1→3)}n-β-D-galactopyranoside,
heptyloxyphenyl β-D-galactopyranosyl (1→3)-{β-D-galactopyranosyl (1→3)}n-β-D-galactopyranoside,
octyloxyphenyl β-D-galactopyranosyl (1→3)-{β-D-galactopyranosyl (1→3)}n-β-D-galactopyranoside,
nonyloxyphenyl β-D-galactopyranosyl (1→3)-{β-D-galactopyranosyl (1→3)}n-β-D-galactopyranoside,
decyloxyphenyl β-D-galactopyranosyl (1→3)-{β-D-galactopyranosyl (1→3)}n-β-D-galactopyranoside,
dodecyloxyphenyl β-D-galactopyranosyl (1→3)-{β-D-galactopyranosyl (1→3)}n-β-D-galactopyranoside,
hexadecyloxyphenyl β-D-galactopyranosyl (1→3)-{β-D-galactopyranosyl (1→3)}n-β-D-galactopyranoside,
octadecyloxyphenyl β-D-galactopyranosyl (1→3)-{β-D-galactopyranosyl (1→3)}n-β-D-galactopyranoside,
In the above, n represents an integer from 1 to 18.
hexylphenyl β-D-galactopyranosyl (1→4)-β-D-galactopyranoside,
heptylphenyl β-D-galactopyranosyl (1→4)-β-D-galactopyranoside,
octylphenyl β-D-galactopyranosyl (1→4)-β-D-galactopyranoside,
nonylphenyl β-D-galactopyranosyl (1→4)-β-D-galactopyranoside,
decylphenyl β-D-galactopyranosyl (1→4)-β-D-galactopyranoside,
dodecylphenyl β-D-galactopyranosyl (1→4)-β-D-galactopyranoside,
hexadecylphenyl β-D-galactopyranosyl (1→4)-β-D-galactopyranoside,
octadecylphenyl β-D-galactopyranosyl (1→4)-β-D-galactopyranoside,
1,1,3,3-tetramethylbutylphenyl β-D-galactopyranosyl (1→4)-β-D-galactopyranoside,
hexylphenyl β-D-galactopyranosyl (1→4)-{β-D-galactopyranosyl (1→4)}n-β-D-galactopyranoside,
heptylphenyl β-D-galactopyranosyl (1→4)-{β-D-galactopyranosyl (1→4)}n-β-D-galactopyranoside,
octylphenyl β-D-galactopyranosyl (1→4)-{β-D-galactopyranosyl (1→4)}n-β-D-galactopyranoside,
nonylphenyl β-D-galactopyranosyl (1→4)-{β-D-galactopyranosyl (1→4)}n-β-D-galactopyranoside,
decylphenyl β-D-galactopyranosyl (1→4)-{β-D-galactopyranosyl (1→4)}n-β-D-galactopyranoside,
dodecylphenyl β-D-galactopyranosyl (1→4)-{β-D-galactopyranosyl (1→4)}n-β-D-galactopyranoside,
hexadecylphenyl β-D-galactopyranosyl (1→4)-{β-D-galactopyranosyl (1→4)}n-β-D-galactopyranoside,
octadecylphenyl β-D-galactopyranosyl (1→4)-{β-D-galactopyranosyl (1→4)}n-β-D-galactopyranoside,
1,1,3,3-tetramethylphenyl β-D-galactopyranosyl (1→4)-{β-D-galactopyranosyl (1→4)}n-β-D-galactopyranoside,
In the above, n represents an integer from 1 to 18.
hexyloxyphenyl β-D-galactopyranosyl (1→4)-β-D-galactopyranoside,
heptyloxyphenyl β-D-galactopyranosyl (1→4)-β-D-galactopyranoside,
octyloxyphenyl β-D-galactopyranosyl (1→4)-β-D-galactopyranoside,
nonyloxyphenyl β-D-galactopyranosyl (1→4)-β-D-galactopyranoside,
decyloxyphenyl β-D-galactopyranosyl (1→4)-β-D-galactopyranoside,
dodecyloxyphenyl β-D-galactopyranosyl (1→4)-β-D-galactopyranoside,
hexadecyloxyphenyl β-D-galactopyranosyl (1→4)-β-D-galactopyranoside,
octadecyloxyphenyl β-D-galactopyranosyl (1→4)-β-D-galactopyranoside,
hexyloxyphenyl β-D-galactopyranosyl (1→4)-{β-D-galactopyranosyl (1→4)}n-β-D-galactopyranoside,
heptyloxyphenyl β-D-galactopyranosyl (1→4)-{β-D-galactopyranosyl (1→4)}n-β-D-galactopyranoside,
octyloxyphenyl β-D-galactopyranosyl (1→4)-{β-D-galactopyranosyl (1→4)n-β-D-galactopyranoside,
nonyloxyphenyl β-D-galactopyranosyl (1→4)-{β-D-galactopyranosyl (1→4)}n-β-D-galactopyranoside,
decyloxyphenyl β-D-galactopyranosyl (1→4)-{β-D-galactopyranosyl (1→4)}n-β-D-galactopyranoside,
dodecyloxyphenyl β-D-galactopyranosyl (1→4)-{β-D-galactopyranosyl (1→4)n-β-D-galactopyranoside,
hexadecyloxyphenyl β-D-galactopyranosyl (1→4)-{β-D-galactopyranosyl (1→4)}n-β-D-galactopyranoside,
octadecyloxyphenyl β-D-galactopyranosyl (1→4)-{β-D-galactopyranosyl (1→4)}n-β-D-galactopyranoside,
In the above, n represents an integer from 1 to 18.
hexylphenyl β-D-galactopyranosyl (1→6)-β-D-galactopyranoside,
heptylphenyl β-D-galactopyranosyl (1→6)-β-D-galactopyranoside,
octylphenyl β-D-galactopyranosyl (1→6)-β-D-galactopyranoside,
nonylphenyl β-D-galactopyranosyl (1→6)-β-D-galactopyranoside,
decylphenyl β-D-galactopyranosyl (1→6)-β-D-galactopyranoside,
dodecylphenyl β-D-galactopyranosyl (1→6)-β-D-galactopyranoside,
hexadecylphenyl β-D-galactopyranosyl (1→6)-β-D-galactopyranoside,
octadecylphenyl β-D-galactopyranosyl (1→6)-β-D-galactopyranoside,
1,1,3,3-tetramethylbutylphenyl β-D-galactopyranosyl (1→6)-β-D-galactopyranoside,
hexylphenyl β-D-galactopyranosyl (1→6)-{β-D-galactopyranosyl (1→6)}n-β-D-galactopyranoside,
heptylphenyl β-D-galactopyranosyl (1→6)-{β-D-galactopyranosyl (1→6)}n-β-D-galactopyranoside,
octylphenyl β-D-galactopyranosyl (1→6)-{β-D-galactopyranosyl (1→6)}n-β-D-galactopyranoside, nonylphenyl β-D-galactopyranosyl (1→6)-{β-D-galactopyranosyl (1→6)}n-β-D-galactopyranoside,
decylphenyl β-D-galactopyranosyl (1→6)-{β-D-galactopyranosyl (1→6)}n-β-D-galactopyranoside,
dodecylphenyl β-D-galactopyranosyl (1→6)-{β-D-galactopyranosyl (1→6)}n-β-D-galactopyranoside,
hexadecylphenyl β-D-galactopyranosyl (1→6)-{β-D-galactopyranosyl (1→6)}n-β-D-galactopyranoside,
octadecylphenyl β-D-galactopyranosyl (1→6)-{β-D-galactopyranosyl (1→6)n-β-D-galactopyranoside,
1,1,3,3-tetramethylphenyl β-D-galactopyranosyl (1→6)-{β-D-galactopyranosyl (1→6)}n-β-D-galactopyranoside,
In the above, n represents an integer from 1 to 18.
hexyloxyphenyl β-D-galactopyranosyl (1→6)-β-D-galactopyranoside,
heptyloxyphenyl β-D-galactopyranosyl (1→6)-β-D-galactopyranoside,
octyloxyphenyl β-D-galactopyranosyl (1→6)-β-D-galactopyranoside,
nonyloxyphenyl β-D-galactopyranosyl (1→6)-β-D-galactopyranoside,
decyloxyphenyl β-D-galactopyranosyl (1→6)-β-D-galactopyranoside,
dodecyloxyphenyl β-D-galactopyranosyl (1→6)-β-D-galactopyranoside,
hexadecyloxyphenyl β-D-galactopyranosyl (1→6)-β-D-galactopyranoside,
octadecyloxyphenyl β-D-galactopyranosyl (1→6)-β-D-galactopyranoside,
hexyloxyphenyl β-D-galactopyranosyl (1→6)-{β-D-galactopyranosyl (1→6)}n-β-D-galactopyranoside,
heptyloxyphenyl β-D-galactopyranosyl (1→6)-{β-D-galactopyranosyl (1→6)}n-β-D-galactopyranoside,
octyloxyphenyl β-D-galactopyranosyl (1→6)-{β-D-galactopyranosyl (1→6)}n-β-D-galactopyranoside,
nonyloxyphenyl β- D-galactopyranosyl (1→6)-{β-D-galactopyranosyl (1→6)}n-β-D-galactopyranoside,
decyloxyphenyl β-D-galactopyranosyl (1→6)-{β-D-galactopyranosyl (1→6)}n-β-D-galactopyranoside,
dodecyloxyphenyl β-D-galactopyranosyl (1→6)-{β-D-galactopyranosyl (1→6)}n-β-D-galactopyranoside,
hexadecyloxyphenyl β-D-galactopyranosyl (1→6)-{β-D-galactopyranosyl (1→6)}n-β-D-galactopyranoside,
octadecyloxyphenyl β-D-galactopyranosyl (1→6)-{β-D-galactopyranosyl (1→6)}n-β-D-galactopyranoside,
In the above, n represents an integer from 1 to 18.
hexylphenyl β-D-glucopyranosyl (1→3)-β-D-glucopyranoside,
heptylphenyl β-D-glucopyranosyl (1→3)-β-D-glucopyranoside,
octylphenyl β-D-glucopyranosyl (1→3)-β-D-glucopyranoside,
nonylphenyl β-D-glucopyranosyl (1→3)-β-D-glucopyranoside,
decylphenyl β-D-glucopyranosyl (1→3)-β-D-glucopyranoside,
dodecylphenyl β-D-glucopyranosyl (1→3)-β-D-glucopyranoside,
hexadecylphenyl β-D-glucopyranosyl (1→3)-β-D-glucopyranoside,
octadecylphenyl β-D-glucopyranosyl (1→3)-β-D-glucopyranoside,
1,1,3,3-tetramethylbutylphenyl β-D-glucopyranosyl (1→3)-β-D-glucopyranoside,
hexylphenyl β-D-glucopyranosyl (1→3)-{β-D-glucopyranosyl (1→3)}n-β-D-glucopyranoside,
heptylphenyl β-D-glucopyranosyl (1→3)-{β-D-glucopyranosyl (1→3)}n-β-D-glucopyranoside,
octylphenyl β-D-glucopyranosyl (1→3)-{β-D-glucopyranosyl (1→3)}n-β-D-glucopyranoside,
nonylphenyl β-D-glucopyranosyl (1→3)-{β-D-glucopyranosyl (1→3)}n-β-D-glucopyranoside,
decylphenyl β-D-glucopyranosyl (1→3)-{β-D-glucopyranosyl (1→3)}n-β-D-glucopyranoside,
dodecylphenyl β-D-glucopyranosyl (1→3)-{β-D-glucopyranosyl (1→3)}n-β-D-glucopyranoside,
hexadecylphenyl β-D-glucopyranosyl (1→3)-{β-D-glucopyranosyl (1→3)}n-β-D-glucopyranoside,
octadecylphenyl β-D-glucopyranosyl (1→3)-{β-D-glucopyranosyl (1→3)}n-β-D-glucopyranoside,
1,1,3,3-tetramethylphenyl β-D-glucopyranosyl (1→3)-{β-D-glucopyranosyl (1→3)}n-β-D-glucopyranoside,
In the above, n represents an integer from 1 to 18.
hexyloxyphenyl β-D-glucopyranosyl (1→3)-β-D-glucopyranoside,
heptyloxyphenyl β-D-glucopyranosyl (1→3)-β-D-glucopyranoside,
octyloxyphenyl β-D-glucopyranosyl (1→3)-β-D-glucopyranoside,
nonyloxyphenyl β-D-glucopyranosyl (1→3)-β-D-glucopyranoside,
decyloxyphenyl β-D-glucopyranosyl (1→3)-β-D-glucopyranoside,
dodecyloxyphenyl β-D-glucopyranosyl (1→3)-β-D-glucopyranoside,
hexadecyloxyphenyl β-D-glucopyranosyl (1→3)-β-D-glucopyranoside,
octadecyloxyphenyl β-D-glucopyranosyl (1→3)-β-D-glucopyranoside,
hexyloxyphenyl β-D-glucopyranosyl (1→3)-{β-D-glucopyranosyl (1→3)}n-β-D-glucopyranoside,
heptyloxyphenyl β-D-glucopyranosyl (1→3)-{β-D-glucopyranosyl (1→3)}n-β-D-glucopyranoside,
octyloxyphenyl β-D-glucopyranosyl (1→3)-{β-D-glucopyranosyl (1→3)}n-β-D-glucopyranoside,
nonyloxyphenyl β-D-glucopyranosyl (1→3)-{β-D-glucopyranosyl (1→3)}n-β-D-glucopyranoside,
decyloxyphenyl β-D-glucopyranosyl (1→3)-{β-D-glucopyranosyl (1→3)}n-β-D-glucopyranoside,
dodecyloxyphenyl β-D-glucopyranosyl (1→3)-{β-D-glucopyranosyl (1→3)}n-β-D-glucopyranoside,
hexadecyloxyphenyl β-D-glucopyranosyl (1→3)-{β-D-glucopyranosyl (1→3)}n-β-D-glucopyranoside,
octadecyloxyphenyl β-D-glucopyranosyl (1→3)-{β-D-glucopyranosyl (1→3)}n-β-D-glucopyranoside,
In the above, n represents an integer from 1 to 18.
hexylphenyl β-D-glucopyranosyl (1→6)-β-D-glucopyranoside,
heptylphenyl β-D-glucopyranosyl (1→6)-β-D-glucopyranoside,
octylphenyl β-D-glucopyranosyl (1→6)-β-D-glucopyranoside,
nonylphenyl β-D-glucopyranosyl (1→6)-β-D-glucopyranoside,
decylphenyl β-D-glucopyranosyl (1→6)-β-D-glucopyranoside,
dodecylphenyl β-D-glucopyranosyl (1→6)-β-D-glucopyranoside,
hexadecylphenyl β-D-glucopyranosyl (1→6)-β-D-glucopyranoside,
octadecylphenyl β-D-glucopyranosyl (1→6)-β-D-glucopyranoside,
1,1,3,3-tetramethylbutylphenyl β-D-glucopyranosyl (1→6)-β-D-glucopyranoside,
hexylphenyl β-D-glucopyranosyl (1→6)-{β-D-glucopyranosyl (1→6)}n-β-D-glucopyranoside, heptylphenyl β-D-glucopyranosyl (1→6)-{β-D-glucopyranosyl (1→6)}n-β-D-glucopyranoside,
octylphenyl β-D-glucopyranosyl (1→6)-{β-D-glucopyranosyl (1→6)}n-β-D-glucopyranoside,
nonylphenyl β-D-glucopyranosyl (1→6)-{β-D-glucopyranosyl (1→6)}n-β-D-glucopyranoside,
decylphenyl β-D-glucopyranosyl (1→6)-{β-D-glucopyranosyl (1→6)}n-β-D-glucopyranoside,
dodecylphenyl β-D-glucopyranosyl (1→6)-{β-D-glucopyranosyl (1→6)}n-β-D-glucopyranoside,
hexadecylphenyl β-D-glucopyranosyl (1→6)-{β-D-glucopyranosyl (1→6)}n-β-D-glucopyranoside,
octadecylphenyl β-D-glucopyranosyl (1→6)-{β-D-glucopyranosyl (1→6)}n-β-D-glucopyranoside,
1,1,3,3-tetramethylphenyl β-D-glucopyranosyl (1→6)-{β-D-glucopyranosyl (1→6)}n-β-D-glucopyranoside,
In the above, n represents an integer from 1 to 18.
hexyloxyphenyl β-D-glucopyranosyl (1→6)-β-D-glucopyranoside,
heptyloxyphenyl β-D-glucopyranosyl (1→6)-β-D-glucopyranoside,
octyloxyphenyl β-D-glucopyranosyl (1→6)-β-D-glucopyranoside,
nonyloxyphenyl β-D-glucopyranosyl (1→6)-β-D-glucopyranoside,
decyloxyphenyl β-D-glucopyranosyl (1→6)-β-D-glucopyranoside,
dodecyloxyphenyl β-D-glucopyranosyl (1→6)-β-D-glucopyranoside,
hexadecyloxyphenyl β-D-glucopyranosyl (1→6)-β-D-glucopyranoside,
octadecyloxyphenyl β-D-glucopyranosyl (1→6)-β-D-glucopyranoside,
hexyloxyphenyl β-D-glucopyranosyl (1→6)-{β-D-glucopyranosyl (1→6)}n-β-D-glucopyranoside,
heptyloxyphenyl β-D-glucopyranosyl (1→6)-{β-D-glucopyranosyl (1→6)}n-β-D-glucopyranoside,
octyloxyphenyl β-D-glucopyranosyl (1→6)-{β-D-glucopyranosyl (1→6)}n-β-D-glucopyranoside,
nonyloxyphenyl β-D-glucopyranosyl (1→6)-{β-D-glucopyranosyl (1→6)}n-β-D-glucopyranoside,
decyloxyphenyl β-D-glucopyranosyl (1→6)-{β-D-glucopyranosyl (1→6)}n-β-D-glucopyranoside,
dodecyloxyphenyl β-D-glucopyranosyl (1→6)-{β-D-glucopyranosyl (1→6)}n-β-D-glucopyranoside,
hexadecyloxyphenyl β-D-glucopyranosyl (1→6)-{β-D-glucopyranosyl (1→6)}n-β-D-glucopyranoside,
octadecyloxyphenyl β-D-glucopyranosyl (1→6)-{β-D-glucopyranosyl (1→6)}n-β-D-glucopyranoside,
In the above, n represents an integer from 1 to 18.
hexylphenyl β-D-glucopyranosyl (1→2)-β-D-glucopyranoside,
heptylphenyl β-D-glucopyranosyl (1→2)-β-D-glucopyranoside,
octylphenyl β-D-glucopyranosyl (1→2)-β-D-glucopyranoside,
nonylphenyl β-D-glucopyranosyl (1→2)-β-D-glucopyranoside,
decylphenyl β-D-glucopyranosyl (1→2)-β-D-glucopyranoside,
dodecylphenyl β-D-glucopyranosyl (1→2)-β-D-glucopyranoside,
hexadecylphenyl β-D-glucopyranosyl (1→2)-β-D-glucopyranoside,
octadecylphenyl β-D-glucopyranosyl (1→2)-β-D-glucopyranoside,
1,1,3,3-tetramethylbutylphenyl β-D-glucopyranosyl (1→2)-β-D-glucopyranoside,
hexylphenyl β-D-glucopyranosyl (1→2)-{β-D-glucopyranosyl (1→2)}n-β-D-glucopyranoside,
heptylphenyl β-D-glucopyranosyl (1→2)-{β-D-glucopyranosyl (1→2)}n-β-D-glucopyranoside,
octylphenyl β-D-glucopyranosyl (1→2)-{β-D-glucopyranosyl (1→2)}n-β-D-glucopyranoside,
nonylphenyl β-D-glucopyranosyl (1→2)-{β-D-glucopyranosyl (1→2)}n-β-D-glucopyranoside,
decylphenyl β-D-glucopyranosyl (1→2)-{β-D-glucopyranosyl (1→2)}n-β-D-glucopyranoside,
dodecylphenyl β-D-glucopyranosyl (1→2)-{β-D-glucopyranosyl (1→2)}n-β-D-glucopyranoside,
hexadecylphenyl β-D-glucopyranosyl (1→2)-{β-D-glucopyranosyl (1→2)}n-β-D-glucopyranoside,
octadecylphenyl β-D-glucopyranosyl (1→2)-{β-D-glucopyranosyl (1→2)}n-β-D-glucopyranoside,
1,1,3,3-tetramethylphenyl β-D-glucopyranosyl (1→2)-{β-D-glucopyranosyl (1→2)}n-β-D-glucopyranoside,
In the above, n represents an integer from 1 to 18.
hexyloxyphenyl β-D-glucopyranosyl (1→2)-β-D-glucopyranoside,
heptyloxyphenyl β-D-glucopyranosyl (1→2)-β-D-glucopyranoside,
octyloxyphenyl β-D-glucopyranosyl (1→2)-β-D-glucopyranoside,
nonyloxyphenyl β-D-glucopyranosyl (1→2)-β-D-glucopyranoside,
decyloxyphenyl β-D-glucopyranosyl (1→2)-β-D-glucopyranoside,
dodecyloxyphenyl β-D-glucopyranosyl (1→2)-β-D-glucopyranoside,
hexadecyloxyphenyl β-D-glucopyranosyl (1→2)-β-D-glucopyranoside,
octadecyloxyphenyl β-D-glucopyranosyl (1→2)-β-D-glucopyranoside,
hexyloxyphenyl β-D-glucopyranosyl (1→2)-{β-D-glucopyranosyl (1→2)}n-β-D-glucopyranoside,
heptyloxyphenyl β-D-glucopyranosyl (1→2)-{β-D-glucopyranosyl (1→2)}n-β-D-glucopyranoside,
octyloxyphenyl β-D-glucopyranosyl (1→2)-{β-D-glucopyranosyl (1→2)}n-β-D-glucopyranoside,
nonyloxyphenyl β-D-glucopyranosyl (1→2)-{β-D-glucopyranosyl (1→2)}n-β-D-glucopyranoside,
decyloxyphenyl β-D-glucopyranosyl (1→2)-{β-D-glucopyranosyl (1→2)}n-β-D-glucopyranoside,
dodecyloxyphenyl β-D-glucopyranosyl (1→2)-{β-D-glucopyranosyl (1→2)}n-β-D-glucopyranoside,
hexadecyloxyphenyl β-D-glucopyranosyl (1→2)-{β-D-glucopyranosyl (1→2)}n-β-D-glucopyranoside,
octadecyloxyphenyl β-D-glucopyranosyl (1→2)-{β-D-glucopyranosyl (1→2)}n-β-D-glucopyranoside,
In the above, n represents an integer from 1 to 18.
hexylphenyl β-D-galactopyranosyl (1→4)-β-D-glucopyranoside,
heptylphenyl β-D-galactopyranosyl (1→4)-β-D-glucopyranoside,
octylphenyl β-D-galactopyranosyl (1→4)-β-D-glucopyranoside,
nonylphenyl β-D-galactopyranosyl (1→4)-β-D-glucopyranoside,
decylphenyl β-D-galactopyranosyl (1→4)-β-D-glucopyranoside,
dodecylphenyl β-D-galactopyranosyl (1→4)-β-D-glucopyranoside,
hexadecylphenyl β-D-galactopyranosyl (1→4)-β-D-glucopyranoside,
octadecylphenyl β-D-galactopyranosyl (1→4)-β-D-glucopyranoside, hexylphenyl β-D-galactopyranosyl (1→4)-{β-D-galactopyranosyl (1→4)}n-β-D-glucopyranoside,
heptylphenyl β-D-galactopyranosyl (1→4)-{β-D-galactopyranosyl (1→4)}n-β-D-glucopyranoside,
octylphenyl β-D-galactopyranosyl (1→4)-{β-D-galactopyranosyl (1→4)}n-β-D-glucopyranoside,
nonylphenyl β-D-galactopyranosyl (1→4)-{β-D-galactopyranosyl (1→4)}n-β-D-glucopyranoside,
decylphenyl β-D-galactopyranosyl (1→4)-{β-D-galactopyranosyl (1→4)}n-β-D-glucopyranoside,
dodecylphenyl β-D-galactopyranosyl (1→4)-{β-D-galactopyranosyl (1→4)}n- β-D-glucopyranoside,
hexadecylphenyl β-D-galactopyranosyl (1→4)-{β-D-galactopyranosyl (1→4)}n-β-D-glucopyranoside,
octadecylphenyl β-D-galactopyranosyl (1→4)-{β-D-galactopyranosyl (1→4)}n-β-D-glucopyranoside,
In the above, n represents an integer from 1 to 18.
hexyloxyphenyl β-D-galactopyranosyl (1→4)-β-D-glucopyranoside,
heptyloxyphenyl β-D-galactopyranosyl (1→4)-β-D-glucopyranoside,
octyloxyphenyl β-D-galactopyranosyl (1→4)-β-D-glucopyranoside,
nonyloxyphenyl β-D-galactopyranosyl (1→4)-β-D-glucopyranoside,
decyloxyphenyl β-D-galactopyranosyl (1→4)-β-D-glucopyranoside,
dodecyloxyphenyl β-D-galactopyranosyl (1→4)-β-D-glucopyranoside,
hexadecyloxyphenyl β-D-galactopyranosyl (1→4)-β-D-glucopyranoside,
octadecyloxyphenyl β-D-galactopyranosyl (1→4)-β-D-glucopyranoside,
hexyloxyphenyl β-D-galactopyranosyl (1→4)-{β-D-galactopyranosyl (1→4)}n-β-D-glucopyranoside,
heptyloxyphenyl β-D-galactopyranosyl (1→4)-{β-D-galactopyranosyl (1→4)}n-β-D-glucopyranoside,
octyloxyphenyl β-D-galactopyranosyl (1→4)-{β-D-galactopyranosyl (1→4) )n-β-D-glucopyranoside,
nonyloxyphenyl β-D-galactopyranosyl (1→4)-{β-D-galactopyranosyl (1→4)}n-β-D-glucopyranoside,
decyloxyphenyl β-D-galactopyranosyl (1→4)-{β-D-galactopyranosyl (1→4)}n-β-D-glucopyranoside,
dodecyloxyphenyl β-D-galactopyranosyl (1→4)-{β-D-galactopyranosyl (1→4)}n-β-D-glucopyranoside,
hexadecyloxyphenyl β-D-galactopyranosyl (1→4)-{β-D-galactopyranosyl (1→4)}n-β-D-glucopyranoside,
octadecyloxyphenyl β-D-galactopyranosyl (1→4)-{β-D-galactopyranosyl (1→4)}n-β-D-glucopyranoside,
In the above, n represents an integer from 1 to 18.
hexylphenyl β-D-galactopyranosyl-(1→4)-β-D-glucopyranoside,
heptylphenyl β-D-galactopyranosyl-(1→4)-β-D-glucopyranoside,
octylphenyl β-D-galactopyranosyl-(1→4)-β-D-glucopyranoside,
nonylphenyl β-D-galactopyranosyl-(1→4)-β-D-glucopyranoside,
decylphenyl β-D-galactopyranosyl-(1→4)-β-D-glucopyranoside,
dodecylphenyl β-D-galactopyranosyl-(1→4)-β-D-glucopyranoside,
hexadecylphenyl β-D-galactopyranosyl-(1→4)-β-D-glucopyranoside,
octadecylphenyl β-D-galactopyranosyl-(1→4)-β-D-glucopyranoside,
1,1,3,3-tetramethylphenyl β-D-galactopyranosyl-(1→4)-β-D-glucopyranoside,
hexylphenyl β-D-galactopyranosyl-(1→4)-{β-D-galactopyranosyl (1→4)}n-β-D-glucopyranoside,
heptylphenyl β-D-galactopyranosyl-(1→4)-{β-D-galactopyranosyl (1→4)}n-β-D-glucopyranoside,
octylphenyl β-D-galactopyranosyl-(1→4)-{β-D-galactopyranosyl (1→4)}n-β-D-glucopyranoside,
nonylphenyl β-D-galactopyranosyl-(1→4)-{β-D-galactopyranosyl (1→4)}n-β-D-glucopyranoside,
decylphenyl β-D-galactopyranosyl-(1→4)-{β-D-galactopyranosyl (1→4)}n-β-D-glucopyranoside,
dodecylphenyl β-D-galactopyranosyl-(1→4)-{β-D-galactopyranosyl (1→4)}n-β-D-glucopyranoside,
hexadecylphenyl β-D-galactopyranosyl-(1→4)-{β-D-galactopyranosyl (1→4)}n-β-D-glucopyranoside,
octadecylphenyl β-D-galactopyranosyl-(1→4)-{β-D-galactopyranosyl (1→4)}n-β-D-glucopyranoside,
1,1,3,3-tetramethylphenyl β-D-galactopyranosyl-(1→4)-{β-D-galactopyranosyl (1→4)}n-β-D-glucopyranoside,
In the above, n represents an integer from 1 to 18.
hexyloxyphenyl β-D-galactopyranosyl (1→4)-β-D-glucopyranoside,
heptyloxyphenyl β-D-galactopyranosyl (1→4)-β-D-glucopyranoside,
octyloxyphenyl β-D-galactopyranosyl (1→4)-β-D-glucopyranoside,
nonyloxyphenyl β-D-galactopyranosyl (1→4)-β-D-glucopyranoside,
decyloxyphenyl β-D-galactopyranosyl (1→4)-β-D-glucopyranoside,
dodecyloxyphenyl β-D-galactopyranosyl (1→4)-β-D-glucopyranoside,
hexadecyloxyphenyl β-D-galactopyranosyl (1→4)-β-D-glucopyranoside,
octadecyloxyphenyl β-D-galactopyranosyl (1→4)-β-D-glucopyranoside,
hexyloxyphenyl β-D-galactopyranosyl-(1→4)-{β-D-galactopyranosyl (1→4)}n-β-D-glucopyranoside,
heptyloxyphenyl β-D-galactopyranosyl-(1→4)-{β-D-galactopyranosyl (1→4)}n-β-D-glucopyranoside,
octyloxyphenyl β-D-galactopyranosyl-(1→4)-{β-D-galactopyranosyl (1→4)}n-β-D-glucopyranoside,
nonyloxyphenyl β-D-galactopyranosyl-(1→4)-{β-D-galactopyranosyl (1→4)}n-β-D-glucopyranoside,
decyloxyphenyl β-D-galactopyranosyl-(1→4)-{β-D-galactopyranosyl (1→4)}n-β-D-glucopyranoside,
dodecyloxyphenyl β-D-galactopyranosyl-(1→4)-{β-D-galactopyranosyl (1→4)}n-β-D-glucopyranoside,
hexadecyloxyphenyl β-D-galactopyranosyl-(1→4)-{β-D-galactopyranosyl (1→4)}n-β-D-glucopyranoside,
octadecyloxyphenyl β-D-galactopyranosyl-(1→4)-{β-D-galactopyranosyl (1→4)}n-β-D-glucopyranoside,
In the above, n represents an integer from 1 to 18.
hexylphenyl β-D-mannopyranosyl (1→2)-β-D-mannopyranoside,
heptylphenyl β-D-mannopyranosyl (1→2)-β-D-mannopyranoside,
octylphenyl β-D-mannopyranosyl (1→2)-β-D-mannopyranoside,
nonylphenyl β-D-mannopyranosyl (1→2)-β-D-mannopyranoside,
decylphenyl β-D-mannopyranosyl (1→2)-β-D-mannopyranoside,
dodecylphenyl β-D-mannopyranosyl (1→2)-β-D-mannopyranoside,
hexadecylphenyl β-D-mannopyranosyl (1→2)-β-D-mannopyranoside,
octadecylphenyl β-D-mannopyranosyl (1→2)-β-D-mannopyranoside, 1,1,3,3-tetramethylbutylphenyl β-D-mannopyranosyl (1→2)-β-D-mannopyranoside,
hexylphenyl β-D-mannopyranosyl (1→2)-{β-D-mannopyranosyl (1→2)}n-β-D-mannopyranoside,
heptylphenyl β-D-mannopyranosyl (1→2)-{β-D-mannopyranosyl (1→2)}n-β-D-mannopyranoside,
octylphenyl β-D-mannopyranosyl (1→2)-{β-D-mannopyranosyl (1→2)}n-β-D-mannopyranoside,
nonylphenyl β-D-mannopyranosyl (1→2)-{β-D-mannopyranosyl (1→2)}n-β-D-mannopyranoside,
decylphenyl β-D-mannopyranosyl (1→2)-{β-D-mannopyranosyl (1→2)}n-β-D-mannopyranoside,
dodecylphenyl β-D-mannopyranosyl (1→2)-{β-D-mannopyranosyl (1→2)}n-β-D-mannopyranoside,
hexadecylphenyl β-D-mannopyranosyl (1→2)-{β-D-mannopyranosyl (1→2)}n-β-D-mannopyranoside,
octadecylphenyl β-D-mannopyranosyl (1→2)-{β-D-mannopyranosyl (1→2)}n-β-D-mannopyranoside,
1,1,3,3-tetramethylphenyl β-D-mannopyranosyl (1→2)-{β-D-mannopyranosyl (1→2)}n-β-D-mannopyranoside, In the above, n represents an integer from 1 to 18.

hexyloxyphenyl β-D-mannopyranosyl (1→2)-β-D-mannopyranoside,
heptyloxyphenyl β-D-mannopyranosyl (1→2)-β-D-mannopyranoside,
octyloxyphenyl β-D-mannopyranosyl (1→2)-β-D-mannopyranoside,
nonyloxyphenyl β-D-mannopyranosyl (1→2)-β-D-mannopyranoside,
decyloxyphenyl β-D-mannopyranosyl (1→2)-β-D-mannopyranoside,
dodecyloxyphenyl β-D-mannopyranosyl (1→2)-β-D-mannopyranoside,
hexadecyloxyphenyl β-D-mannopyranosyl (1→2)-β-D-mannopyranoside,
octadecyloxyphenyl β-D-mannopyranosyl (1→2)-β-D-mannopyranoside,
hexyloxyphenyl β-D-mannopyranosyl (1→2)-{β-D-mannopyranosyl (1→2)}n-β-D-mannopyranoside,
heptyloxyphenyl β-D-mannopyranosyl (1→2)-{β-D-mannopyranosyl (1→2)}n-β-D-mannopyranoside,
octyloxyphenyl β-D-mannopyranosyl (1→2)-{β-D-mannopyranosyl (1→2)}n-β-D-mannopyranoside,
nonyloxyphenyl β-D-mannopyranosyl (1→2)-{β-D-mannopyranosyl (1→2)}n-β-D-mannopyranoside,
decyloxyphenyl β-D-mannopyranosyl (1→2)-{β-D-mannopyranosyl (1→2)}n-β-D-mannopyranoside,
dodecyloxyphenyl β-D-mannopyranosyl (1→2)-{β-D-mannopyranosyl (1→2)}n-β-D-mannopyranoside,
hexadecyloxyphenyl β-D-mannopyranosyl (1→2)-{β-D-mannopyranosyl (1→2)}n-β-D-mannopyranoside,
octadecyloxyphenyl β-D-mannopyranosyl (1→2)-{β-D-mannopyranosyl (1→2)}n-β-D-mannopyranoside, In the above, n represents an integer from 1 to 18.

hexylphenyl β-D-mannopyranosyl (1→3)-β-D-mannopyranoside,
heptylphenyl β-D-mannopyranosyl (1→3)-β-D-mannopyranoside,
octylphenyl β-D-mannopyranosyl (1→3)-β-D-mannopyranoside,
nonylphenyl β-D-mannopyranosyl (1→3)-β-D-mannopyranoside,
decylphenyl β-D-mannopyranosyl (1→3)-β-D-mannopyranoside,
dodecylphenyl β-D-mannopyranosyl (1→3)-β-D-mannopyranoside,
hexadecylphenyl β-D-mannopyranosyl (1→3)-β-D-mannopyranoside,
octadecylphenyl β-D-mannopyranosyl (1→3)-β-D-mannopyranoside,
1,1,3,3-tetramethylbutylphenyl β-D-mannopyranosyl (1→3)-β-D-mannopyranoside,
hexylphenyl β-D-mannopyranosyl (1→3)-{β-D-mannopyranosyl (1→3)}n-β-D-mannopyranoside,
heptylphenyl β-D-mannopyranosyl (1→3)-{β-D-mannopyranosyl (1→3)}n-β-D-mannopyranoside,
octylphenyl β-D-mannopyranosyl (1→3)-{β-D-mannopyranosyl (1→3)}n-β-D-mannopyranoside,
nonylphenyl β-D-mannopyranosyl (1→3)-{β-D-mannopyranosyl (1→3)}n-β-D-mannopyranoside,
decylphenyl β-D-mannopyranosyl (1→3)-{β-D-mannopyranosyl (1→3)}n-β-D-mannopyranoside,
dodecylphenyl β-D-mannopyranosyl (1→3)-{β-D-mannopyranosyl (1→3)}n-β-D-mannopyranoside,
hexadecylphenyl β-D-mannopyranosyl (1→3)-{β-D-mannopyranosyl (1→3)}n-β-D-mannopyranoside,
octadecylphenyl β-D-mannopyranosyl (1→3)-{β-D-mannopyranosyl (1→3)}n-β-D-mannopyranoside,
1,1,3,3-tetramethylphenyl β-D-mannopyranosyl (1→3)-{β-D-mannopyranosyl (1→3)}n-β-D-mannopyranoside, In the above, n represents an integer from 1 to 18.

hexyloxyphenyl β-D-mannopyranosyl (1→3)-β-D-mannopyranoside,
heptyloxyphenyl β-D-mannopyranosyl (1→3)-β-D-mannopyranoside,
octyloxyphenyl β-D-mannopyranosyl (1→3)-β-D-mannopyranoside,
nonyloxyphenyl β-D-mannopyranosyl (1→3)-β-D-mannopyranoside,
decyloxyphenyl β-D-mannopyranosyl (1→3)-β-D-mannopyranoside,
dodecyloxyphenyl β-D-mannopyranosyl (1→3)-β-D-mannopyranoside,
hexadecyloxyphenyl β-D-mannopyranosyl (1→3)-β-D-mannopyranoside,
octadecyloxyphenyl β-D-mannopyranosyl (1→3)-β-D-mannopyranoside,
hexyloxyphenyl β-D-mannopyranosyl (1→3)-{β-D-mannopyranosyl (1→3)}n-β-D-mannopyranoside,
heptyloxyphenyl β-D-mannopyranosyl (1→3)-{β-D-mannopyranosyl (1→3)}n-β-D-mannopyranoside,
octyloxyphenyl β-D-mannopyranosyl (1→3)-{β-D-mannopyranosyl (1→3)}n-β-D-mannopyranoside,
nonyloxyphenyl β-D-mannopyranosyl (1→3)-{β-D-mannopyranosyl (1→3)}n-β-D-mannopyranoside,
decyloxyphenyl β-D-mannopyranosyl (1→3)-{β-D-mannopyranosyl (1→3)}n-β-D-mannopyranoside,
dodecyloxyphenyl β-D-mannopyranosyl (1→3)-{β-D-mannopyranosyl (1→3)}n-β-D-mannopyranoside,
hexadecyloxyphenyl β-D-mannopyranosyl (1→3)-{β-D-mannopyranosyl (1→3)}n-β-D-mannopyranoside,
octadecyloxyphenyl β-D-mannopyranosyl (1→3)-{β-D-mannopyranosyl (1→3)}n-β-D-mannopyranoside, In the above, n represents an integer from 1 to 18.

hexylphenyl β-D-mannopyranosyl (1→4)-β-D-mannopyranoside,
heptylphenyl β-D-mannopyranosyl (1→4)-β-D-mannopyranoside,
octylphenyl β-D-mannopyranosyl (1→4)-β-D-mannopyranoside,
nonylphenyl β-D-mannopyranosyl (1→4)-β-D-mannopyranoside,
decylphenyl β-D-mannopyranosyl (1→4)-β-D-mannopyranoside,
dodecylphenyl β-D-mannopyranosyl (1→4)-β-D-mannopyranoside, hexadecylphenyl β-D-mannopyranosyl (1→4)-β-D-mannopyranoside,
octadecylphenyl β-D-mannopyranosyl (1→4)-β-D-mannopyranoside,
1,1,3,3-tetramethylbutylphenyl β-D-mannopyranosyl (1→4)-β-D-mannopyranoside,
hexylphenyl β-D-mannopyranosyl (1→4)-{β-D-mannopyranosyl (1→4)}n-β-D-mannopyranoside,
heptylphenyl β-D-mannopyranosyl (1→4)-{β-D-mannopyranosyl (1→4)}n-β-D-mannopyranoside,
octylphenyl β-D-mannopyranosyl (1→4)-{β-D-mannopyranosyl (1→4)}n-β-D-mannopyranoside,
nonylphenyl β-D-mannopyranosyl (1→4)-{β-D-mannopyranosyl (1→4)}n-β-D-mannopyranoside,
decylphenyl β-D-mannopyranosyl (1→4)-{β-D-mannopyranosyl (1→4)}n-β-D-mannopyranoside,
dodecylphenyl β-D-mannopyranosyl (1→4)-{β-D-mannopyranosyl (1→4)}n-β-D-mannopyranoside,
hexadecylphenyl β-D-mannopyranosyl (1→4)-{β-D-mannopyranosyl (1→4)}n-β-D-mannopyranoside,
octadecylphenyl β-D-mannopyranosyl (1→4)-{β-D-mannopyranosyl (1→4)}n-β-D-mannopyranoside,
1,1,3,3-tetramethylphenyl β-D-mannopyranosyl (1→4)-{β-D-mannopyranosyl (1→4)}n-β-D-mannopyranoside,
In the above, n represents an integer from 1 to 18.
hexyloxyphenyl β-D-mannopyranosyl (1→4)-β-D-mannopyranoside,
heptyloxyphenyl β-D-mannopyranosyl(1→4)-β-D-mannopyranoside,
octyloxyphenyl β-D-mannopyranosyl (1→4)-β-D-mannopyranoside,
nonyloxyphenyl β-D-mannopyranosyl (1→4)-β-D-mannopyranoside,
decyloxyphenyl β-D-mannopyranosyl (1→4)-β-D-mannopyranoside,
dodecyloxyphenyl β-D-mannopyranosyl (1→4)-β-D-mannopyranoside,
hexadecyloxyphenyl β-D-mannopyranosyl (1→4)-β-D-mannopyranoside,
octadecyloxyphenyl β-D-mannopyranosyl (1→4)-β-D-mannopyranoside,
hexyloxyphenyl β-D-mannopyranosyl (1→4)-{β-D-mannopyranosyl (1→4)}n-β-D-mannopyranoside,
heptyloxyphenyl β-D-mannopyranosyl (1→4)-{β-D-mannopyranosyl (1→4)}n-β-D-mannopyranoside,
octyloxyphenyl β-D-mannopyranosyl (1→4)-{β-D-mannopyranosyl (1→4)}n-β-D-mannopyranoside,
nonyloxyphenyl β-D-mannopyranosyl (1→4)-{β-D-mannopyranosyl (1→4)}n-β-D-mannopyranoside,
decyloxyphenyl β-D-mannopyranosyl (1→4)-{β-D-mannopyranosyl (1→4)}n-β-D-mannopyranoside,
dodecyloxyphenyl β-D-mannopyranosyl (1→4)-{β-D-mannopyranosyl (1→4)}n-β-D-mannopyranoside,
hexadecyloxyphenyl β-D-mannopyranosyl (1→4)-{β-D-mannopyranosyl (1→4)}n-β-D-mannopyranoside,
octadecyloxyphenyl β-D-mannopyranosyl (1→4)-{β-D-mannopyranosyl (1→4)}n-β-D-mannopyranoside,
In the above, n represents an integer from 1 to 18.
hexylphenyl β-D-mannopyranosyl (1→6)-β-D-mannopyranoside,
heptylphenyl β-D-mannopyranosyl (1→6)-β-D-mannopyranoside,
octylphenyl β-D-mannopyranosyl (1→6)-β-D-mannopyranoside,
nonylphenyl β-D-mannopyranosyl (1→6)-β-D-mannopyranoside,
decylphenyl β-D-mannopyranosyl (1→6)-β-D-mannopyranoside,
dodecylphenyl β-D-mannopyranosyl (1→6)-β-D-mannopyranoside,
hexadecylphenyl β-D-mannopyranosyl (1→6)-β-D-mannopyranoside,
octadecylphenyl β-D-mannopyranosyl (1→6)-β-D-mannopyranoside,
1,1,3,3-tetramethylbutylphenyl β-D-mannopyranosyl (1→6)-β-D-mannopyranoside,
hexylphenyl β-D-mannopyranosyl (1→6)-{β-D-mannopyranosyl (1→6)}n-β-D-mannopyranoside,
heptylphenyl β-D-mannopyranosyl (1→6)-{β-D-mannopyranosyl (1→6)}n-β-D-mannopyranoside,
octylphenyl β-D-mannopyranosyl (1→6)-{β-D-mannopyranosyl (1→6)}n-β-D-mannopyranoside,
nonylphenyl β-D-mannopyranosyl (1→6)-{β-D-mannopyranosyl (1→6)}n-β-D-mannopyranoside,
decylphenyl β-D-mannopyranosyl (1→6)-{β-D-mannopyranosyl (1→6)}n-β-D-mannopyranoside,
dodecylphenyl β-D-mannopyranosyl (1→6)-{β-D-mannopyranosyl (1→6)}n-β-D-mannopyranoside,
hexadecylphenyl β-D-mannopyranosyl (1→6)-{β-D-mannopyranosyl (1→6)}n-β-D-mannopyranoside,
octadecylphenyl β-D-mannopyranosyl (1→6)-{β-D-mannopyranosyl (1→6)}n-β-D-mannopyranoside,
1,1,3,3-tetramethylphenyl β-D-mannopyranosyl (1→6)-{β-D-mannopyranosyl (1→6)}n-β-D-mannopyranoside,
In the above, n represents an integer from 1 to 18.
hexyloxyphenyl β-D-mannopyranosyl (1→6)-β-D-mannopyranoside,
heptyloxyphenyl β-D-mannopyranosyl (1→6)-β-D-mannopyranoside,
octyloxyphenyl β-D-mannopyranosyl (1→6)-β-D-mannopyranoside,
nonyloxyphenyl.β-D-mannopyranosyl (1→6)-β-D-mannopyranoside,
decyloxyphenyl β-D-mannopyranosyl (1→6)-β-D-mannopyranoside,
dodecyloxyphenyl β-D-mannopyranosyl (1→6)-β-D-mannopyranoside,
hexadecyloxyphenyl β-D-mannopyranosyl (1→6)-β-D-mannopyranoside,
octadecyloxyphenyl β-D-mannopyranosyl (1→6)-β-D-mannopyranoside,
hexyloxyphenyl β-D-mannopyranosyl (1→6)-{β-D-mannopyranosyl (1→6)}n-β-D-mannopyranoside,
heptyloxyphenyl β-D-mannopyranosyl (1→6)-{β-D-mannopyranosyl (1→6)}n-β-D-mannopyranoside,
octyloxyphenyl β-D-mannopyranosyl (1→6)-{β-D-mannopyranosyl (1→6)}n-β-D-mannopyranoside,
nonyloxyphenyl β-D-mannopyranosyl (1→6)-{β-D-mannopyranosyl (1→6)}n-β-D-mannopyranoside,
decyloxyphenyl β-D-mannopyranosyl (1→6)-{β-D-mannopyranosyl (1→6)}n-β-D-mannopyranoside,
dodecyloxyphenyl β-D-mannopyranosyl (1→6)-{β-D-mannopyranosyl (1→6)}n-β-D-mannopyranoside,
hexadecyloxyphenyl β-D-mannopyranosyl (1→6)-{β-D-mannopyranosyl (1→6)}n-β-D-mannopyranoside,
octadecyloxyphenyl β-D-mannopyranosyl (1→6)-{β-D-mannopyranosyl (1→6)}n-β-D-mannopyranoside,
In the above, n represents an integer from 1 to 18.

In the above examples, the bonds of the sugar chains are shown as β-type bonds; however, there are of course also α-type bonds, and it would also be possible to show compounds in which the above β-type bonds have been replaced by α-type bonds. In the same way, there are also two types of bonding form of the glycosides, an α-type form and a β-type form. Furthermore, this is also possible in the case of D isomers and L isomers, so that each example compound shown here represents 8 different types of compounds.

Furthermore, these acyl derivatives are also included.

hexylphenyl β-D-glucopyranosyl-(1→4)-β-D-glucopyranoside,
heptylphenyl β-D-glucopyranosyl-(1→4)-β-D-glucopyranoside,
octylphenyl β-D-glucopyranosyl-(1→4)-β-D-glucopyranoside,
nonylphenyl β-D-glucopyranosyl-(1→4)-β-D-glucopyranoside,
decylphenyl β-D-glucopyranosyl-(1→4)-β-D-glucopyranoside,
dodecylphenyl β-D-glucopyranosyl-(1→4)-β-D-glucopyranoside,
hexadecylphenyl β-D-glucopyranosyl-(1→4)-β-D-glucopyranoside,
octadecylphenyl β-D-glucopyranosyl-(1→4)-β-D-glucopyranoside,
1,1,3,3-tetramethylbutylphenyl β-D-glucopyranosyl-(1→4)-β-D-glucopyranoside,
hexylphenyl β-D-glucopyranosyl-(1→4)-{β-D-glucopyranosyl (1→4)}n-β-D-glucopyranoside,
heptylphenyl β-D-glucopyranosyl-(1→4)-{β-D-glucopyranosyl (1→4)}n-β-D-glucopyranoside,
octylphenyl β-D-glucopyranosyl-(1→4)-{β-D-glucopyranosyl (1→4)}n-β-D-glucopyranoside,
nonylphenyl β-D-glucopyranosyl-(1→4)-{β-D-glucopyranosyl (1→4)}n-β-D-glucopyranoside,
decylphenyl β-D-glucopyranosyl-(1→4)-{β-D-glucopyranosyl (1→4)}n-β-D-glucopyranoside,
dodecylphenyl β-D-glucopyranosyl-(1→4)-{β-D-glucopyranosyl (1→4)}n-β-D-glucopyranoside,
hexadecylphenyl β-D-glucopyranosyl-(1→4)-{β-D-glucopyranosyl (1→4)}n-β-D-glucopyranoside,
octadecylphenyl β-D-glucopyranosyl-(1→4)-{β-D-glucopyranosyl (1→4)}n-β-D-glucopyranoside,
1,1,3,3-tetramethylbutylphenyl β-D-glucopyranosyl-(1→4)-{β-D-glucopyranosyl (1→4)}n-β-D-glucopyranoside, In the above, n represents an integer from 1 to 18.

hexyloxyphenyl β-D-glucopyranosyl-(1→4)-β-D-glucopyranoside,
heptyloxyphenyl β-D-glucopyranosyl-(1→4)-β-D-glucopyranoside,
octyloxyphenyl β-D-glucopyranosyl-(1→4)-β-D-glucopyranoside,
nonyloxyphenyl β-D-glucopyranosyl-(1→4)-β-D-glucopyranoside,
decyloxyphenyl β-D-glucopyranosyl-(1→4)-β-D-glucopyranoside,
dodecyloxyphenyl β-D-glucopyranosyl-(1→4)-β-D-glucopyranoside,
hexadecyloxyphenyl β-D-glucopyranosyl-(1→4)-β-D-glucopyranoside,
octadecyloxyphenyl β-D-glucopyranosyl-(1→4)-β-D-glucopyranoside,
hexyloxyphenyl β-D-glucopyranosyl-(1→4)-{β-D-glucopyranosyl (1→4)}n-βD-glucopyranoside,
heptyloxyphenyl β-D-glucopyranosyl-(1→4)-{β-D-glucopyranosyl (1→4)}n-β-D-glucopyranoside,
octyloxyphenyl β-D-glucopyranosyl-(1→4)-{β-D-glucopyranosyl (1→4)}n-β-D-glucopyranoside,
nonyloxyphenyl β-D-glucopyranosyl-(1→4)-{β-D-glucopyranosyl (1→4)}n-β-D-glucopyranoside,
decyloxyphenyl β-D-glucopyranosyl-(1→4)-{β-D-glucopyranosyl (1→4)}n-β-D-glucopyranoside,
dodecyloxyphenyl β-D-glucopyranosyl-(1→4)-{β-D-glucopyranosyl (1→4)}n-β-D-glucopyranoside,
hexadecyloxyphenyl β-D-glucopyranosyl-(1→4)-{β-D-glucopyranosyl (1→4)}n-β-D-glucopyranoside,
octadecyloxyphenyl β-D-glucopyranosyl-(1→4)-{β-D-glucopyranosyl (1→4)}n-β-D-glucopyranoside, In the above, n represents an integer from 1 to 18.

There are two types of glycoside bonding forms, an α-type type and a β-type, and since this is also possible in the case of a D isomer or an L isomer, each example compound above represents four different compounds. Furthermore, the acyl derivatives thereof are also included.

The sulfation ratio is used as an index expressing the degree of sulfation of the oligosaccharide aromatic glycoside sulfate. The sulfation ratio is obtained by dividing a number of sulfated hydroxyl groups by the total number of reactable hydroxyl groups, and thus expresses the degree of sulfation as a percentage. For example, in the case of an oligosaccharide aromatic glycoside comprising 5 hexose sugar units, if all hydroxyl groups which are able to be sulfated are sulfated, the sulfation ratio will be 100%, as shown in formula (1) below.

$$16/16 \times 100(\%) = 100\% \tag{1}$$

Furthermore, if it is assumed that only 2 hydroxyl groups have been sulfated, the sulfation ratio will be 12.5% as shown in formula (2) below.

$$2/16 \times 100(\%) = 12.5\% \tag{2}$$

The degree of sulfation of the sulfated oligosaccharide glycoside can be represented in this manner; however, in order to achieve a desired sulfation ratio, the relative amounts of the sulfation agent which is used must be determined in view of the relationship between a desired sulfation ratio and the number of groups of the sugars. In terms of the degree of sulfation, if the degree of sulfuric ester group substitution is low, toxicity becomes high, so that use as medication becomes difficult, and antiviral activity is reduced, so that the number of sulfuric ester groups which is introduced should preferably be more than 10% with respect to all hydroxyl groups of the oligosaccharide, and as high a sulfation ratio as possible is desirable.

The cations which form the counter ion to the sulfuric ester include sodium ions, potassium ions, magnesium ions, and the like; they are used as physiologically acceptable salts.

The antiviral agent of the present invention exhibits antiviral activity with respect to various types of viruses, and it is effective in the treatment of diseases caused by viral pathogens or in the treatment of infections associated with such diseases. More specifically, the antiviral agent of the present invention has superior antiviral activity with respect to the AIDS virus.

The details of the mechanism of action of the antiviral agent compound of the present invention have not yet been clarified; however, it can be inferred that this antiviral agent acts to prevent the adsorbtion to the target cell of the virus. The reason that the antiviral agent of the present invention possesses an antiviral action differing from conventional sulfated polysaccharides is that the molecule thereof is small when compared with those of the polysaccharides, so that the antiviral agent is easily able to approach closer to the active position, and by having hydrophilic groups such as sulfuric acid groups and hydroxyl groups of sugars and also an aromatic group as a lipophilic group, it can be inferred that the compatibility with the surface of the organism will be increased.

Among the compounds of the present invention, oligosaccharide aromatic glycoside sulfates consisting of 5 to 11 sugar units bonded in a β (1→3) structure, and oligosaccharide aromatic glycoside sulfates having 4 sugar units with a lactose structure, exhibit extremely high activity with respect to the AIDS virus, the $EC_{50}$ value (50% effective concentration) being less than approximately 1 μg per milliliter, as shown in Tables 1 and 2, so that the effectiveness of the present group of compounds has become clear.

In a single oral administration toxicity test in mice in which all the compounds of examples 30 to 43 were tested at an administered amount of 500 mg per kilogram, mortality was not observed, thus it was clear that the toxicity of the present group of compounds was extremely low.

In antiviral agents having as active components thereof the oligosaccharide aromatic glycoside sulfate of the present invention, the percentage of active component contained varies depending on the type of formulation; however, in general, the percentage of active component contained should preferably be in a range of from 0.1 to 100%. Antiviral agents using this active component may be formulated in the normal manner, for example, as tablets, capsules, powders, pills, liquids, injections, syrups, suppositories, or the like, and many be administered either orally or non-orally.

It is possible, in the formulation process, to add vehicles or additives which are commonly used in the production of pharmaceuticals. Those commonly used vehicles include, for example, water, physiological saline solution, alcohol, polyethylene glycol, glycerol ester, gelatin, carbohydrate magnesium stearate, talc, and the like. Furthermore, examples of additives include antiseptics, sterilizers, lubricants, coating agents, penetrants, emulsifiers, coloring agents, masking flavors, and aromatic agents.

The dosage of the antiviral agent of the present invention varies depended on the administered form of the drug, the number of administrations, the condition of the patient, the weight of the patient, and the gravity of the illness; however, from 0.1 mg to 150 mg, and preferably from 0.5 mg to 100 mg per 1 kilogram of body weight should be administered within a 24 hour period divided into several administrations. The number of administrations, as well, is determined by the form of the drug, the condition of the patient, body weight, and the gravity of the illness; however, 1 to 3 administrations in a 24 hour period are preferable. Depending on the case, continuous intravenous administration is also possible.

PREFERRED EXAMPLES

Hereinbelow, the present invention will be explained in greater detail by means of preferred examples; however, the present invention is not limited to these preferred examples.

EXAMPLE 1

Synthesis of p-octylphenyl laminaripentaoside peracetate [p-octylphenyl β-D-glucopyranosyl-(1→3)-β-D-glucopyranosyl-(1→3)]₃-β-D-glycopyranoside peracetate]

600 mg (0.39 mmol) of laminaripentaose peracetate was dissolved in 20 ml of methylene chloride, 162 mg of p-octylphenol was added to this and dissolved, then 0.075 ml of TMS triflate was added at a temperature in the range of from −8° to −5° C., and this was agitated for 5 hours. 0.5 ml of triethylamine was added to this, this was agitated for 30 minutes at −8° C. This was then poured into an aqueous solution of sodium bicarbonate, this was extracted with ethyl acetate, the solvent was removed, and 714 mg of reaction mixture was obtained. 198 mg of β-anomer and 63 mg of α-β-anomer mixture were obtained after purification by means of silica gel column chromatography.

MATERIAL VALUES OF THE β ANOMER

Specific Rotation $[\alpha]_D = -39.0°$ (c=0.78, chloroform; 26° C.)

¹H-NMR (CDCl₃) 0.88 ppm CH₃, 3H, t, J=7.2 Hz 1.24–1.28 (CH₂)₅, 10H, m 1.56 CH₂, 2H, bm 1.97–2.18 (Ac)×16, 48H 2.55 CH₂, 2H, t, J=7.6 Hz 3.68–5.14 Sugar skeleton, 34H 5.23 Reducing terminal sugar position-2, d×d, J=7.6, 9.6 Hz 6.87 Aromatic group, 2H, d, J=8.4 Hz 7.08 Aromatic group, 2H, d, J=8.4 Hz

EXAMPLE 2

Synthesis of p-pentylphenyl laminaripentaoside peracetate [p-pentylphenyl β-D-glucopyranosyl-(1→3)-β-D-glucopyranosyl-(1→3)]₃-β-D-glucopyranoside peracetate]

600 mg (0.39 mmol) of laminaripentaose peracetate was dissolved in 20 ml of methylene chloride, 96 mg of p-pentylphenol was added to this and dissolved, 0.076 ml of TMS triflate was added to this at a temperature in a range of between −10° and −7° C., and this was agitated for 5 hours. 0.5 ml of triethylamine was added to this and this was agitated for 3 minutes at a temperature of −8° C., this was then poured into an aqueous solution of sodium bicarbonate; this was extracted with ethyl acetate and the solvent removed, and 680 mg of a reaction mixture was thus obtained. From this 190 mg of β-anomer and 74 mg of α-β-anomer mixture were obtained after purification by means of silica gel column chromatography.

PHYSICAL VALUES OF THE β ANOMER

Specific Rotation $[\alpha]_D = -40.2°$ (c=0.56, chloroform; 26° C.)

¹H-NMR (CDCl₃) 0.88 ppm CH₃, 3H, t, J=7.2 Hz 1.24–1.28 (CH₂)₂, 4H, m 1.56 CH₂, 2H, bm 1.97–2.18 (Ac)×16, 48H 2.55 CH₂, 2H, t, J=7.6 Hz 3.68–5.14 Sugar skeleton, 34H 5.23 Reducing terminal sugar position-2, d×d, J=7.6, 9.6 Hz 6.87 Aromatic group, 2H, d, J=8.4 Hz 7.08 Aromatic group, 2H, d, J=8.4 Hz

EXAMPLE 3

Synthesis of p-heptyloxyphenyl laminaripentaoside peracetate [p-heptyloxyphenyl β-D-glucopyranosyl-(1→3)-[β-D-glucopyranosyl-( 1→3)]₃-β-D-glucopyranoside peracetate]

600 mg (0.39 mmol) of laminaripentaose peracetate was dissolved in 20 ml of methylene chloride, 122 mg of p-heptyloxyphenol was added to this and dissolved, 0.076 ml of TMS triflate were added to this at a temperature in a range of −10° to −7° C., and this was agitated for 5 hours. 0.5 ml of triethylamine were added to this, and this was agitated for 3 minutes at a temperature of −8° C., this was poured into an aqueous solution of sodium bicarbonate, this was extracted with ethyl acetate, the solvent was removed, and 680 mg of the reaction mixture were obtained. From this, 192 mg of β-anomer and 79 mg of α-β-anomer mixture were obtained after refinement by means of silica gel column chromatography.

PHYSICAL VALUES OF THE β ANOMER

Specific Rotation $[\alpha]_D=-37.5°$ (C=0.66, chloroform; 26° C.)

$^1$H-NMR (CDCl$_3$) 0.89 ppm CH$_3$, 3H, t, J=6.8 Hz 1.30–1.40 (CH$_2$)$_4$, 8H, m 1.75 CH$_2$, 2H, bm 2.00–2.20 (Ac)×16, 48H 3.90 CH$_2$, 2H, t, J=6.8 Hz 3.68–5.14 Sugar skeleton, 34H 5.21 Reducing terminal sugar position-2, d×d, J=8.0, 9.2 Hz 6.80 Aromatic group, 2H, d, J=9.2 Hz 6.90 Aromatic group, 2H, d, J=9.2 Hz

EXAMPLE 4

Synthesis of p-octylphenyl laminaripentaoside peracetate [p-octylphenyl β-D-glucopyranosyl-(1→3)-{β-D-glucopyranosyl-(1→3)}$_3$-β-D-glucopyranoside peracetate] (Alternative method of Example 1)

(1) Synthesis of 1-OH laminaripentaose 2.656 g (1.72 mmol) of acetylated α-laminaripentaose was placed in a 200 ml flask and dissolved in 30 ml of DMF. To this was added 0.222 g (1.4 eq.) of hydrazinium acetate, and this was then agitated at 50° C. for one hour. This mixture was extracted with ethyl acetate, the solvent was removed, and 2.53 g of the reaction mixture was obtained. This was separated in a silica gel column (eluent, ethyl acetate/hexane=70/30), and 1.753 g of the desired compound was obtained. Furthermore, 1.71 g of the desired compound was gained by means of chloroform/hexane reprecipitation.

Specific Rotation $[\alpha]_D=-39.0°$ (c=0.78, CHCl$_3$; 26° C.)

$^1$H-NMR (CDCl$_3$) Disappearance of anomer-position proton $^{13}$C-NMR Reducing terminal sugar skeleton position-1 carbon 90.13 ppm Other sugar skeleton position-1 carbon 100.52, 100.61 100.79, 101.05

(2) Synthesis of laminaripentaose trichloroacetoimidate 1.500 g (1.0 mmol) of the above 1-OH laminaripentaose and 432 mg (3.0 eq.) of trichloroacetonitrile were placed in a 25 ml 3-necked reaction vessel and dissolved in 10 ml of CH$_2$Cl$_2$. This was cooled to a temperature of 0° C. in an atmosphere of argon gas, 228 mg (1.5 eq.) of DBU was added, and this was reacted for 7 hours. After the termination of the reaction, 1.146 g of the desired substance were obtained by directly passing the reaction mixture through a silica gel flash column (ethyl acetate/hexane=85/15).

$^1$H-NMR (CDCl$_3$) 6.43 ppm Reducing terminal α isomer position-1 (d, J=4.0 Hz) 8.74 ppm NH (broad d) IR (NaCl plate) 3350 cm$^{-1}$ N–H 1680 cm$^{-1}$ C=N Specific Rotation $[\alpha]_D=-24.5°$ (C=0.59, CHCl$_3$, 30° C.)

(3) Synthesis of p-octylphenyl laminaripentaoside

| laminaripentaose trichloroacetoimidate | 240 mg |
| p-octylphenol | 60 mg |
| TfOH | 22 mg |
| CH$_2$Cl$_2$ | 5 ml |

The above were placed in a reaction vessel under the stream of an atmosphere of argon gas and were reacted for 2.5 hours at a temperature of 0° C. The reaction mixture was supplied to a silica gel column, and 191 mg of a β-isomer product and 25 mg of an α-β-mixture product were obtained.

Specific Rotation $[\alpha]_D=-39.2°$ (c=1.15, CHCl$_3$, 28° C.)

$^1$H-NMR (CDCl$_3$) 0.88 ppm CH$_3$, 3H, t, J=7.2 Hz 1.24–1.28 (CH$_2$)$_5$, 10H, m 1.56 CH$_2$, 2H, bm 1.97–2.18 (Ac)×16, 48H 2.55 CH$_2$, 2H, t, J=7.6 Hz 3.68–5.14 Sugar skeleton, 34H 5.23 Reducing terminal sugar position-2, d×d, J=7.6, 9.6 Hz 6.87 Aromatic group, 2H, d, J=8.4 Hz 7.08 Aromatic group, 2H, d, J=8.4 Hz

EXAMPLE 5

Synthesis of p-octylphenyl laminariheptaoside peracetate [p-octylphenyl β-D-glucopyranosyl-(1→3)-{β-D-glucopyranosyl-(1→3)}$_5$-β-D-glucopyranoside peracetate]

400 mg (0.235 mmol) of laminariheptaose peracetate was dissolved in 20 ml of methylene chloride, 77 mg of p-octylphenol was added and dissolved, 0.08 ml of TMS triflate was added at a temperature between –8° and –5° C., and this was reacted for 5 hours. To this was added 0.7 ml of triethyl amine, this was agitated for 30 minutes at a temperature of –8° C., this was poured into an aqueous solution of sodium bicarbonate, extracted with ethyl acetate, the solvent was removed, and 490 mg of reaction mixture was obtained. From this, 156 mg of β-anomer and 77 mg of (α-β-anomer mixture were obtained after purification by silica gel column chromatography.

PHYSICAL VALUES OF THE β ANOMER

Specific Rotation $[\alpha]_D=-43.1°$ (c=0.75, chloroform; 26° C.)

$^1$H-NMR (CDCl$_3$) 0.88 ppm CH$_3$, 3H, t, J=7.2 Hz 1.24–1.28 (CH$_2$)$_5$, 10H, m 1.56 CH$_2$, 2H, bm 1.97–2.18 (Ac)×23, 69H 2.56 CH$_2$, 2H, t, J=7.6 Hz 3.68–5.3 Sugar skeleton, 49H 6.87 Aromatic group, 2H, d, J=8.4 Hz 7.08 Aromatic group, 2H, d, J=8.4 Hz

EXAMPLE 6

Synthesis of p-(1,1,3,3-tetramethylbutyl)phenyl laminaripentoside peracetate [p-(1,1,3,3-tetramethylbutyl)phenyl β-D-glucopyranosyl-(1→3)-{β-D-glucopyranosyl-(1→3)}$_3$-β-D-glucopyranoside peracetate]

1.500 g (0.911 mmol) of the laminaripentaose trichloroacetoimidate which was synthesized in Example 4-(2) and 376 mg of p-(1,1,3,3-tetramethylbutyl)phenol were placed in a 25 ml 3-necked reaction vessel and dissolved in 20 ml of methylene chloride. This was cooled to a temperature of 0° C. in an argon gas atmosphere, 137 mg (1.0 eq.) of triflate was added and this was agitated for 4 hours. After the termination of the reaction, the reaction mixture was poured into an aqueous solution of sodium bicarbonate, this was extracted with methylene chloride, the solvent was removed, and 1.737 g of the reaction mixture was obtained. From this, 549 mg of β-anomer and 152 mg of α-β-anomer mixture were obtained after purification by means of silica gel column chromatography.

PHYSICAL VALUES OF THE β ANOMER

Specific Rotation $[\alpha]_D=-40.1°$ (c=1.10, CHCl$_3$; 29° C.)

$^1$H-NMR (CDCl$_3$) 0.71 ppm CH$_3$×3, 9H, s 1.34 CH$_3$×2, 6H, s 1.74 CH$_2$, 2H, s 1.97–2.19 (Ac)×16, 48H 3.67–5.25 Sugar skeleton, 34H 5.23 Reducing terminal sugar position-2, d×d, J=8.0, 9.6 Hz 6.86 Aromatic group, 2H, d, J=8.8 Hz 7.27 Aromatic group, 2H, d, J=8.8 Hz

EXAMPLE 7

Synthesis of p-(1,1,3,3-tetramethylbutyl)phenyl laminarioligosaccharide peracetate [p-(1,1,3,3-tetramethylbutyl)phenyl β-D-glucopyranosyl-(1→3)-{β-D-glucopyranosyl-(1→3)}$_m$-β-D-glucopyranoside peracetate] (where m=7~9)

397 mg of laminarioligosaccharide peracetate (comprising 9-sugar 18.1%, 10-sugar 44.9%, 11-sugar 37.0%) was dissolved in 6 ml of methylene chloride, 107 mg of 1,1,3,3

-tetramethylbutylphenol was added to this and dissolved, 0.050 ml (0.26 mmol) of TMS triflate was added at a temperature of −10° C., this was argon exchanged, and agitated for 24.5 hours. 0.03 ml (0.22 mmol) of triethylamine was added and this was agitated for 30 minutes at a temperature of 0° C., this was diluted with ethyl acetate, this was washed with an aqueous solution of sodium bicarbonate and a saturated aqueous saline solution. The solvent was removed, and 478 mg of a mixture was obtained. 79.4 mg of the desired β-anomer was obtained after purification by means of silica gel column chromatography.

PHYSICAL VALUES OF THE β ANOMER

Specific Rotation $[\alpha]_D = -49.09°$ (c=0.51, chloroform; 31.6° C.)

$^1$H-NMR 0.71 ppm $(CH_3) \times 3$, 9H 1.33 $(CH_3) \times 2$, 6H 1.70 $CH_2$, 2H 1.91–2.21 (Ac) approximately 95H 3.65–5.23 Sugar skeleton, approximately 71H 6.87 Aromatic group, 2H, J=8.0 Hz 7.25 Aromatic group, 2H, J=8.0 Hz

EXAMPLE 8

Synthesis of p-n-octylphenyl β-D-galactopyranosyl-(1→4)-β-D-galactopyranosyl-(1→4)-β-D-glucopyranoside peracetate 3.21 g (3.32 mmol) of β-D-galactopyranosyl-(1→4)-β-D-galactopyranosyl-(1→4)-β-D-glucopyranose peracetate and 1.06 g (5.17 mmol) of p-n-octylphenol were dissolved in 13 ml of dehydrated methylene chloride, and this was agitated in an atmosphere of nitrogen gas at a temperature of −11° C. 0.8 ml of TMS triflate was added to this, and agitation was continued for 21 hours at a constant temperature. 0.5 ml of triethyl amine was added to this, this was agitated for 10 minutes, the reaction temperature was returned to room temperature, and the mixture was then diluted by adding ethyl acetate. This solution was twice washed with an aqueous solution of sodium bicarbonate; washing was then conducted once with distilled water; washing was conducted with saturated aqueous saline solution; and an organic layer was dehydrated by means of sodium sulfate. After dehydration, 4.3 g of a crude product was obtained by condensation under reduced pressure.

2.52 g (2.26 mmol) of the desired compound in powdered form was obtained after purification by means of silica gel column chromatography (hexane/ethyl acetate=1/1, volume ratio).

Specific Rotation $[\alpha]_D = -0.39°$ (c=1.1, chloroform; 31° C.)

Nuclear Magnetic Resonance spectrum (TMS standard: CDCl$_3$) (Assignment: ppm: proton number: form: coupling constant)

| aglycon portion | | | |
|---|---|---|---|
| alkylmethyl | 0.88 | 3 H | t |
| methylene | 1.28 | 10 H | m |
| methylene | 1.56 | 2 H | m |
| acetyl methyl | 1.99–2.18 | 30 H | |
| benzyl-position methylene | 2.54 | 2 H | d |
| aromatic ring oxygen side | 6.88 | 2 H | d |
| aromatic ring alkyl side | 7.07 | 2 H | d |

| Sugar-chain portions (from the portion closest to aglycon) | | | |
|---|---|---|---|
| Glucose ring | | | |
| position 1 | 5.00 | 1 H d | J1,2=7.6 Hz |
| position 2 | 5.17 | 1 H dd | J2,3=9.2 Hz |
| position 3 | 5.26 | 1 H t | J3,4=9.3 Hz |
| position 4 | 3.87 | 1 H t | J4,5=9.6 Hz |
| position 5 | 3.76 | 1 H m | |
| position 6 | 4.05–4.5 | 2 H | |
| Galactose ring | | | |
| position 1 | 4.44 | 1 H d | J1,2=7.6 Hz |
| position 2 | 4.99 | 1 H dd | J2,3=10.4 Hz |
| position 3 | 4.87 | 1 H dd | J3,4=3.2 Hz |
| position 4 | 4.12 | 1 H bd | |
| position 5 | 3.70 | 1 H bt | |
| position 6 | 4.05–4.48 | 2 H | |
| Galactose ring | | | |
| position 1 | 4.51 | 1 H d | J1,2=7.6 Hz |
| position 2 | 5.18 | 1 H dd | J2,3=10.6 Hz |
| position 3 | 5.00 | 1 H dd | J3,4=3.2 Hz |
| position 4 | 5.37 | 1 H dd | J4,5≅0.8 Hz |
| position 5 | 3.83 | 1 H bt | |
| position 6 | 4.05–4.16 | 2 H | |

Infrared Absorption Spectrum (cm$^{-1}$): Principal Absorption Value 2950, 1760, 1520, 1380, 1230, 1050

EXAMPLE 9

Synthesis of p-n-heptylphenyl β-D-galactopyranosyl-(1→4)-β-D-galactopyranosyl-(1→4)-β-D-glucopyranoside peracetate The desired compound was obtained in powdered form in the same manner as in Example 8 from p-n-heptylphenol and β-D-galactopyranosyl-(1→4)-β-D-galactopyranosyl-(1→4)-β-D-glucopyranose peracetate.

Specific Rotation $[\alpha]_D = -1.92°$ (c=0.78, chloroform; 30° C.)

Nuclear Magnetic Resonance spectrum (TMS standard: CDCl$_3$) (Assignment: ppm: proton number: form: coupling constant)

| aglycon portion | | | |
|---|---|---|---|
| alkylmethyl | 0.89 | 3 H | t |
| methylene | 1.28 | 8 H | m |
| methylene | 1.56 | 2 H | m |
| acetyl methyl | 1.99–2.18 | 30 H | |
| benzyl-position methylene | 2.54 | 2 H | t |
| aromatic ring oxygen side | 6.88 | 2 H | d |
| aromatic ring alkyl side | 7.07 | 2 H | d |

| Sugar-chain portions (from the portion closest to aglycon) | | | |
|---|---|---|---|
| Glucose ring | | | |
| position 1 | 5.00 | 1 H d | J1,2=7.6 Hz |
| position 2 | 5.17 | 1 H dd | J2,3=9.2 Hz |
| position 3 | 5.26 | 1 H t | J3,4=9.3 Hz |
| position 4 | 3.87 | 1 H t | J4,5=9.6 Hz |
| position 5 | 3.76 | 1 H m | |
| position 6 | 4.05–4.5 | 2 H | |
| Galactose ring | | | |
| position 1 | 4.44 | 1 H d | J1,2=7.6 Hz |
| position 2 | 4.99 | 1 H dd | J2,3=10.4 Hz |
| position 3 | 4.87 | 1 H dd | J3,4=3.2 Hz |
| position 4 | 4.12 | 1 H bd | |
| position 5 | 3.70 | 1 H bt | |
| position 6 | 4.05–4.48 | 2 H | |

| Galactose ring | | | |
|---|---|---|---|
| position 1 | 4.51 | 1 H d | J1,2=7.6 Hz |
| position 2 | 5.18 | 1 H dd | J2,3=10.6 Hz |
| position 3 | 5.00 | 1 H dd | J3,4=3.2 Hz |
| position 4 | 5.37 | 1 H bd | J4,5≅0.8 Hz |
| position 5 | 3.83 | 1 H bt | |
| position 6 | 4.05–4.16 | 2 H | |

Infrared Absorption Spectrum ($cm^{-1}$): Principal Absorption Value 2950, 1755, 1520, 1375, 1230, 1050

EXAMPLE 10

Synthesis of p-n-heptyloxyphenyl β-D-galactopyranosyl-(1→4)-β-D-galactopyranosyl-(1→4)-β-D-glucopyranoside peracetate 2.96 g (2.66 mmol) of the desired compound in powdered form was obtained from the reaction of 2.26 g (10.9 mmol) of p-n-heptyloxyphenol and 4.51 g (4.67 mmol) of β-D-galactopyranosyl-(1→4)-β-D-galactopyranosyl-(1→4)-β-D-glucopyranose peracetate. The post-reaction processing and refinement were identical to that of Example 8.

Specific Rotation $[\alpha]_D$=−2.97° (c=0.61, chloroform; 29° C.)

Nuclear Magnetic Resonance spectrum (TMS standard: $CDCl_3$)

(Assignment: ppm: proton number: form: coupling constant)

| aglycon portion | | | |
|---|---|---|---|
| alkylmethyl | 0.89 | 3 H | t |
| methylene | 1.30 | 6 H | m |
| phenoxy γ-position methylene | 1.44 | 2 H | m |
| phenoxy β-position methylene | 1.75 | 2 H | m |
| acetyl methyl | 1.99–2.18 | 30 H | |
| phenoxy α-position methylene | 3.89 | 2 H | t |
| aromatic ring sugar side | 6.79 | 2 H | d |
| aromatic ring alkyl side | 6.91 | 2 H | d |

Sugar-chain portions (from the portion closest to aglycon)

| Glucose ring | | | |
|---|---|---|---|
| position 1 | 4.91 | 1 H d | J1,2=8.0 Hz |
| position 2 | 5.15 | 1 H dd | J2,3=9.2 Hz |
| position 3 | 5.25 | 1 H t | J3,4=9.2 Hz |
| position 4 | 3.87 | 1 H t | J4,5=9.2 Hz |
| position 5 | 3.72 | 1 H m | |
| position 6 | 4.07–4.5 | 2 H | |
| Galactose ring | | | |
| position 1 | 4.44 | 1 H d | J1,2=8.4 Hz |
| position 2 | 4.99 | 1 H dd | J2,3=10.8 Hz |
| position 3 | 4.87 | 1 H dd | J3,4=2.8 Hz |
| position 4 | 4.12 | 1 H bd | |
| position 5 | 3.70 | 1 H bt | |
| position 6 | 4.10–4.48 | 2 H | |
| Galactose ring | | | |
| position 1 | 4.51 | 1 H d | J1,2=7.6 Hz |
| position 2 | 5.17 | 1 H dd | J2,3=10.8 Hz |
| position 3 | 5.00 | 1 H dd | J3,4=3.4 Hz |
| position 4 | 5.37 | 1 H dd | J4,5≅0.8 Hz |
| position 5 | 3.83 | 1 H bt | |
| position 6 | 4.05–4.16 | 2 H | |

Infrared Absorption Spectrum ($cm^{-1}$): Principal Absorption Value 2950, 1755, 1515, 1375, 1230, 1050

EXAMPLE 11

Synthesis of p-1,1,3,3-tetramethylbutylphenyl β-D-galactopyranosyl-(1→4)-β-D-galactopyranosyl-(1→4)-β-D-glucoside peracetate The desired compound was obtained in powdered form from p-1,1,3,3-tetramethylbutylphenol and β-D-galactopyranosyl-(1→4)-β-D-galactopyranosyl-(1→4)-β-D-glucose peracetate in the same manner as in Example 8.

Specific Rotation $[\alpha]_D$=−2.25° (c=0.76, chloroform; 30° C.)

Nuclear Magnetic Resonance spectrum (TMS standard: $CDCl_3$) (Assignment: ppm: proton number: form: coupling constant)

| aglycon portion | | | |
|---|---|---|---|
| alkylmethyl | 0.72 | 9 H | |
| alkylmethyl | 1.33 | 6 H | |
| methylene | 1.70 | 2 H | |
| acetyl methyl | 1.97–2.18 | 30 H | |
| aromatic ring sugar side | 6.88 | 2 H | d |
| aromatic ring alkyl side | 7.26 | 2 H | d |

Sugar-chain portions (from the portion closest to aglycon)

| Glucose ring | | | |
|---|---|---|---|
| position 1 | 5.02 | 1 H d | J1,2=8.0 Hz |
| position 2 | 5.17 | 1 H dd | J2,3=9.2 Hz |
| position 3 | 5.26 | 1 H t | J3,4=9.2 Hz |
| position 4 | 3.88 | 1 H t | J4,5=9.2 Hz |
| position 5 | 3.77 | 1 H m | |
| position 6 | 4.05–4.49 | 2 H | |
| Galactose ring | | | |
| position 1 | 4.44 | 1 H d | J1,2=8.0 Hz |
| position 2 | 4.99 | 1 H dd | J2,3=10.0 Hz |
| position 3 | 4.87 | 1 H dd | J3,4=3.0 Hz |
| position 4 | 4.12 | 1 H bd | |
| position 5 | 3.70 | 1 H bt | |
| position 6 | 4.15–4.37 | 2 H | |
| Galactose ring | | | |
| position 1 | 4.51 | 1 H d | J1,2=8.0 Hz |
| position 2 | 5.18 | 1 H dd | J2,3=10.0 Hz |
| position 3 | 5.00 | 1 H dd | J3,4=3.6 Hz |
| position 4 | 5.37 | 1 H dd | J4,5≅0.8 Hz |
| position 5 | 3.83 | 1 H bt | |
| position 6 | 4.05–4.16 | 2 H | |

Infrared Absorption Spectrum ($cm^{-1}$): Principal Absorption Value 2980, 1750, 1520, 1370, 1230, 1050

EXAMPLE 12

Synthesis of p-n-octylphenyl β-D-galactopyranosyl-(1→4)-{β-D-galactopyranosyl-(1→4)}$_2$-β-D-glucopyranoside peracetate 1.82 g (1.3 mmol) of the desired compound was obtained in powdered form from 1.03 g (5.0 mmol) of p-n-octylphenol and 4.55 g (3.63 mmol) of β-D-galactopyranosyl-(1→4)-{β-D-galactopyranosyl-(1→4)}$_2$-β-D-glucopyranose peracetate by means of reaction, post reaction processing, and purification identical to that of Example 8.

Specific Rotation $[\alpha]_D$=+2.65° (c=0.55, chloroform; 30° C.)

Nuclear Magnetic Resonance spectrum (TMS standard: $CDCl_3$) (Assignment: ppm: proton number: form: coupling constant)

| aglycon portion | | | |
|---|---|---|---|
| alkylmethyl | 0.87 | 3 H | t |
| methylene | 1.28 | 10 H | m |
| phenyl β-position methylene | 1.56 | 2 H | m |
| acetyl methyl | 1.99–2.18 | 39 H | |
| phenyl α-position methylene | 2.54 | 2 H | t |
| aromatic ring sugar side | 6.87 | 2 H | d |
| aromatic ring alkyl side | 7.07 | 2 H | d |

| Sugar-chain portions (from the portion closest to aglycon) | | | |
|---|---|---|---|
| Glucose ring | | | |
| position 1 | 4.99 | 1 H d | J1,2=7.6 Hz |
| position 2 | 5.15 | 1 H dd | J2,3=9.6 Hz |
| position 3 | 5.25 | 1 H t | J3,4=9.6 Hz |
| position 4 | 3.85 | 1 H t | J4,5=9.6 Hz |
| position 5 | 3.75 | 1 H m | |
| position 6 | 4.07–4.5 | 2 H | |
| Galactose ring | | | |
| position 1 | 4.42 | 1 H d | J1,2=8.0 Hz |
| position 2 | 5.03 | 1 H dd | J2,3=10.4 Hz |
| position 3 | 4.89 | 1 H dd | J3,4=3.2 Hz |
| position 4 | 4.05–4.15 | 1 H | |
| position 5 | 3.64 | 1 H bt | |
| position 6 | 4.05–4.48 | 2 H | |
| Galactose ring | | | |
| position 1 | 4.38 | 1 H d | J1,2=7.6 Hz |
| position 2 | 4.96 | 1 H dd | J2,3=10.4 Hz |
| position 3 | 4.85 | 1 H dd | J3,4=3.2 Hz |
| position 4 | 5.37 | 1 H dd | J4,5≅0.8 Hz |
| position 5 | 3.69 | 1 H bt | |
| position 6 | 4.05–4.48 | 2 H | |
| Galactose ring | | | |
| position 1 | 4.43 | 1 H d | J1,2=7.6 Hz |
| position 2 | 5.20 | 1 H dd | J2,3=10.4 Hz |
| position 3 | 5.00 | 1 H dd | J3,4=3.4 Hz |
| position 4 | 5.37 | 1 H dd | J4,5≅0.8 Hz |
| position 5 | 3.83 | 1 H bt | |
| position 6 | 4.08–4.16 | 2 H | |

Infrared Absorption Spectrum (cm$^{-1}$): Principal Absorption Value 2950, 1755, 1520, 1375, 1240, 1050

EXAMPLE 13

Synthesis of p-n-heptylphenyl β-D-galactopyranosyl-(1→4)-{β-D-galactopyranosyl-( 1→4)}$_2$-β-D-glucopyranoside peracetate 0.744 g (0.54 mmol) of the desired compound was obtained in powdered form from 0.467 g (2.43 mmol) of p-n-heptylphenol and 1.03 g (0.82 mmol) of β-D-galactopyranosyl-(1→4)-{β-D-galactopyranosyl-( 1→4)}$_2$-β-D-glucopyranose peracetate by means of reaction, post-reaction processing, and purification identical to that of Example 8.

Specific Rotation [α]$_D$=+4.33° (c=0.60, chloroform; 33° C.)

Nuclear Magnetic Resonance spectrum (TMS standard: CDCl$_3$) (Assignment: ppm: proton number: form: coupling constant)

| aglycon portion | | | |
|---|---|---|---|
| alkylmethyl | 0.87 | 3 H | t |
| methylene | 1.28 | 8 H | m |
| phenyl β-position methylene | 1.56 | 2 H | m |
| acetyl methyl | 1.99–2.18 | 39 H | |
| phenyl α-position methylene | 2.54 | 2 H | t |
| aromatic ring sugar side | 6.87 | 2 H | d |
| aromatic ring alkyl side | 7.07 | 2 H | d |

| Sugar-chain portions (from the portion closest to aglycon) | | | |
|---|---|---|---|
| Glucose ring | | | |
| position 1 | 4.99 | 1 H d | J1,2=7.6 Hz |
| position 2 | 5.18 | 1 H dd | J2,3=9.6 Hz |
| position 3 | 5.25 | 1 H t | J3,4=9.6 Hz |
| position 4 | 3.85 | 1 H t | J4,5=9.6 Hz |
| position 5 | 3.75 | 1 H m | |
| position 6 | 4.07–4.5 | 2 H | |
| Galactose ring | | | |
| position 1 | 4.42 | 1 H d | J1,2=8.4 Hz |
| position 2 | 5.03 | 1 H dd | J2,3=10.4 Hz |
| position 3 | 4.88 | 1 H dd | J3,4=3.2 Hz |
| position 4 | 4.05–4.15 | 1 H | |
| position 5 | 3.64 | 1 H bt | |
| position 6 | 4.05–4.48 | 2 H | |
| Galactose ring | | | |
| position 1 | 4.38 | 1 H d | J1,2=7.6 Hz |
| position 2 | 4.96 | 1 H dd | J2,3=10.4 Hz |
| position 3 | 4.85 | 1 H dd | J3,4=3.2 Hz |
| position 4 | 4.05–4.15 | 1 H | |
| position 5 | 3.69 | 1 H bt | |
| position 6 | 4.05–4.48 | 2 H | |
| Galactose ring | | | |
| position 1 | 4.43 | 1 H d | J1,2=7.6 Hz |
| position 2 | 5.20 | 1 H dd | J2,3=10.4 Hz |
| position 3 | 5.00 | 1 H dd | J3,4=3.2 Hz |
| position 4 | 5.37 | 1 H dd | J4,5≅0.8 Hz |
| position 5 | 3.83 | 1 H bt | |
| position 6 | 4.08–4.16 | 2 H | |

Infrared Absorption Spectrum (cm$^{-1}$): Principal Absorption Value 2950, 1755, 1520, 1375, 1240, 1050

EXAMPLE 14

Synthesis of p-n-heptyloxyphenyl β-D-galactopyranosyl-(1→4)-{β-D-galactopyronosyl-(1→4)}$_2$-β-D-glucopyranoside peracetate 0.832 g (0.59 mmol) of the desired compound in powdered form was obtained from 0.864 g (4.16 mmol) of p-n-heptyloxyphenol and 1.47 g (1.17 mmol) of β-D-galactopyranosyl-( 1→4)-{β-D-galactopyranosyl-(1→4)}$_2$-β-D-glucopyranose peracetate by means of reaction, post-reaction processing, and refinement identical to that of Example 8.

Specific Rotation [α]$_D$=+2.61° (c=1.12, chloroform; 29° C.)

Nuclear Magnetic Resonance spectrum (TMS standard: CDCl$_3$) (Assignment: ppm: proton number: form: coupling constant)

| aglycon portion | | | |
|---|---|---|---|
| alkylmethyl | 0.89 | 3 H | t |
| methylene | 1.30 | 6 H | m |
| phenoxy γ-position methylene | 1.43 | 2 H | m |
| phenoxy β-position methylene | 1.73 | 2 H | m |
| acetyl methyl | 1.99–2.18 | 39 H | |
| phenoxy α-position methylene | 3.89 | 2 H | |
| aromatic ring sugar side | 6.87 | 2 H | d |

| aromatic ring alkyl side | 7.07 | 2 H | d |

Sugar-chain portions (from the portion closest to aglycon)

Glucose ring

| | | | |
|---|---|---|---|
| position 1 | 4.99 | 1 H d | J1,2=7.6 Hz |
| position 2 | 5.18 | 1 H dd | J2,3=9.6 Hz |
| position 3 | 5.25 | 1 H t | J3,4=9.6 Hz |
| position 4 | 3.85 | 1 H t | J4,5=9.6 Hz |
| position 5 | 3.75 | 1 H m | |
| position 6 | 4.07~4.5 | 2 H | |

Galactose ring

| | | | |
|---|---|---|---|
| position 1 | 4.42 | 1 H d | J1,2=8.4 Hz |
| position 2 | 5.03 | 1 H dd | J2,3=10.4 Hz |
| position 3 | 4.88 | 1 H dd | J3,4=3.2 Hz |
| position 4 | 4.05~4.15 | 1 H | |
| position 5 | 3.64 | 1 H bt | |
| position 6 | 4.05~4.48 | 2 H | |

Galactose ring

| | | | |
|---|---|---|---|
| position 1 | 4.38 | 1 H d | J1,2=7.6 Hz |
| position 2 | 4.96 | 1 H dd | J2,3=10.4 Hz |
| position 3 | 4.85 | 1 H dd | J3,4=3.2 Hz |
| position 4 | 4.05~4.15 | 1 H | |
| position 5 | 3.69 | 1 H bt | |
| position 6 | 4.05~4.48 | 2 H | |

Galactose ring

| | | | |
|---|---|---|---|
| position 1 | 4.43 | 1 H d | J1,2=7.6 Hz |
| position 2 | 5.20 | 1 H dd | J2,3=10.4 Hz |
| position 3 | 5.00 | 1 H dd | J3,4=3.2 Hz |
| position 4 | 5.37 | 1 H dd | J4,5=0.8 Hz |
| position 5 | 3.83 | 1 H bt | |
| position 6 | 4.08~4.16 | 2 H | |

Infrared Absorption Spectrum (cm$^{-1}$): Principal Absorption Value 950, 1755, 1520, 1375, 1230, 1050

EXAMPLE 15

Synthesis of p-1,1,3,3-tetramethylbutylphenyl β-D-galactopyranosyl-(1→4)-{β-D-galactopyranosyl-(1→4)}$_2$-β-D-glucopyranoside peracetate 0.66 g (0.47 mmol) of the desired compound was obtained in powdered form from 0.414 g (2.01 mmol) of p-1,1,3,3-tetramethylbutylphenol and 1.13 g (0.90 mmol) of β-D-galactopyranosyl-(1→4)-{β-D-galactopyranosyl-(1→4)}$_2$-β-D-glycopyranose peracetate in the same manner as in Example 8.

Specific Rotation [α]$_D$=+3.18° (c=0.54, chloroform; 29° C.)

Nuclear Magnetic Resonance spectrum (TMS standard: CDCl$_3$) (Assignment: ppm: proton number: form: coupling constant)

| aglycon portion | | | |
|---|---|---|---|
| alkylmethyl | 0.72 | 9 H | |
| alkylmethyl | 1.33 | 6 H | |
| methylene | 1.70 | 2 H | |
| acetyl methyl | 1.97~2.18 | 39 H | |
| aromatic ring sugar side | 6.88 | 2 H | d |
| aromatic ring alkyl side | 7.26 | 2 H | d |

Sugar-chain portions (from the portion closest to aglycon)

Glucose ring

| | | | |
|---|---|---|---|
| position 1 | 5.01 | 1 H d | J1,2=8.0 Hz |
| position 2 | 5.18 | 1 H dd | J2,3=9.2 Hz |
| position 3 | 5.25 | 1 H t | J3,4=9.2 Hz |

Infrared Absorption Spectrum (cm$^{-1}$): Principal Absorption Value 2980, 1750, 1520, 1375, 1230, 1050

EXAMPLE 16

Synthesis of p-octylphenyl laminaripentaoside[p-octylphenyl β-D-glucopyranosyl-(1→3)-{β-D-glucopyranosyl-(1→3)}$_3$-β-D-glucopyranoside 235 mg of p-octylphenyl laminaripentaoside peracetate (a compound synthesized in the same manner as that of Example 1) and 6.7 ml of a 0.1M sodium methoxide methanol solution were added to 10 ml of methanol and this mixture was agitated for 5.5 hours at room temperature (24° C.). After the completion of the reaction, this was neutralized with 5.5 g of H$^+$-type cation-exchanging resin IR120H$^+$, and the solvent was then removed. 141 mg of crude product was obtained. The product thus obtained was purified by means of reprecipitation with methanol/acetone, and 126 mg of the desired substance was obtained.

$^1$H-NMR (DMSO-d$_6$+D$_2$O) 0.85 ppm CH$_3$, 3H, t, J=6.8 Hz 1.30 (CH$_2$)$_5$, 10H, m 1.53 CH$_2$, 2H, bm 2.53 CH$_2$, 2H 3.08–3.73 Sugar skeleton, 30H 4.40 Sugar skeleton position-1, 1H, d, J=7.6 Hz 4.53 Sugar skeleton position-1, 1H, d, J=7.6 Hz 4.54 Sugar skeleton position-1, 2H, d, J=7.6 Hz 4.91 Sugar skeleton position-1, 1H, d, J=7.6 Hz 6.95 Aromatic group, 2H, d, J=8.4 Hz 7.10 Aromatic group, 2H, d, J=8.4 Hz

EXAMPLE 17

Synthesis of p-pentylphenyl laminaripentaoside[p-pentylphenyl β-D-glucopyranosyl-(1→3)-{β-D-glucopyranosyl-(1→3)}$_3$-β-D-glucopyranoside]

230 mg of p-pentylphenyl laminaripentaoside peracetate (a compound synthesized in the same manner as that of Example 2) and 6.7 ml of a 0.1M sodium methoxide methanol solution were added to 10 ml of methanol, and this mixture was agitated for 5.5 hours at room temperature (24° C.). After the completion of the reaction, this was neutralized with 5.5 g of H$^+$-type cation-exchanging resin IR120H$^+$, and the solvent was then removed. 130 mg of crude product was obtained. The product thus obtained was purified by means of reprecipitation with methanol/acetone, and 120 mg of the desired compound was obtained.

$^1$H-NMR (DMSO-d$_6$+D$_2$O) 0.85 ppm CH$_3$, 3H, t, J=6.8 Hz 1.30 (CH$_2$)$_2$, 4H, m 1.53 CH$_2$, 2H, bm 2.53 CH$_2$, 2H 3.08–3.73 Sugar skeleton, 30H 4.40 Sugar skeleton position-1, 1H, d, J=7.6 Hz 4.53 Sugar skeleton position-1, 1H, d, J=7.6 Hz 4.54 Sugar skeleton position-1, 2H, d, J=7.6 Hz 4.91 Sugar skeleton position-1, 1H, d, J=7.6 Hz 6.95 Aromatic group, 2H, d, J=8.4 Hz 7.10 Aromatic group, 2H, d, J=8.4 Hz

EXAMPLE 18

Synthesis of p-heptyloxyphenyl laminaripentaoside[p-heptyloxyphenyl β-D-glucopyranosyl-(1→3)-{β-D-glucopyranosyl-(1→3)}$_3$-β-D-glucopyranoside]

278 mg of p-heptyloxyphenyl laminaripentaoside peracetate (a compound synthesized in a manner of Example 3) and 7.9 ml of a 0.1M sodium methoxide methanol solution were dissolved in 10 ml of methanol, and 128 mg of the desired compound was obtained by post reaction processing in the manner of Example 16.

$^1$H-NMR (DMSO-$d_6$+$D_2O$) 0.87 ppm $CH_3$, 3H, t, J=6.8 Hz 1.56–1.39 $(CH_2)_4$, 8H, m 1.68 $CH_2$, 2H, bm 3.05–3.92 Sugar skeleton, 30H $CH_2$, 2H 4.40 Sugar skeleton position-1, 1H, d, J=7.6 Hz 4.52 Sugar skeleton position-1, 1H, d, J=8.0 Hz 4.54 Sugar skeleton position-1, 2H, d, J=8.0 Hz 4.83 Sugar skeleton position-1, 1H, d, J=7.6 Hz 6.85 Aromatic group, 2H, d, J=9.2 Hz 6.98 Aromatic group, 2H, d, J=9.2 Hz

EXAMPLE 19

Synthesis of p-octylphenyl laminariheptaoside[p-octylphenyl β-D-glucopyranosyl-(1→3)-{β-D-glucopyranosyl-(1→3)}$_5$-β-D-glucopyranoside]

130 mg of p-octylphenyl laminariheptaoside peracetate (a compound synthesized in the manner of Example 5) and 8 ml of a 0.1M sodium methoxide methanol solution were added to 10 ml of methanol and this was agitated for 5.5 hours at room temperature (24° C.). After the completion of the reaction, this was neutralized with 5.5 g of H$^+$-type cation-exchanging resin IR120H$^+$, and the solvent was removed. The yield was 93 mg of crude product. The product thus obtained was purified by means of reprecipitation with methanol/acetone, and 89 mg of the desired compound was obtained.

$^1$H-NMR (DMSO-$d_6$+$D_2O$) 0.8 5 ppm $CH_3$, 3H, t, J=6.8 Hz 1.30 $(CH_2)_5$, 10H, m 1.53 $CH_2$, 2H, bm 2.53 $CH_2$, 2H 3.08–3.73 Sugar skeleton, 42H 4.40 Sugar skeleton position-1, 1H, d, J=7.6 4.50–4.55 Sugar skeleton position-1, 5H, d, J=7.6 Hz 4.91 Sugar skeleton position-1, 1H, d, J=7.6 Hz 6.95 Aromatic group, 2H, d, J=8.4 Hz 7.10 Aromatic group, 2H, d, J=8.4 Hz

EXAMPLE 20

Synthesis of p-(1,1,3,3-tetramethylbutyl)phenyl laminaripentaoside [p-(1,1,3,3-tetramethylbutyl)phenyl β-D-glucopyranosyl-( 1→3)-{β-D-glucopyranosyl-(1→3)}$_3$-β-D-glucopyranoside]

445 mg of p-(1,1,5,3-tetramethylbutyl}phenyl β-laminaripentaoside peracetate (the compound synthesized in Example 6) and 8.4 ml of a 0.1M sodium methoxide methanol solution were added to 30 ml of methanol, and this was agitated for 7 hours at room temperature (24° C.). After the termination of the reaction, this was neutralized with 8.9 g of H$^+$-type cation-exchanging resin IR-120BH$^+$, the solvent was removed, and this was dried up, 267 mg of the desired compound was obtained.

Specific Rotation $[\alpha]_D$=1.70 (c=O.53, $CH_3OH$, 30° C.)

$^1$H-NMR (DMSO-$d_6$+$H_2O$) 0.69 ppm $CH_3$×3, 9H, S 1.30 $CH_3$×2, 6H, S 1.70 $CH_2$, 2H, s 3.04–3.71 Sugar skeleton, 30H 3.90 Sugar skeleton position-1, 1H, d, J=8.8 Hz 4.52 Sugar skeleton position-1, 1H, d, J=7.2 Hz 4.54 Sugar skeleton position-1, 2H, d, J=7.6 Hz 4.93 Sugar skeleton position-1, 1H, d, J=7.6 Hz 6.95 Aromatic group, 2H, d, J=8.8 Hz 7.29 Aromatic group, 2H, d, J=8.8 Hz

EXAMPLE 21

Synthesis of p-(1,1,3,3-tetramethylbutyl)phenyl laminarioligosaccharide [p-(1,1,3,3-tetramethylbutyl)phenyl β-D-glucopyranosyl-(1→3)-{β-D-glucopyranosyl-(1→3)}m-β-D-glucopyranoside](where m=7~9)

76.5 mg of the p-(1,1,3,3-tetramethylbutyl)phenyl laminarioligosaccharide peracetate obtained in Example 7 and 2 ml of a 0.1M sodium methoxide methanol solution were added to 6 ml of methanol and agitated for 15.5 hours at room temperature (24° C.). After the termination of the reaction, this was neutralized with H$^+$-type cation-exchanging resin IR120H$^+$, and the solution was removed. 46.7 mg of the desired product was obtained.

Infrared Absorption Spectrum, Principal Absorption Values (cm$^{-1}$) 3400, 2900, 1620, 1370, 1160, 1080, 1040

EXAMPLE 22

Synthesis of p-n-octylphenyl β-D-galactopyranosyl-(1→4)-β -D-galactopyranosyl-(1→4)-β-D-glucopyranoside 0.322 g (0.29 mmol) of the p-n-octylphenyl β-D-galactopyranosyl-( 1→4)-β-D-galactopyranosyl-(1→4)-β-D-glucopyranoside peracetate obtained in Example 8 was dissolved in 11 ml of methanol, 4.7 ml of a 0.1N sodium methoxide methanol solution was added to this at room temperature, and this was reacted for 7 hours. After the termination of the reaction, the ion-exchanging resin Amberlite IR120 (H$^+$-type) was added, this was agitated for 1 hour, and 0.191 g (0.28 mmol) of the desired compound was obtained in the powdered form by means of filtering and concentration.

Specific Rotation $[\alpha]_D$=–2.54° (c=0.61, methanol; 32° C.)

Nuclear Magnetic Resonance spectrum (TMS standard: $CD_3OD$) (Assignment: ppm: proton number: form)

| Aglycon portion | | | |
| --- | --- | --- | --- |
| alkylmethyl | 0.89 | 3 H | t |
| methylene | 1.30 | 10 H | m |
| methylene | 1.58 | 2 H | m |
| benzyl-position methylene | 2.54 | 2 H | t |
| aromatic ring oxygen side | 6.99 | 2 H | d |
| aromatic ring alkyl side | 7.07 | 2 H | d |

Sugar-chain portion (ppm: proton number: assignment: form: coupling constant 3.44–4.06 18H 4.40 1H (glucose ring) anomeric position d:7.6 Hz 4.47 1H (galactose ring) anomeric position d:7.6 Hz 4.90 1H (terminal galactose ring) anomeric position d:7.6 Hz Infrared Absorption Spectrum (cm$^{-1}$): Principal Absorption Value 3400, 2950, 1520, 1240, 1080, 1050

EXAMPLE 23

Synthesis of p-n-heptylphenyl β-D-galactopyranosyl-(1→4)-β -D-galactopyranosyl-(1→4)-β-D-glucopyranoside 3.09 g (2.81 mmol) of the p-n-heptylphenyl β -D-galactopyranosyl-(1→4)-β-D-galactopyranosyl-(1→4)-β-D-glucopyranoside peracetate obtained in Example 9 was dissolved in 81 ml of methanol, 42 ml of 0.1N sodium methoxide methanol solution was added to this at room temperature, and this was reacted for 7 hours. After the termination of the reaction, the ion-exchanging resin Amberlite IR120 (H$^+$-type) was added, this was agitated for 1 hour, and 1.88 g (2.78 mmol) of the desired compound was obtained in powdered form by means of filtering and concentration.

Specific Rotation $[\alpha]_D$=–2.04° (c=O.53, methanol; 29° C.)

Nuclear Magnetic Resonance spectrum (TMS standard: $CD_3OD$)

| Aglycon portion (Assignment:ppm:proton number:form) | | | |
|---|---|---|---|
| alkylmethyl | 0.89 | 3 H | t |
| methylene | 1.30 | 8 H | m |
| methylene | 1.58 | 2 H | m |
| benzyl-position methylene | 2.54 | 2 H | t |
| aromatic ring oxygen side | 6.99 | 2 H | d |
| aromatic ring alkyl side | 7.07 | 2 H | d |

Sugar-chain portion (ppm: proton number: assignment: form: coupling constant 3.44–4.06 18H 4.40 1H (glucose ring) anomeric position d:7.6 Hz 4.47 1H (galactose ring) anomeric position d:7.6 Hz 4.90 1H (terminal galactose ring) anomeric position d:7.6 Hz Infrared Absorption Spectrum ($cm^{-1}$): Principal Absorption Value 3400, 2950, 1520, 1240, 1080, 1050

EXAMPLE 24

Synthesis of p-n-heptyloxyphenyl β-D-galactopyranosyl-(1→4)-β-D-galactopyranosyl-(1→4)-β-D-glucopyranoside 2.91 g (2.61 mmol) of the p-n-heptyloxyphenyl β-D-galactopyranosyl-( 1→4)-β-D-galactopyranosyl-(1→4)-β-D-glucopyranoside peracetate obtained in Example 10 was dissolved in 95 ml of methanol, 52 ml of 0.1N sodium methoxide methanol solution was added to this at room temperature, and this was reacted for 11 hours. After the termination of the reaction, the ion-exchange resin Amberlite IR120 ($H^+$-type) was added, this was agitated for 1 hour, and 1.78 g (2.56 mmol) of the desired compound was obtained in powdered form by means of filtering and concentration.

Specific Rotation $[\alpha]_D$=−0.65° (c=0.51: methanol: 30° C.)

Infrared Absorption Spectrum ($cm^{-1}$): Principal absorption values 3400, 2950, 1520, 1230, 1080, 1050

EXAMPLE 25

Synthesis of p-1,1,3,3-tetramethylbutylphenyl β-D-galactopyranosyl-(1→4)-β-D-galactopyranosyl-(1→4)-β-D-glucopyranoside 2.96 g (2.66 mmol) of p-1,1,3,3-tetramethylbutylphenyl β-D-galactopyranosyl-(1→4)-β-D-galactopyranosyl-(1→4)-β-D-glucopyranoside peracetate obtained in Example 11 was dissolved in 78 ml of methanol, 40.4 ml of a 0.1N sodium methoxide methanol solution was added to this at room temperature and this was reacted for 7 hours. After the termination of the reaction, the ion-exchanging resin Amberlite IR120 ($H^+$-type) was added, this was agitated for 1 hour, and 1.84 g (2.65 mmol) of the desired compound was obtained in powdered form by means of filtering and concentration, Specific Rotation $[\alpha]_D$=−3.57° (c=0.55, methanol; 29° C.)

Nuclear Magnetic Resonance spectrum (TMS standard: $CD_3OD$)

| Aglycon portion (Assignment:ppm:proton number:form) | | | |
|---|---|---|---|
| alkylmethyl | 0.71 | 9 H | s |
| alkylmethyl | 1.34 | 6 H | s |
| methylene | 1.75 | 2 H | s |
| aromatic ring oxygen side | 7.00 | 2 H | d |
| aromatic ring alkyl side | 7.28 | 2 H | d |

Sugar-chain portion (ppm: proton number: assignment: form: coupling constant 3.47–4.06 18H 4.41 1H (glucose ring) anomeric position d:7.6 Hz 4.47 1H (galactose ring) anomeric position d:7.6 Hz 4.91 1H (terminal galactose ring) anomeric position d:7.6 Hz Infrared Absorption Spectrum ($cm^{-1}$): Principal Absorption Value 3400, 2980, 1520, 1240, 1080, 1050

EXAMPLE 26

Synthesis of p-n-octylphenyl β-D-galactopyranosyl-(1→4)-{β -D-galactopyranosyl-(1→4)}$_2$-β-D-glucopyranoside 1.09 g (0.78 mmol) of the p-n-octylphenyl β -D-galactopyranosyl-(1→4)-{β-D-galactopyranosyl-(1→4)}$_2$-β -D-glucopyranoside peracetate obtained in Example 12 was dissolved in 26 ml of methanol, 15.5 ml of 0.1N sodium methoxide methanol solution was added to this at room temperature, and this was reacted for 7 hours. After the termination of the reaction, the ion-exchanging resin Amberlite IR120 ($H^+$-type) was added, this was agitated for 1 hour, and 0.643 g (0.75 mmol) of the desired compound was obtained in powdered form by means of filtration and concentration.

Specific Rotation $[\alpha]_D$=+8.96° (c=0.52, methanol; 28° C.)

Nuclear Magnetic Resonance spectrum (TMS standard: $CD_3OD$)

| Aglycon portion (Assignment:ppm:proton number:form) | | | |
|---|---|---|---|
| alkylmethyl | 0.88 | 3 H | t |
| methylene | 1.29 | 10 H | m |
| methylene | 1.57 | 2 H | m |
| methylene | 2.54 | 2 H | m |
| aromatic ring oxygen side | 6.98 | 2 H | d |
| aromatic ring alkyl side | 7.08 | 2 H | d |

Sugar-chain portion (ppm: proton number: assignment: form: coupling constant 3.47–4.06 24H 4.40 1H (glucose ring) anomeric position d:7.6 Hz 4.45 1H (galactose ring) anomeric position d:7.6 Hz 4.47 1H (galactose ring) anomeric position d:7.6 Hz 4.89 1H (terminal galactose ring) anomeric position d:7.6 Hz Infrared Absorption Spectrum ($cm^{-1}$): Principal Absorption Value 3400, 2950, 1520, 1240, 1080, 1050

EXAMPLE 27

Synthesis of p-n-heptylphenyl β-D-galactopyranosyl-(1→4)-{β -D-galactopyranosyl-(1→4)}$_2$-β-D-glucopyranoside 0.326 g (0.24 mmol) of the p-n-heptylphenyl β -D-galactopyranosyl-(1→4)-{β-D-galactopyranosyl-(1→4)}$_2$-β -D-glucopyranoside peracetate obtained in Example 13 was dissolved in 8.6 ml of methanol, 4.7 ml of 0.1N sodium methoxide methanol solution was added to this at room temperature and this was reacted for 7 hours. After the termination of the reaction, the ion-exchanging resin Amberlite IR120 ($H^+$-type) was added, this was agitated for 1 hour, and 0.192 g (0.23 mmol) of the desired compound was obtained in powdered form by means of filtration and concentration.

Specific Rotation $[\alpha]_D$=+11.1° (c=0.57, methanol; 29° C.)

Nuclear Magnetic Resonance spectrum (TMS standard: $CD_3OD$)

| Aglycon portion (Assignment:ppm:proton number:form) | | | |
|---|---|---|---|
| alkylmethyl | 0.89 | 3 H | t |
| methylene | 1.29 | 8 H | m |
| methylene | 1.57 | 2 H | m |
| methylene | 2.54 | 2 H | m |
| aromatic ring oxygen side | 6.98 | 2 H | d |
| aromatic ring alkyl side | 7.08 | 2 H | d |

Sugar-chain portion (ppm: proton number: assignment: form: coupling constant 3.47–4.06 24H 4.40 1H (glucose ring) anomeric position d:7.6 Hz 4.45 1H (galactose ring) anomeric position d:7.6 Hz 4.47 1H (galactose ring) anomeric position d:7.6 Hz 4.89 1H (terminal galactose ring) anomeric position d:7.6 Hz Infrared Absorption Spectrum (cm$^{-1}$): Principal Absorption Value 3400, 2950, 1520, 1240, 1080, 1050

EXAMPLE 28

Synthesis of p-n-heptyloxyphenyl β-D-galactopyranosyl-(1→4){β-D-galactopyranosyl-(1→4)}$_2$-β-D-glucopyranoside 0.555 g (0.40 mmol) of the p-n-heptyloxyphenyl β-D-galactopyranosyl-(1→4)-{β-D-galactopyranosyl-(1→4)}$_2$-β-D-glucopyranoside peracetate obtained in Example 14 was dissolved in 14 ml of methanol, 7.8 ml of 0.1N sodium methoxide methanol solution was added at room temperature and this was reacted for 16 hours. After the termination of the reaction, the ion-exchanging resin Amberlite IR 120 (H$^+$-type) was added, this was agitated for 1 hour, and 0.311 g (0.36 mmol) of the desired compound was obtained in powdered form by means of filtration and concentration.

Specific Rotation $[\alpha]_D$=+15.8° (c=0.68, methanol; 30° C.)

Infrared Absorption Spectrum (cm$^{-1}$): Principal Absorption Value 3400, 2950, 1520, 1230, 1080, 1050

EXAMPLE 29

Synthesis of p-1,1,3,3-tetramethylbutylphenyl β-D-galactopyranosyl-(1→4)-{β-D-galactopyranosyl-(1→4)}$_2$-β-D-glucopyranoside 0.567 g (0.41 mmol) of the p-1,1,3,3-tetramethylbutylphenyl β-D-galactopyranosyl-(1→4)-{β-D-galactopyranosyl-(1→4)}$_2$-β-D-glucopyranoside peracetate obtained in Example 15 was dissolved in 14 ml of methanol, 8 ml of a 0.1N sodium methoxide methanol solution was added at room temperature, and this was reacted for 7 hours. After the termination of the reaction, the ion-exchanging resin Amberlite IR120 (H$^+$-type) was added, this was agitated for 1 hour, and 0.343 g (0.40 mmol) of the desired compound was obtained in a powdered form by means of filtration and concentration.

Specific Rotation $[\alpha]_D$=+9.4° (c=0.58, methanol; 29° C.)

Nuclear Magnetic Resonance spectrum (TMS standard: CD$_3$OD)

| Aglycon portion (Assignment:ppm:proton number:form) | | | |
|---|---|---|---|
| alkylmethyl | 0.71 | 9 H | s |
| alkylmethyl | 1.34 | 6 H | s |
| methylene | 1.75 | 2 H | s |
| aromatic ring oxygen side | 7.00 | 2 H | d |
| aromatic ring alkyl side | 7.30 | 2 H | d |

Sugar-chain portion (ppm: proton number: assignment: form: coupling constant 3.47–4.06 24H 4.41 1H (glucose ring) anomeric position d:7.6 Hz 4.45 1H (galactose ring) anomeric position d:7.6 Hz 4.47 1H (galactose ring) anomeric position d:7.6 Hz 4.91 1H (terminal galactose ring) anomeric position d:7.6 Hz Infrared Absorption Spectrum (cm$^{-1}$): Principal Absorption Value 3400, 2980, 1520, 1240, 1080, 1050

EXAMPLE 30

Synthesis of p-octylphenyl laminaripentaoside sulfate [p-octylphenyl β-D-glucopyranosyl-(1→3)-{β-D-glucopyranosyl (1→3)}$_3$-β-D-glucopyranoside sulfate]

100 mg of the compound synthesized in Example 16 and 530 mg of sulfur trioxide pyridine complex were dissolved in 10 ml of dehydrated pyridine, agitated for 6 hours in an atmosphere of nitrogen gas at a temperature of 80° C. After the temperature thereof was returned to room temperature, the precipitate and upper layer were separated. 5 ml of water was added to the precipitate, and this was agitated for 30 minutes, and the hydrogen ion concentration was adjusted to approximately 10 using 1N sodium hydroxide aqueous solution. This solution was concentrated under reduced pressure and dried up. The residue was dissolved in 5 ml of ion-exchanged water, and desalted with a 'alkuroashiraiza' (a desalting apparatus produced by Asahi Chemical Industries). After desalting, acetone was added to this aqueous solution, and the desired compound was precipitated. 210 mg of the desired product was obtained after the precipitate was filtered and dried up.

Specific Rotation $[\alpha]_D$=−7.5° (c=0.61, water; 28° C.)

Infrared Absorption Spectrum (Principal Absorption Values, cm$^{-1}$) 3500, 2950, 2890, 1640, 1250, 1030, 1000, 820, 620 Sulfation ratio: Analysis showed that 88% of all hydroxyl groups were sulfated.

EXAMPLE 31

Synthesis of p-pentylphenyl laminaripentaoside sulfate [p-pentylphenyl β-D-glucopyranosyl-(1→3)-{β-D-glucopyranosyl (1→3)}$_3$-β-D-glucopyranoside sulfate]

100 mg of the compound synthesized in Example 17, was subjected to sulfation, post-processing, and purification in a similar manner to that of Example 30, and 190 mg of the desired compound was obtained.

Specific Rotation $[\alpha]_D$=−7.9° (c=0.52, water; 28° C.)

Infrared Absorption Spectrum Principal Absorption Values cm$^{-1}$ 3500, 2950, 2890, 1640, 1250, 1030, 1000, 820, 620 Sulfation ratio: Analysis showed that 87% of all hydroxyl groups were sulfated.

EXAMPLE 32

Synthesis of sulfated p-heptyloxyphenyl laminaripentaoside {sulfated p-heptyloxyphenyl β-D-glucopyranosyl-(1→3)-{β-D-glucopyranosyl-(1→3)}$_3$-β-D-glucopyranoside]

100 mg of the compound synthesized in Example 18 was subjected to sulfation, post-processing, and purification in the manner of Example 30, and 175 mg of the desired compound was obtained.

Specific Rotation $[\alpha]_D$=−8.8° (c=0.55, water; 28° C.)

Infrared Absorption Spectrum Principal Absorption Values cm$^{-1}$ 3500, 2950, 2890, 1640, 1240, 1040, 990, 820, 620 Sulfation ratio: Analysis showed that 84% of all hydroxyl groups were sulfated.

EXAMPLE 33

Synthesis of p-heptyloxyphenyl laminaripentaoside sulfate [p-heptyloxyphenyl β-D-glucopyranosyl-(1→3)-{β-D-glucopyranosyl-(1→3)}$_3$-β-D-glucopyranoside sulfate] (alternate method of Example 32)

100 mg of the compound synthesized in Example 18 was sulfated in the similar manner of Example 30, the hydrogen ion concentration thereof was adjusted to approximately 10 using 1N sodium hydroxide aqueous solution, and this was then concentrated and dried up under reduced pressure. This residue was then dissolved in 4 ml of water, this was desalinated by passing it through a dextran gel column (Cefodex G-25), and after concentration of the desired fraction, this was dissolved in 6 ml of water, ethanol was added, and the desired compound was precipitated. 166 mg of the desired compound was obtained after the precipitate was filtered and dried up.

Specific Rotation $[\alpha]_D = -8.7°$ (c=0.52, water; 28° C.)

Infrared Absorption Spectrum (Principal Absorption Values cm$^{-1}$) 3500, 2950, 2890, 1640, 1240, 1040, 990, 820, 620 Sulfation ratio: Analysis showed that 81% of all hydroxyl groups were sulfated.

EXAMPLE 34

Synthesis of p-octylphenyl laminaripentaoside sulfate [p-octylphenyl β-D-glucopyranosyl-(1→3)-{β-D-glucopyranosyl (1→3)}$_5$-β-D-glucopyranoside sulfate]

50 mg of the compound synthesized in Example 19 and 260 mg of a sulfur trioxide pyridine complex were dissolved in 10 ml of dehydrated pyridine, this was agitated for 6 hours at a temperature of 80° C. in an atmosphere of nitrogen gas. After returning the temperature of the mixture to room temperature, the precipitate and upper layer were separated, 5 ml of water was added to the precipitate, this was agitated for 30 minutes, and then the hydrogen ion concentration was adjusted to approximately 10 using a 1N sodium hydroxide aqueous solution. This solution was concentrated under reduced pressure and dried up, dissolved in 5 ml of ion-exchanged water, and desalinated with a 'Maikuroashiraiza' (a desalinization apparatus made by Asahi Chemical Industries). After desalinization, acetone was added to this aqueous solution and the desired compound was precipitated, and 110 mg of the desired compound was obtained after the precipitate was filtered and dried up.

Specific Rotation $[\alpha]_D = -9.5°$ (c=0.60, water; 28° C.)

Infrared Absorption Spectrum (Principal Absorption Values cm$^{-1}$) 3500, 2950, 2890, 1640, 1250, 1030, 1000, 820, 620 Sulfation ratio: Analysis showed that 81% of all hydroxyl groups were sulfated.

EXAMPLE 35

Synthesis of p-(1,1,3,3-tetramethylbutyl)phenyl laminaripentaoside sulfate [p-(1,1,3,3-tetramethylbutyl)phenyl β-D-glucopyranosyl-(1→3)-{β-D-glucopyranosyl-(1→3)}$_3$-β-D-glucopyranoside sulfate]

162 mg (0.160 mmol) of the compound synthesized in Example 20 was dissolved in 10 ml of dehydrated pyridine and concentrated under reduced pressure at 45° C. After this, the same process, namely adding 10 ml of dehydrated pyridine to the residue and concentrating under reduced pressure, was repeated further 2 times. The resulting residue was dissolved in 10 ml of dehydrated pyridine and heated to a temperature of 85° C. in an atmosphere of nitrogen gas. 813 mg of a sulfur trioxide pyridine complex was added to this, and this was agitated for 1.5 hours. The reaction mixture was cooled to the room temperature and the syrup layer and pyridine layer were separated, the syrup layer was dissolved in 20 ml of distilled water, and this was neutralized to a hydrogen ion concentration of 7.2 by means of 8.0 ml of a saturated aqueous solution of barium hydroxide. Centrifugal separation was then conducted and excess barium sulfate was precipitated. The clear supernatant was then passed through an ion-exchanging resin column (IR-120BNa$^+$) and ion-exchanged. This aqueous solution was concentrated to 4 ml, filtered with a 0.22 μm membrane filter, concentrated and dried up. This crude reaction product was then dissolved in 0.8 ml of distilled water, and purified by reprecipitation with 50 ml of acetone. This was then again dissolved in distilled water, the hydrogen ion concentration thereof was adjusted to 6.9 by means of a 0.2N aqueous solution of hydrochloric acid, and 221 mg of the desired compound was obtained by means of freeze-drying.

Specific Rotation $[C\alpha]_D = -13.2°$ (c=1.03, water, 26° C.)

Infrared Absorption Spectrum (Principal Absorption Values cm$^{-1}$) 3500, 2950, 2890, 1640, 1250, 1030, 990, 820, 620 Sulfation ratio: Analysis showed that 93% of all hydroxyl groups were sulfated.

EXAMPLE 36

Synthesis of p-heptyloxyphenyl laminaripentaoside sulfate [p-heptyloxyphenyl β-D-glucopyranosyl-(1→3)-{β-D-glucopyranosyl (1→3)}$_3$-β-D-glucopyranoside sulfate] (alternate method of Example 32)

200 mg (0.200 mmol) of the compound synthesized in Example 18 was dissolved in dehydrated pyridine, and the solvent was removed, three times of those adding solvent and removing solvent in the similar manner of Example 35, and then reduced-pressure drying up was conducted. This was then dissolved in 10 ml of dehydrated pyridine, and heated to a temperature of 85° C. in an atmosphere of nitrogen gas. 1.000 g (6.3 mmol) of sulfur trioxide pyridine complex was added, and this was agitated and reacted for 1.5 hours. After the temperature of the reaction mixture was returned to room temperature, the syrup layer and pyridine layer were separated, the syrup layer was dissolved in 10 ml of distilled water, and this was neutralized to a hydrogen ion concentration of 7.2 by means of 11.3 ml of a saturated aqueous solution of barium hydroxide. Excess barium sulfate was precipitated by means of centrifugal separation. The clear supernatant thereof was then filtered through a 0.22 μm membrane filter, 50 ml of ion-exchanging resin (IR-120BNa$^+$) was added, and this was agitated and ion-exchanged for 30 minutes. After the resin was separated by filtration, the aqueous solution was concentrated to 3 ml and reprecipitation purification was carried out using 100 ml of acetone. This was then dissolved in distilled water, the hydrogen ion concentration was adjusted to 6.8 by means of a 0.2N aqueous solution of hydrochloric acid, and 339 mg of the desired compound was obtained by means of freeze-drying.

Specific Rotation-$[\alpha]_D = -15.9°$ (c=0.92, water, 26° C.)

Infrared Absorption Spectrum (Principal Absorption Values cm$^{-1}$) 3500, 2950, 2890, 1640, 1240, 1040, 990, 820, 620 Sulfation ratio: Analysis showed that 92% of all hydroxyl groups were sulfated.

EXAMPLE 37

Synthesis of p-octylphenyl laminaripentaoside sulfate [p-octylphenyl β-D-glucopyranosyl-(1→3)-{β-D-glucopyranosyl (1→3)}$_3$-β-D-glucopyranoside sulfate] (alternate method of Example 30)

162 mg (0.160 mmol) of the compound synthesized in Example 16 was, as in Example 35, dissolved in 10 ml of dehydrated pyridine, the dissolving and concentrating process was repeated three times, and finally drying up was conducted. The residue was dissolved in 10 ml of dehydrated pyridine, and heated to a temperature of 85° C. in an atmosphere of nitrogen gas. 813 mg of sulfur trioxide pyridine complex was added to this, and this was agitated and reacted for 1.5 hours. After the temperature of the reaction mixture was returned to room temperature, the syrup layer and pyridine layer were separated. The syrup layer was dissolved in 20 ml of distilled water, and then neutralized to a hydrogen ion concentration of 7.2 by means of 8.0 ml of a saturated aqueous solution of barium hydroxide. The excess barium sulfate was precipitated by means of centrifugal separation. The clear supernatant thereof was passed through an ion-exchanging resin column (IR-120BNa$^+$), and thus ion-exchanged. This aqueous solution was then concentrated to 4 ml, filtered through a 0.22 μm membrane filter, and concentrated and dried up. This crude reaction product was dissolved in 0.8 ml of distilled water, and purified by means of reprecipitation with 50 ml of acetone. The precipitate was dissolved in distilled water, adjusted to a hydrogen ion concentration of 6.9 by means of a 0.2N aqueous solution of hydrochloric acid, and 221 mg of the desired compound was obtained by freeze-drying.

Specific Rotation $[\alpha]_D = -14.9°$ (c=1.02, water, 26° C.)

Infrared Absorption Spectrum (Principal Absorption Values cm$^{-1}$) 3500, 2950, 2890, 1640, 1250, 1030, 1000, 820, 620 Sulfation ratio: Analysis showed that 91% of all hydroxyl groups were sulfated.

EXAMPLE 38

Synthesis of p-(1,1,3,3-tetramethylbutyl)phenyl laminarioligosaccharide sulfate [p-(1,1,3,3-tetramethylbutyl)phenyl β-D-glucopyranosyl-(1→3)-{β-D-glucopyranosyl-(1→3)}$_m$-β-D-glucopyranoside sulfate] (where m=7–9)

46.7 mg of the compound synthesized in Example 21 was treated 4 times of dissolving and concentrating in the similar manner of Example 35 by means of 5 ml of dehydrated pyridine. The residue was dissolved in 3 ml of dehydrated pyridine, and heated to temperature of 83° C. in an atmosphere of argon gas, 263 mg (1.65 mmol) of sulfur trioxide pyridine complex was then added, and this was agitated and reacted for 1.5 hours. The precipitate formed by returning the mixture to room temperature was separated. 10 ml of water was added to this precipitate, this was agitated for 30 minutes, and the hydrogen ion concentration was adjusted to approximately 7.5 by means of 3.3 ml of a saturated aqueous solution of barium hydroxide. The formed precipitate was removed by means of centrifugal separation, this solution was then passed through a Na$^+$-type cation-exchanging resin IR120B column, and ion-exchanging was conducted. The eluted fraction was concentrated, and 96.3 mg of a crude product was obtained. This was dissolved in a small amount of water, acetone was added, and 89.1 mg of the desired compound was obtained by precipitation, filtering, and drying.

Specific Rotation $[\alpha]_D = -15.1°$ (c=0.51, water, 29° C.)

Infrared Absorption Spectrum (Principal Absorption Values cm$^{-1}$) 3500, 2950, 2900, 1640, 1250, 1060, 1000, 820, 580 Sulfation ratio: Analysis showed that 91% of all hydroxyl groups were sulfated.

EXAMPLE 39

Synthesis of octylphenyl β-D-galactopyranosyl-(1→4)-{β-D-galactopyranosyl-(1→4)}$_2$-β-D-glucopyranoside sulfate 0.305 g (0.36 mmol) of octylphenyl β-D-galactopyranosyl (1→4)-{β-D-galactopyranosyl-(1→4)}$_2$-β-D-glucopyranoside and 1.47 g (9.27 mmol) of sulfur trioxide pyridine complex were dissolved in 15 ml of dehydrated pyridine and reacted for 1.5 hours at a temperature of 83° C. in an atmosphere of nitrogen gas. Precipitate formed after the reaction was separated from the pyridine, to this precipitate was added 4 ml of water at room temperature, this was agitated for 1 hour, the hydrogen ion concentration was adjusted to 7.5–8.0 in a 1N sodium hydroxide aqueous solution, and this was then concentrated under reduced pressure. A small amount of water was added, a large amount of ethanol was then added while agitating, and 1.06 g of crude precipitate was obtained. Of this precipitate, 0.4 g was dissolved in water, desalinized by means of a 'Maikuroashiraiza' (Asahi Chemical Industries), reprecipitation was conducted with a large amount of acetone, and after drying, 0.30 g of the desired compound was obtained.

Specific Rotation $[\alpha]_D = -0.42°$ (c=0.61, water, 28° C.)

Infrared Absorption Spectrum (Principal Absorption Values cm$^{-1}$) 3500, 2950, 2890, 1640, 1250, 1030, 1000, 820, 620 Sulfation ratio: Analysis showed that 86% of all hydroxyl groups were sulfated.

EXAMPLE 40

Synthesis of octyloxyphenyl β-D-galactopyranosyl-(1→4)-{β-D-galactopyranosyl-(1→4)}$_2$-β-D-glucopyranoside sulfate 0.30 g (0.34 mmol) of octyloxyphenyl β-D-galactopyranosyl (1→4)-{β-D-galactopyranosyl-(1→4)}$_2$-β-D-glucopyranoside and 1.47 g (9.27 mmol) of sulfur trioxide pyridine complex was dissolved in 16 ml of dehydrated pyridine and reacted for 2.5 hours at a temperature of 83° C. in an atmosphere of nitrogen gas. Precipitate was separated from the pyridine, to this was added 4 ml of water at room temperature, this was agitated for 1 hour, the hydrogen ion concentration was adjusted to 7.5–8.0 in a 1N sodium hydroxide aqueous solution, and this was then concentrated under reduced pressure. A small amount of water was added, a large amount of ethanol was then added while agitating, and 1.03 g of crude precipitate was formed. 0.4 g thereof was purified in the similar manner of Example 39, and 0.32 g of the desired compound was obtained.

Specific Rotation $[\alpha]_D = -0.56°$ (c=0.60, water, 28° C.)

Infrared Absorption Spectrum (Principal Absorption Values cm$^{-1}$) 3500, 2950, 2890, 1640, 1240, 1040, 990, 820, 620 Sulfation ratio: Analysis showed that 84% of all hydroxyl groups were sulfated.

EXAMPLE 41

Synthesis of octyloxyphenyl β-D-galactopyranosyl-(1→4)-β-D-galactopyranosyl-(1→4)-β-D-glucopyranoside sulfate 0.30 g Of octyloxyphenyl β-D-galactopyranosyl (1→4)-β-D-galactopyranosyl-(1→4)-β-D-glucopyranoside was reacted and purified in the similar manner of Example 39, and 0.89 g residue was obtained. This was desalinized by means of a 'Maikuroashiraiza' (Asahi Chemical Industries), in the similar manner of Example 39, and 0.32 g of the desired compound was obtained.

Specific Rotation $[\alpha]_D = -0.96°$ (c=0.50, water, 28° C.)

Infrared Absorption Spectrum (Principal Absorption Values cm$^{-1}$) 3500, 2950, 2890, 1640, 1240, 1040, 1000, 820, 620 Sulfation ratio: Analysis showed that 89% of all hydroxyl groups were sulfated.

EXAMPLE 42

Synthesis of heptyloxyphenyl β-D-galactopyranosyl-(1→4)-{β -D-galactopyranosyl-(1→4)}$_2$-β-D-glucopyranoside sulfate 0.31 g of heptyloxyphenyl β-D-galactopyranosyl (1→4)-{β-D-galactopyranosyl-(1→4)}$_2$-β-D-glucopyranoside was dissolved in 7.5 ml of dimethyl formamide and this was heated to a temperature of 50° C. in an atmosphere of argon gas. 1.5 g of sulfur trioxide pyridine complex was added to this, this was reacted for 6 hours, and the reaction liquid was concentrated under reduced pressure. A small amount of water was added thereto, the hydrogen ion concentration was adjusted to 9.5 in 1N sodium hydroxide aqueous solution, the solution was concentrated under reduced pressure, and 1.66 g of a crude product was obtained. Of this, 0.62 g was purified in the similar manner of Example 39, and 0.37 g of the desired compound was obtained.

Specific Rotation $[\alpha]_D = -0.51°$ (c=0.54, water, 28° C.)

Infrared Absorption Spectrum (Principal Absorption Values cm$^{-1}$) 3500, 2950, 2890, 1640, 1240, 1060, 1020, 820, 620 Sulfation ratio: Analysis showed that 80% of all hydroxyl groups were sulfated.

EXAMPLE 43

Synthesis of p-(1,1,3,3-tetramethylbutyl)phenyl β -D-galactopyranosyl-(1→4)-{β-D-galactopyranosyl-(1→4)}$_2$-β -D-glucopyranoside sulfate 0.34 g of p-(1,1,3,3-tetramethylbutyl)phenyl β -D-galactopyranosyl-(1→4)-{β-D-galactopyranosyl-(1→4)}$_2$-β -D-glucopyranoside was subjected to reaction and purification as the similar manner in Example 42, and 1.71 g of a crude product was thereby obtained. Of this, 0.56 g was purified in the similar manner of Example 39, and 0.24 g of the desired compound was obtained.

Specific Rotation $[\alpha]_D = -0.1°$ (c=0.51, water, 30° C.)

Infrared Absorption Spectrum (Principal Absorption Values cm$^{-1}$) 3500, 2950, 2890, 1660, 1510, 1240, 1060, 1010, 820, 620 Sulfation ratio: Analysis showed that 87% of all hydroxyl groups were sulfated.

EXAMPLE 44

Anti-AIDS (HIV) Activity

Evaluation method: Test substances having various concentrations were placed in a 96-well microtiter plate along with HIV-infected MT-4 cells (2.5×10$^4$/well, MOI: 0.01) immediately after the infection thereof. In order to ascertain the cytotoxicity of the test substance with respect to the MT-4 cells, non-infected cells were cultured in an identical manner along with the test substances of various concentrations. After culturing for 5 days at a temperature of 37° C. in a $CO_2$ incubator, the number of living cells was determined using the MTT method. The antiviral activity is shown in terms of the concentration which prevented 50% of the cytopathogenic effects of the HIV virus ($EC_{50}$: 50% effective concentration) and the cytotoxicity is shown in terms of the concentration at which the cytotoxicity of the test substance reaches 50% ($CC_{50}$: 50% cytotoxic concentration). Furthermore, the selectivity index (S.I.) is calculated as $CC_{50}/EC_{50}$.

(Reference: Pauwels, et al., J. Viral Methods, 20 (1988) 309–321). Using this method, the compounds of Examples 30–43 were tested for anti-HIV activity. The results thereof are shown in Table 1 and Table 2. The compounds shown in Table 2 (Examples 35–38) are produced by means of novel sulfation methods. For the purposes of comparison, the conventional anti-AIDS agents AZT (3'-azido-2',3'-dideoxythymidine) and dextran sulfate were also tested, and the results thereof are appended as comparative data.

TABLE 1

| Example Number | $CC_{50}$ (μg/ml) | $EC_{50}$ (μg/ml) | SI |
| --- | --- | --- | --- |
| 30 | >1000 | 0.62 | >1612 |
| 31 | >1000 | 0.75 | >1333 |
| 32 | >1000 | 0.72 | >1389 |
| 33 | >1000 | 0.77 | >1298 |
| 34 | >1000 | 0.31 | >3226 |
| 39 | >1000 | 0.82 | >1219 |
| 40 | >1000 | 0.95 | >1052 |
| 41 | >1000 | 1.12 | >892 |
| 42 | >1000 | 0.23 | >4348 |
| 43 | >1000 | 0.04 | >25000 |

TABLE 2

| Example Number | $CC_{50}$ (μg/ml) | $EC_{50}$ (μg/ml) | SI |
| --- | --- | --- | --- |
| 35 | >1000 | 0.038 | >26300 |
| 36 | >1000 | 0.062 | >16100 |
| 37 | >1000 | 0.080 | >12500 |
| 38 | >1000 | 0.020 | >45400 |
| AZT[1] | 10.8 | 0.004 | 2700 |
| dextran sulfate | >1000 | 0.50 | 2000 |

[1]AZT $CC_{50}$ and $EC_{50}$ units are μM.

Production examples of the anti-viral agent of the present invention are described below.

(Agent Production Example 1)

| | |
| --- | --- |
| Compound of Example 30 | 50 mg |
| Starch | 30 mg |
| Lactose | 110 mg |
| Talc | 7 mg |
| Magnesium stearate | 3 mg |
| | 200 mg |

The compound of Example 30 was ground and lactose and starch were added to this and mixed. 10% of starch paste was added to the above mixture and this was agitated until granules formed. The granules were dried and sieved, talc and magnesium stearate were mixed in, and the mixture was processed by the ordinary method to prepare a 200 mg tablet.

(Agent Production Example 2)

| | |
| --- | --- |
| Compound of Example 31 | 50 mg |
| Starch | 30 mg |
| Lactose | 110 mg |
| Talc | 7 mg |

(Agent Production Example 2)

| | |
|---|---|
| Magnesium stearate | 3 mg |
| | 200 mg |

Using the compound of Example 31, mixing, granulation, and tablettization were performed in the similar manner of Production Example 1 to prepare a 200 mg tablet.

(Agent Production Example 3)

| | |
|---|---|
| Compound of Example 32 | 50 mg |
| Starch | 30 mg |
| Lactose | 110 mg |
| Talc | 7 mg |
| Magnesium stearate | 3 mg |
| | 200 mg |

Using the compound of Example 32, mixing, granulation, and tablettization were performed in the similar manner of Production Example 1 to prepare a 200 mg tablet.

(Agent Production Example 4)

| | |
|---|---|
| Compound of Example 39 | 50 mg |
| Starch | 30 mg |
| Lactose | 110 mg |
| Talc | 7 mg |
| Magnesium stearate | 3 mg |
| | 200 mg |

Using the compound of Example 39, mixing, granulation, and tablettization were performed in the similar manner of Production Example 1 to prepare a 200 mg tablet.

(Agent Production Example 5)

| | |
|---|---|
| Compound of Example 40 | 50 mg |
| Starch | 30 mg |
| Lactose | 110 mg |
| Talc | 7 mg |
| Magnesium stearate | 3 mg |
| | 200 mg |

Using the compound of Example 40, mixing, granulation, and tablettization were performed in the similar manner of Production Example 1 to prepare a 200 mg tablet.

(Agent Production Example 6)

| | |
|---|---|
| Compound of Example 41 | 50 mg |
| Starch | 30 mg |
| Lactose | 110 mg |
| Talc | 7 mg |
| Magnesium stearate | 3 mg |
| | 200 mg |

Using the compound of Example 41, mixing, granulation, and tablettization were performed in the similar manner of Production Example 1 to prepare a 200 mg tablet.

(Agent Production Example 7)

| | |
|---|---|
| Compound of Example 33 | 25 mg |
| Lactose | 50 mg |
| Starch | 23 mg |
| Magnesium stearate | 2 mg |
| | 100 mg |

25 mg of the compound of Example 33 was ground, lactose, starch, and magnesium stearate were added, this was sufficiently mixed, and then placed in a capsule.

(Agent Production Example 8)

| | |
|---|---|
| Compound of Example 34 | 25 mg |
| Lactose | 50 mg |
| Starch | 23 mg |
| Magnesium stearate | 2 mg |
| | 100 mg |

25 mg of the compound of Example 34 was ground, lactose, starch, and magnesium stearate were added, this was sufficiently mixed, and then placed in a capsule.

(Agent Production Example 9)

| | |
|---|---|
| Compound of Example 41 | 50 mg |
| Lactose | 50 mg |
| Starch | 23 mg |
| Magnesium stearate | 2 mg |
| | 100 mg |

25 mg of the compound of Example 41 was ground, lactose, starch, and magnesium stearate were added, this was sufficiently mixed, and then placed in a capsule.

(Agent Production Example 10)

Physiological saline that had been sterilized in an autoclave was added to 500 mg of the compound of Example 30 to dissolve the compound therein, and the total amount thereof was adjusted to 10 ml. The mixture was then transferred into a dry-sterilized ampule.

(Agent Production Example 11)

500 mg of the compound of Example 31 was dissolved in a physiological saline solution, processing was conducted in the manner of Agent Production Example 10, and 10 ml of the agent was prepared.

(Agent Production Example 12)

600 mg of the compound of Example 32 was dissolved in a physiological saline solution, processing was conducted in the similar manner of Agent Production Example 10, and 10 ml of the liquid agent was prepared.

(Agent Production Example 13)

600 mg of the compound of Example 33 was dissolved in a physiological saline solution, processing was conducted in the similar manner of Agent Production Example 10, and 10 ml of the liquid agent was prepared.

(Agent Production Example 14)

600 mg of the compound of Example 34 was dissolved in a physiological saline solution, processing was conducted in the similar manner of Agent Production Example 10, and 10 ml of the liquid agent was prepared.

(Agent Production Example 15)

500 mg of the compound of Example 39 was dissolved in a physiological saline solution, processing was conducted in the similar manner of Agent Production Example 10, and 10 ml of the liquid agent was prepared.

(Agent Production Example 16)

500 mg of the compound of Example 40 was dissolved in a physiological saline solution, processing was conducted in the similar manner of Agent Production Example 10, and 10 ml of the liquid agent was prepared.

(Agent Production Example 17)

600 mg of the compound of Example 41 was dissolved in a physiological saline solution, processing was conducted in the similar manner of Agent Production Example 10, and 10 ml of the liquid agent was prepared.

(Agent Production Example 18)

600 mg of the compound of Example 42 was dissolved in a physiological saline solution, processing was conducted in the similar manner of Agent Production Example 10, and 10 ml of the liquid agent was prepared.

(Agent Production Example 19)

600 mg of the compound of Example 43 was dissolved in a physiological saline solution, processing was conducted in the similar manner of Agent Production Example 10, and 10 ml of the liquid agent was prepared.

(Agent Production Example 20)

A powdered mixture of 500 mg of the compound of Example 30, 1000 mg of mannitol, and 400 mg of disodium phosphate was placed in a dry-sterilized ampule to prepare a 10 ml ampule.

(Agent Production Example 21)

A powdered mixture of 500 mg of the compound of Example 31, 1000 mg of mannitol, and 400 mg of disodium phosphate was placed in a dry-sterilized ampule to prepare a 10 ml ampule.

(Agent Production Example 22)

A powdered mixture of 500 mg of the compound of Example 32, 1000 mg of mannitol, and 400 mg of disodium phosphate was placed in a dry-sterilized ampule to prepare a 10 ml ampule.

(Agent Production Example 23)

A powdered mixture of 500 mg of the compound of Example 33, 1000 mg of mannitol, and 400 mg of disodium phosphate was placed in a dry-sterilized ampule to prepare a 10 ml ampule.

(Agent Production Example 24)

A powdered mixture of 500 mg of the compound of Example 34, 1000 mg of mannitol, and 400 mg of disodium phosphate was placed in a dry-sterilized ampule to prepare a 10 ml ampule.

What is claimed is:

1. A sulfated oligosaccharide aromatic glycoside of the formula:

$$(Z)_m-W-Y-(O)_n-R$$

wherein R is a straight or branched alkyl group having 1–18 carbon atoms;

n is 0 or 1;

Y is a phenylene group;

W is glucose bonded to Y by an ether bond through the hydroxyl group at the 1-position of the glucose;

$(Z)_m$—W is an oligosaccharide bonded by means of $\beta(1\rightarrow3)$ glycoside bonds, wherein Z is glucose and m is an integer from 1 to 19; and wherein at least 10% of the remaining hydroxyl groups of the oligosaccharide are substituted with sulfate groups; or a pharmaceutically acceptable salt thereof.

2. A sulfated oligosaccharide aromatic glycoside of the formula:

$$(Z)_m-W-Y-(O)_n-R$$

wherein R is a straight or branched alkyl group having 1–18 carbon atoms;

n is 0 or 1;

Y is a phenylene group;

W is glucose bonded to Y by an ether bond through the hydroxyl group at the 1-position of the glucose;

$(Z)_m$—W is an oligosaccharide bonded by means of $\beta(1\rightarrow4)$ glycoside bonds, wherein Z is galactose and m is an integer from 1 to 19; and wherein at least 10% of the remaining hydroxyl groups of the oligosaccharide are substituted with sulfate groups; or a pharmaceutically acceptable salt thereof.

3. An anti-virally active composition against human immunodeficiency virus comprising a sulfated oligosaccharide aromatic glycoside according to claims 1 or 2 as its active component in combination with a pharmaceutically acceptable carrier.

* * * * *